US011911682B2

United States Patent
Cox et al.

(10) Patent No.: US 11,911,682 B2
(45) Date of Patent: Feb. 27, 2024

(54) TRAINING SYSTEMS AND METHODS

(71) Applicant: BREAKOUT HITTING LLC, Cypress, TX (US)

(72) Inventors: Preston Carpenter Cox, Cypress, TX (US); Robin Birdwell Cox, Cypress, TX (US)

(73) Assignee: VXT SPORTS LLC, Cypress, TX (US)

( * ) Notice: Subject to any disclaimer, the term of this patent is extended or adjusted under 35 U.S.C. 154(b) by 86 days.

(21) Appl. No.: 17/648,106

(22) Filed: Jan. 14, 2022

(65) Prior Publication Data

US 2022/0258022 A1 Aug. 18, 2022

Related U.S. Application Data

(63) Continuation of application No. 17/390,572, filed on Jul. 30, 2021, now Pat. No. 11,278,784.

(Continued)

(51) Int. Cl.
*A63B 69/40* (2006.01)
*A63B 24/00* (2006.01)
(Continued)

(52) U.S. Cl.
CPC ........ *A63B 69/409* (2013.01); *A63B 24/0062* (2013.01); *A61B 3/112* (2013.01);
(Continued)

(58) Field of Classification Search
CPC .............. A63B 69/409; A63B 24/0062; A63B 2024/0034; A63B 2214/00;
(Continued)

(56) References Cited

U.S. PATENT DOCUMENTS 3,838,676 A 10/1974 Kahelin
3,989,027 A 11/1976 Kahelin
(Continued)

FOREIGN PATENT DOCUMENTS

EP 3535034 A2 9/2019
JP 2021146193 A 9/2021
(Continued)

OTHER PUBLICATIONS

International Search Report for PCT App No. PCT/US2021/071075 dated Nov. 24, 2021, 2 pgs.
(Continued)

*Primary Examiner* — Jeffrey S Vanderveen
(74) *Attorney, Agent, or Firm* — Abel Schillinger, LLP

(57) ABSTRACT

A method can include providing an object having a size smaller than a size of a known regulation object, projecting the object, via a delivery device, toward a trainee, and training the trainee to follow the object. A method can include determining a game parameter of a game trajectory of a sports object that was projected along the game trajectory in a real-time sports event, and based on the game parameters, adapting a delivery device to deliver a training object along a training trajectory that mimics at least a portion of the game trajectory, with the training object being smaller than the sports object.

20 Claims, 23 Drawing Sheets

Related U.S. Application Data

(60) Provisional application No. 63/203,149, filed on Jul. 9, 2021, provisional application No. 63/149,351, filed on Feb. 14, 2021.

(51) Int. Cl.
*A61B 3/11* (2006.01)
*A61B 3/113* (2006.01)
*A61B 3/14* (2006.01)

(52) U.S. Cl.
CPC .................. *A61B 3/113* (2013.01); *A61B 3/14* (2013.01); *A63B 2024/0034* (2013.01); *A63B 2214/00* (2020.08); *A63B 2220/05* (2013.01)

(58) Field of Classification Search
CPC ............ A63B 2220/05; A63B 71/0669; A63B 2024/0043; A63B 2024/0068; A63B 2069/0008; A63B 2069/402; A63B 2071/0625; A63B 2071/0675; A63B 2102/16; A63B 2220/13; A63B 2220/62; A63B 2220/806; A63B 2220/89; A63B 2225/09; A63B 2225/20; A63B 2230/00; A63B 69/40; A63B 69/38; A63B 69/0026; A63B 69/0015; A63B 69/002; A63B 43/008; A63B 43/06; A63B 69/0002; A63B 24/0003; A63B 69/00; A63B 69/0075; A63B 69/0079; A63B 71/021; A63B 71/022; A63B 71/0622; A63B 2024/0056; A63B 2069/0006; A63B 2069/401; A63B 2071/025; A63B 2071/0647; A63B 2102/14; A63B 2102/182; A63B 2220/53; A63B 2220/805; A63B 2220/833; A63B 2225/02; A63B 2225/093; A63B 2225/74; A61B 3/112; A61B 3/113; A61B 3/14

See application file for complete search history.

(56) References Cited

U.S. PATENT DOCUMENTS

| | | |
|---|---|---|
| 4,091,791 A | 5/1978 | Castelli et al. |
| 4,442,823 A | 4/1984 | Floyd et al. |
| 5,265,583 A | 11/1993 | Otto |
| 5,464,208 A | 11/1995 | Pierce |
| 5,507,271 A | 4/1996 | Actor |
| 5,735,256 A | 4/1998 | Monk |
| 5,897,445 A | 4/1999 | Sanders et al. |
| 6,082,350 A | 7/2000 | Crews et al. |
| 6,241,629 B1 | 6/2001 | Otto |
| 6,254,498 B1 | 7/2001 | Tyner |
| 6,807,959 B1 | 10/2004 | Murdock et al. |
| 7,011,084 B2 | 3/2006 | Richard |
| 7,156,761 B2 | 1/2007 | Mesa |
| 7,300,357 B2 | 11/2007 | Breaker et al. |
| 7,841,950 B2 | 11/2010 | Davidson et al. |
| 8,553,936 B2 | 10/2013 | Fogt |
| 9,010,309 B2 | 4/2015 | Lewis et al. |
| 9,180,355 B1 | 11/2015 | Boehner |
| 9,604,114 B2 | 3/2017 | Lee et al. |
| 11,278,784 B2 | 3/2022 | Cox et al. |
| 2003/0040381 A1 | 2/2003 | Richings et al. |
| 2005/0085321 A1 | 4/2005 | Diveglio |
| 2005/0172943 A1 | 8/2005 | Cucjen et al. |
| 2006/0068365 A1 | 3/2006 | Smith |
| 2006/0196490 A1 | 9/2006 | Davidson et al. |
| 2007/0072704 A1 | 3/2007 | Wey |
| 2007/0191143 A1 | 8/2007 | Kelly et al. |
| 2008/0021651 A1 | 1/2008 | Seeley et al. |
| 2009/0095273 A1 | 4/2009 | Paulson et al. |
| 2012/0051597 A1* | 3/2012 | Fogt .................. G06F 3/012 382/103 |
| 2016/0193520 A1 | 7/2016 | Hart |
| 2016/0339316 A1 | 11/2016 | Lee et al. |
| 2017/0266530 A1 | 9/2017 | Pepe |
| 2018/0156914 A1 | 6/2018 | Tuxen et al. |
| 2019/0091535 A1 | 3/2019 | DeCarlo |
| 2019/0201794 A1 | 7/2019 | Kang |
| 2020/0197782 A1 | 6/2020 | Abdelmoneum et al. |
| 2020/0298092 A1 | 9/2020 | Okur et al. |
| 2021/0149482 A1 | 5/2021 | Council |
| 2022/0032155 A1 | 2/2022 | Cox et al. |
| 2022/0258021 A1 | 8/2022 | Cox et al. |

FOREIGN PATENT DOCUMENTS

| | | |
|---|---|---|
| KR | 10-2008-0007777 A | 1/2008 |
| KR | 101435506 B1 | 9/2014 |
| KR | 10-2016-0059844 A | 5/2016 |
| KR | 10-2018460 B1 | 9/2019 |
| KR | 102045449 B1 | 11/2019 |
| KR | 10-2020-0019556 A | 2/2020 |
| KR | 102265914 B1 | 6/2021 |
| WO | 2018085073 A2 | 5/2018 |
| WO | 2021051196 A1 | 3/2021 |

OTHER PUBLICATIONS

International Search Report and Written Opinion for PCT/US2023/061568, dated Jun. 12, 2023, 10 pages.
International Search Report and Written Opinion for PCT/US2023/061577, dated Jun. 5, 2023, 11 pages.

* cited by examiner

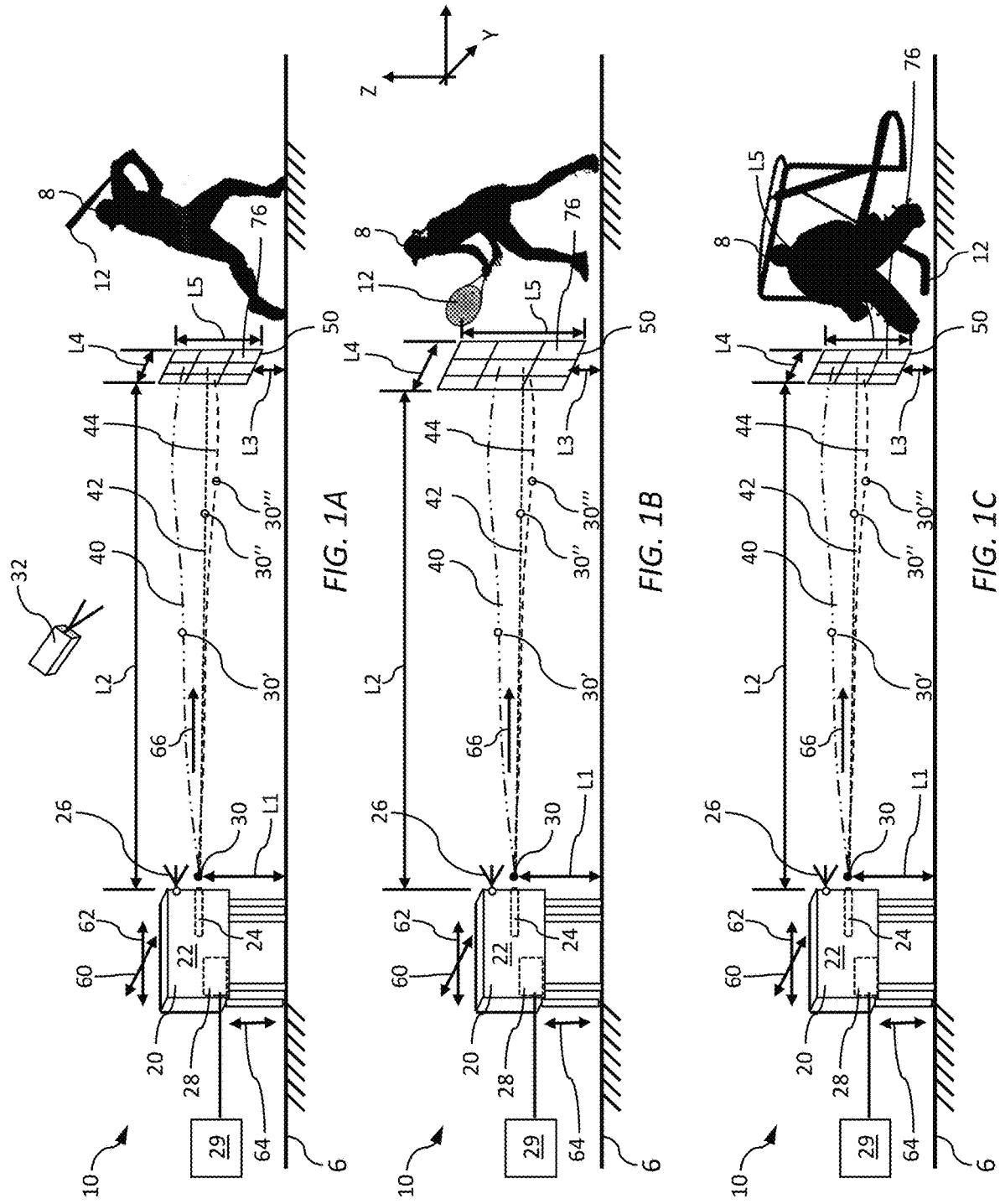

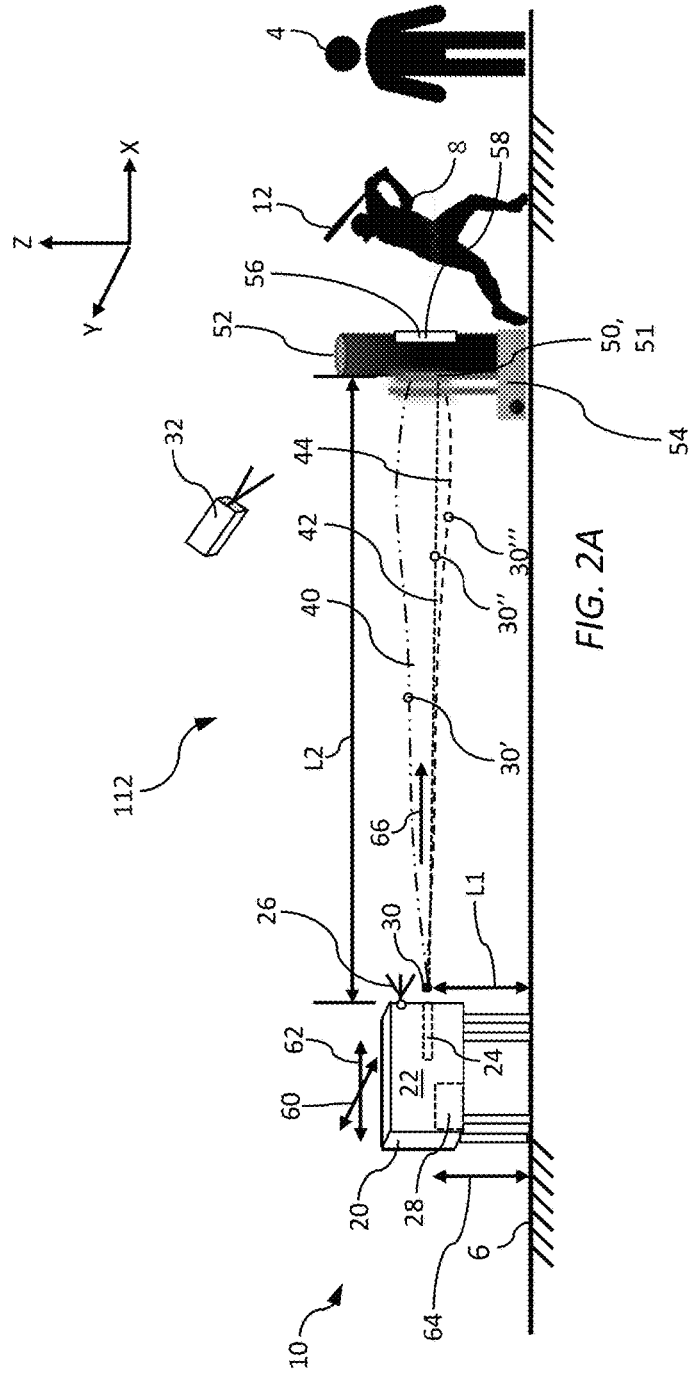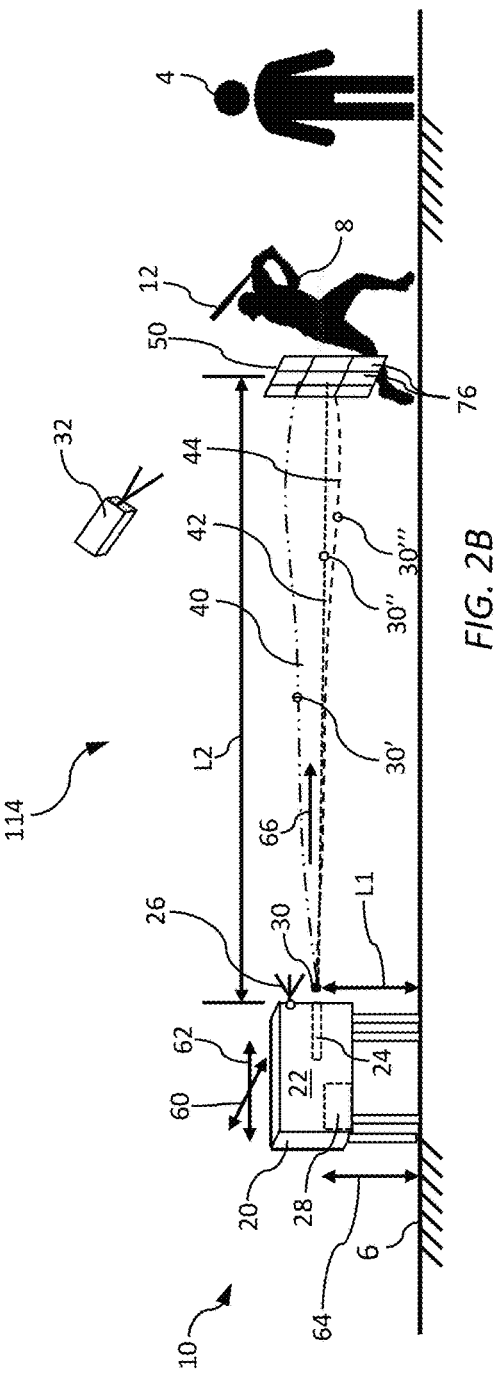

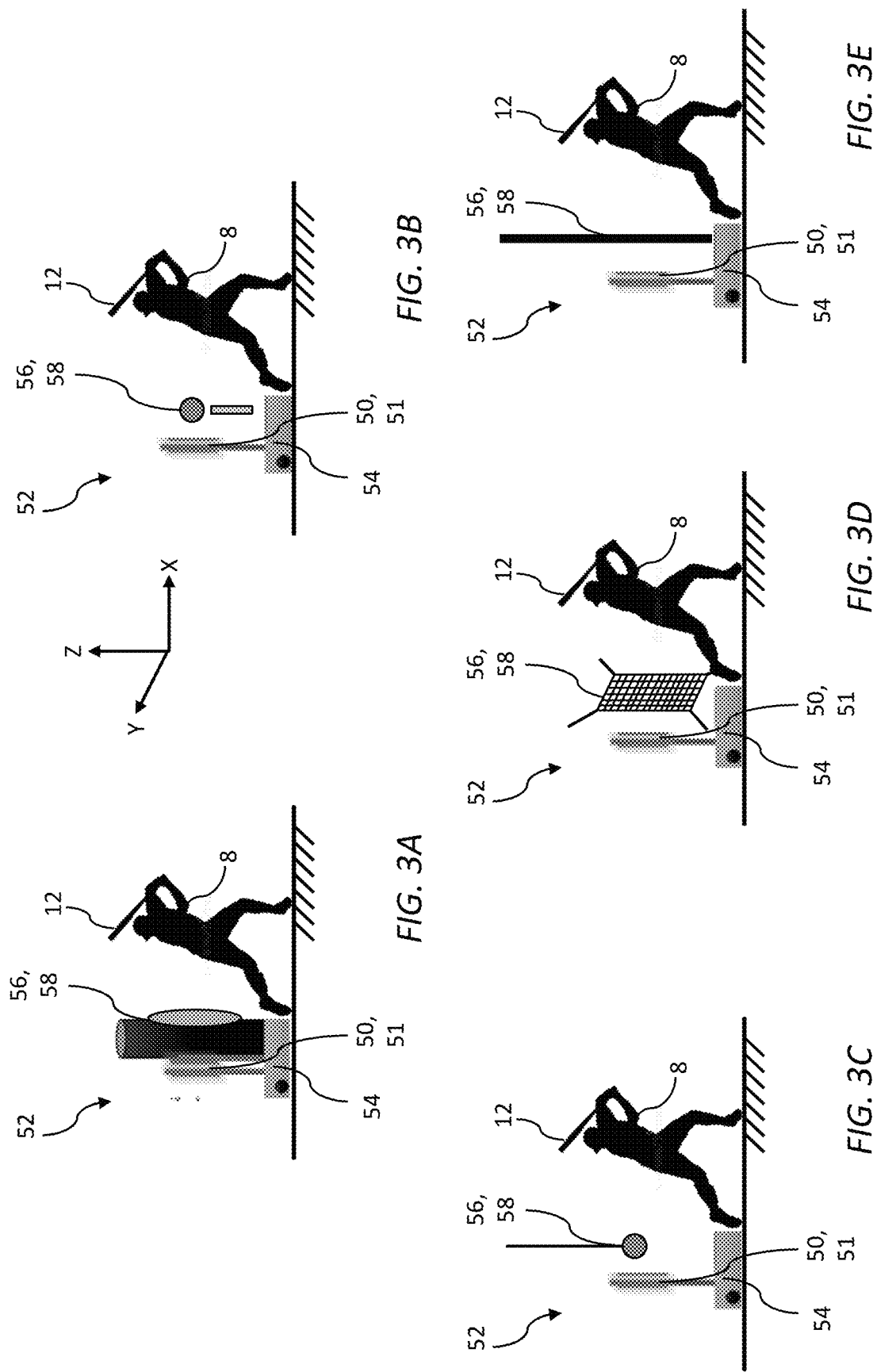

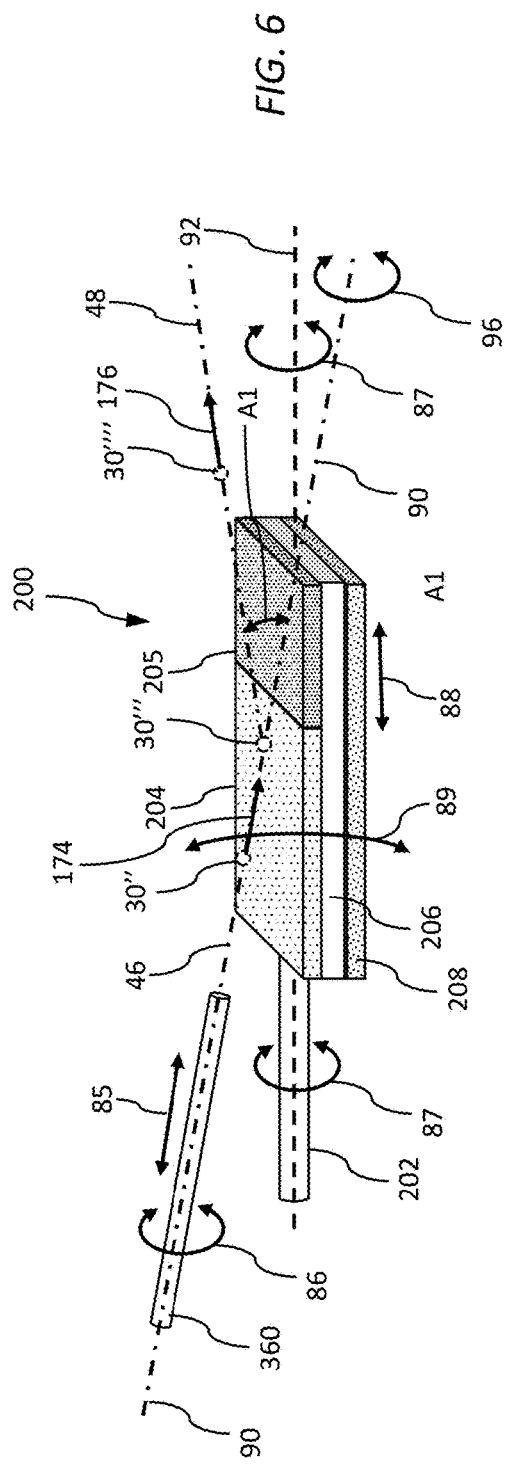
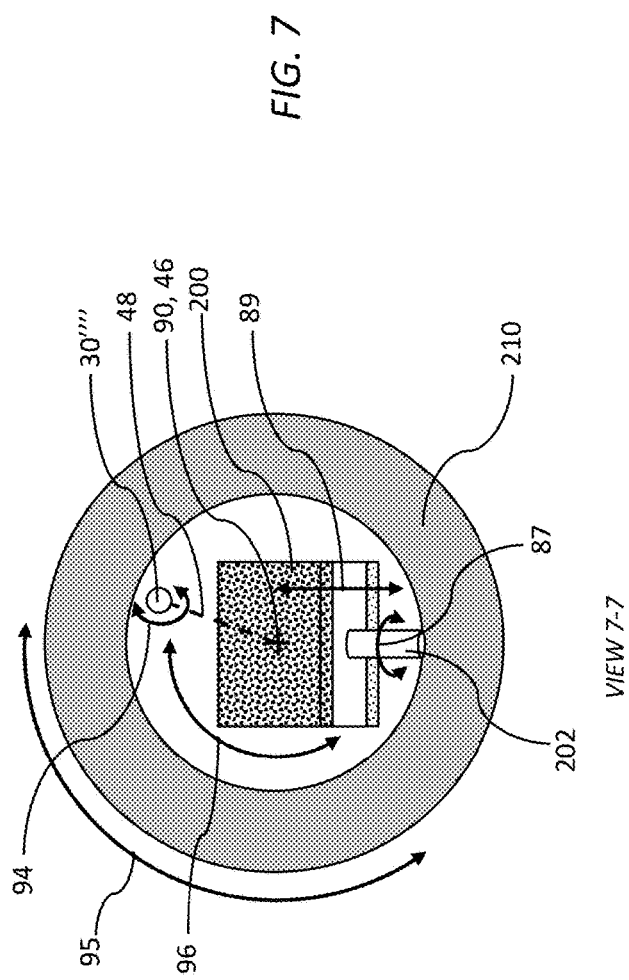

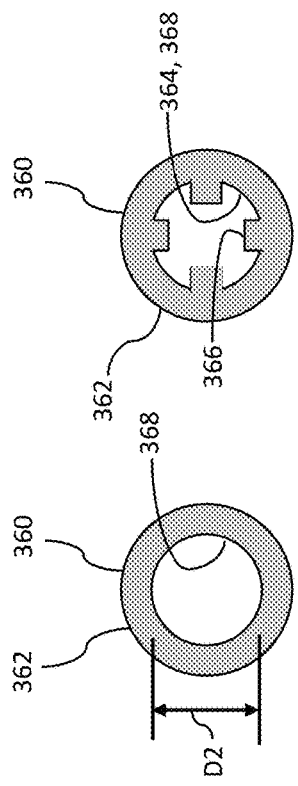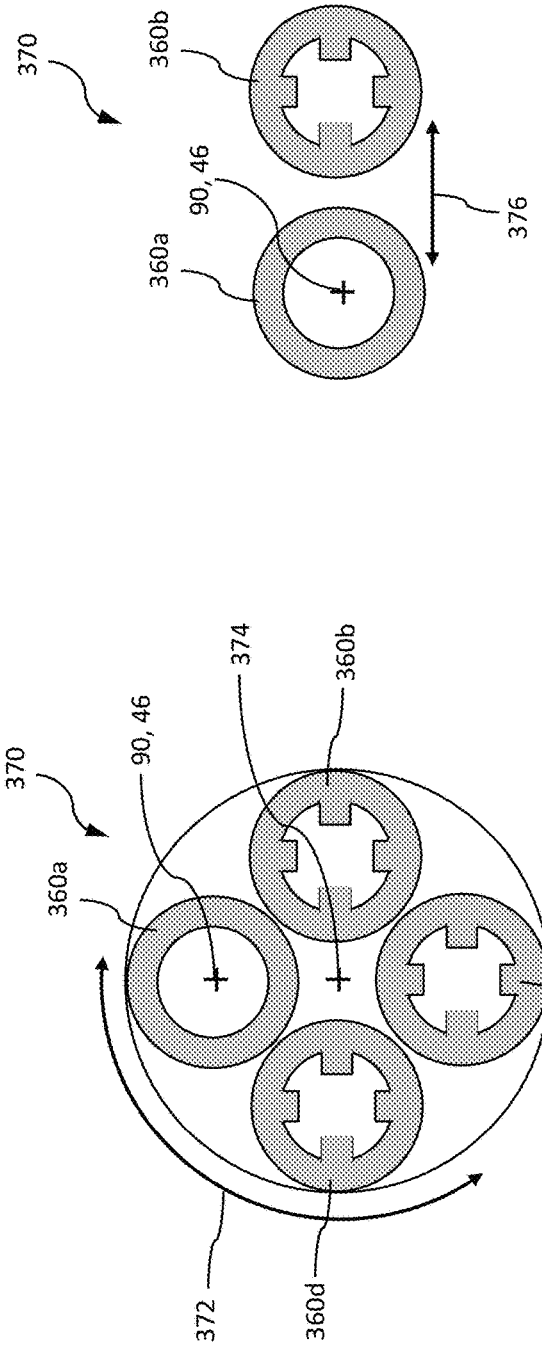

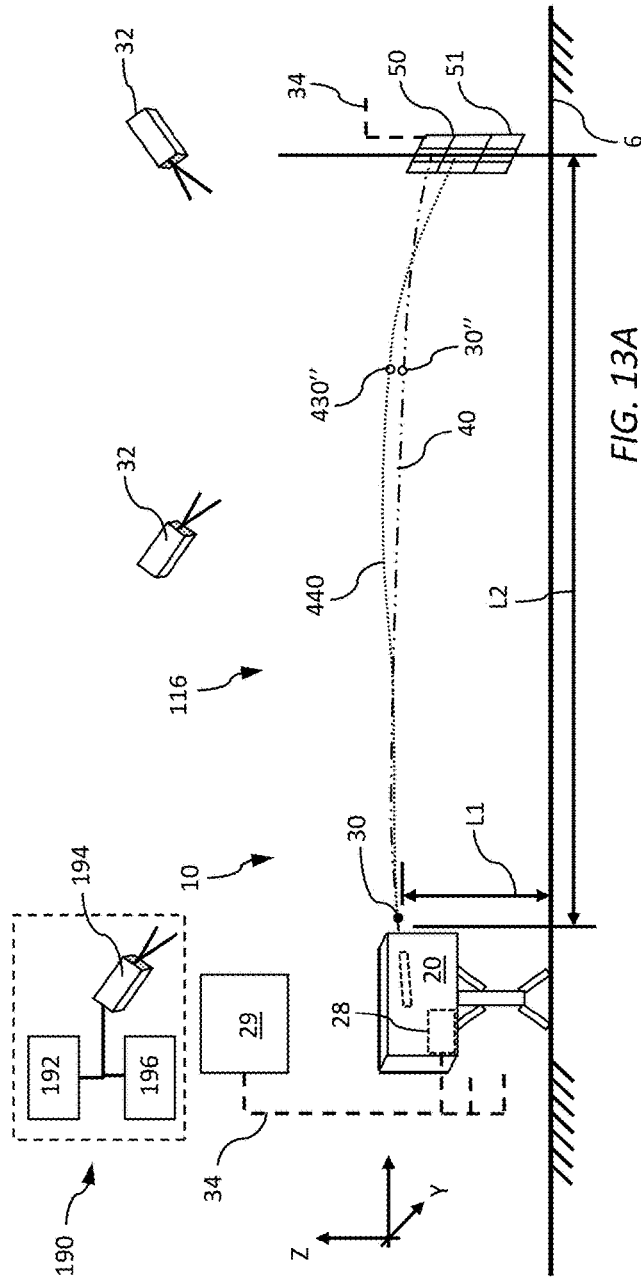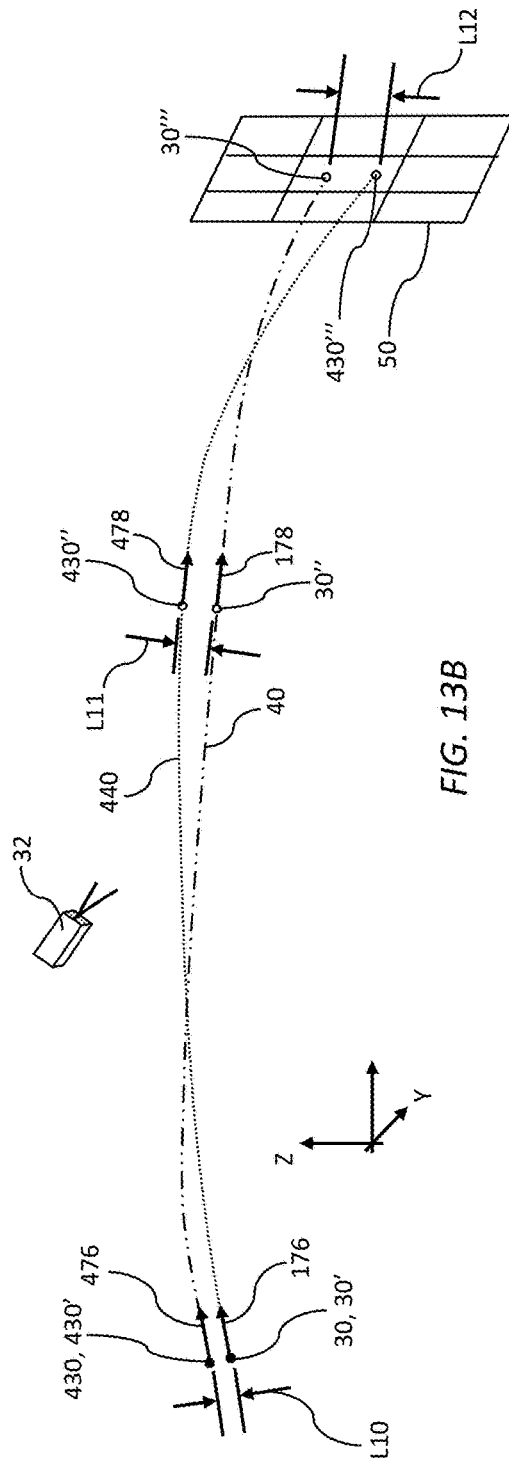

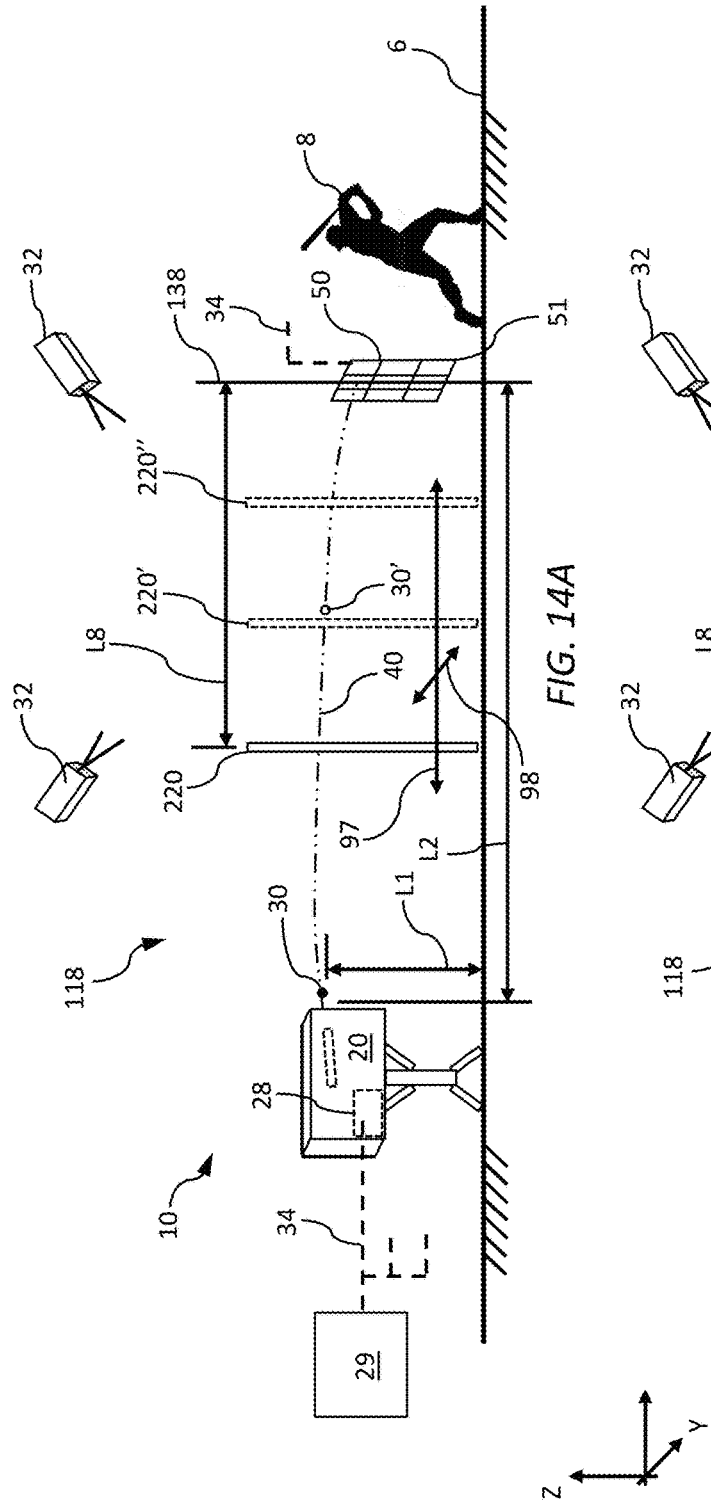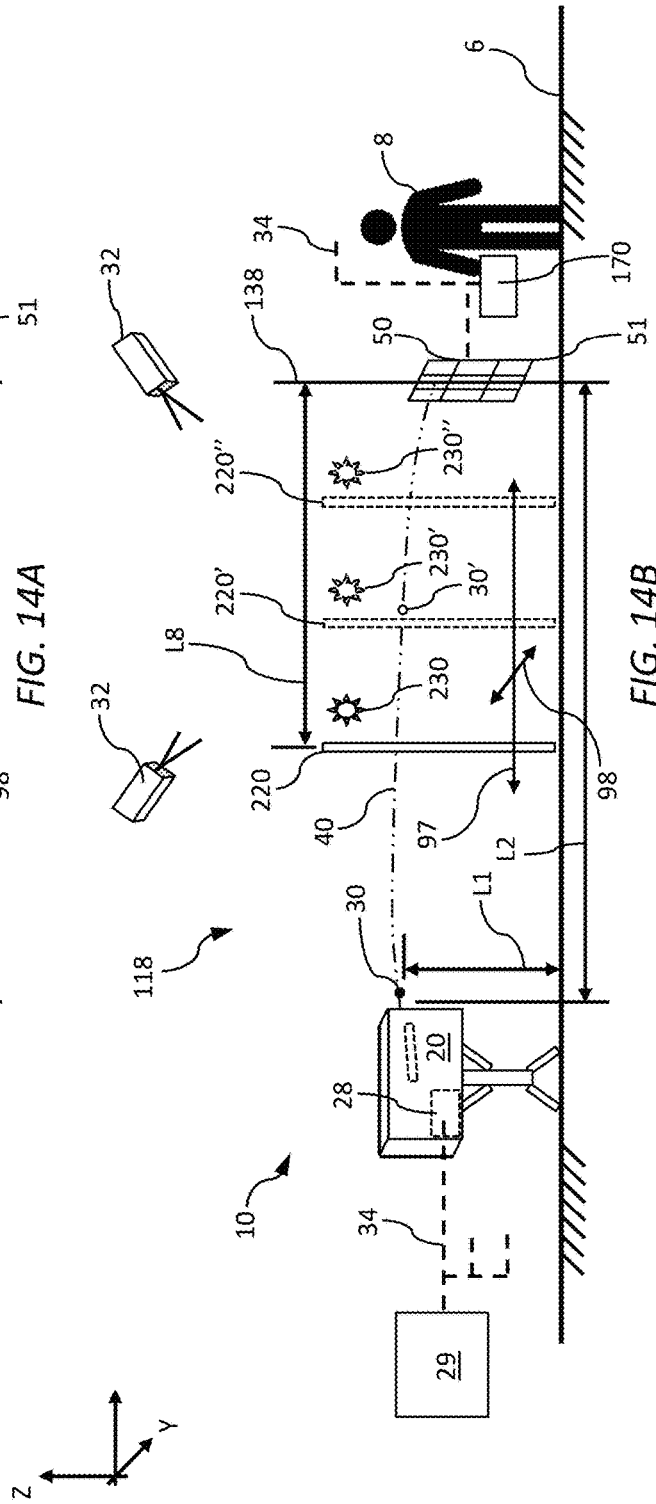

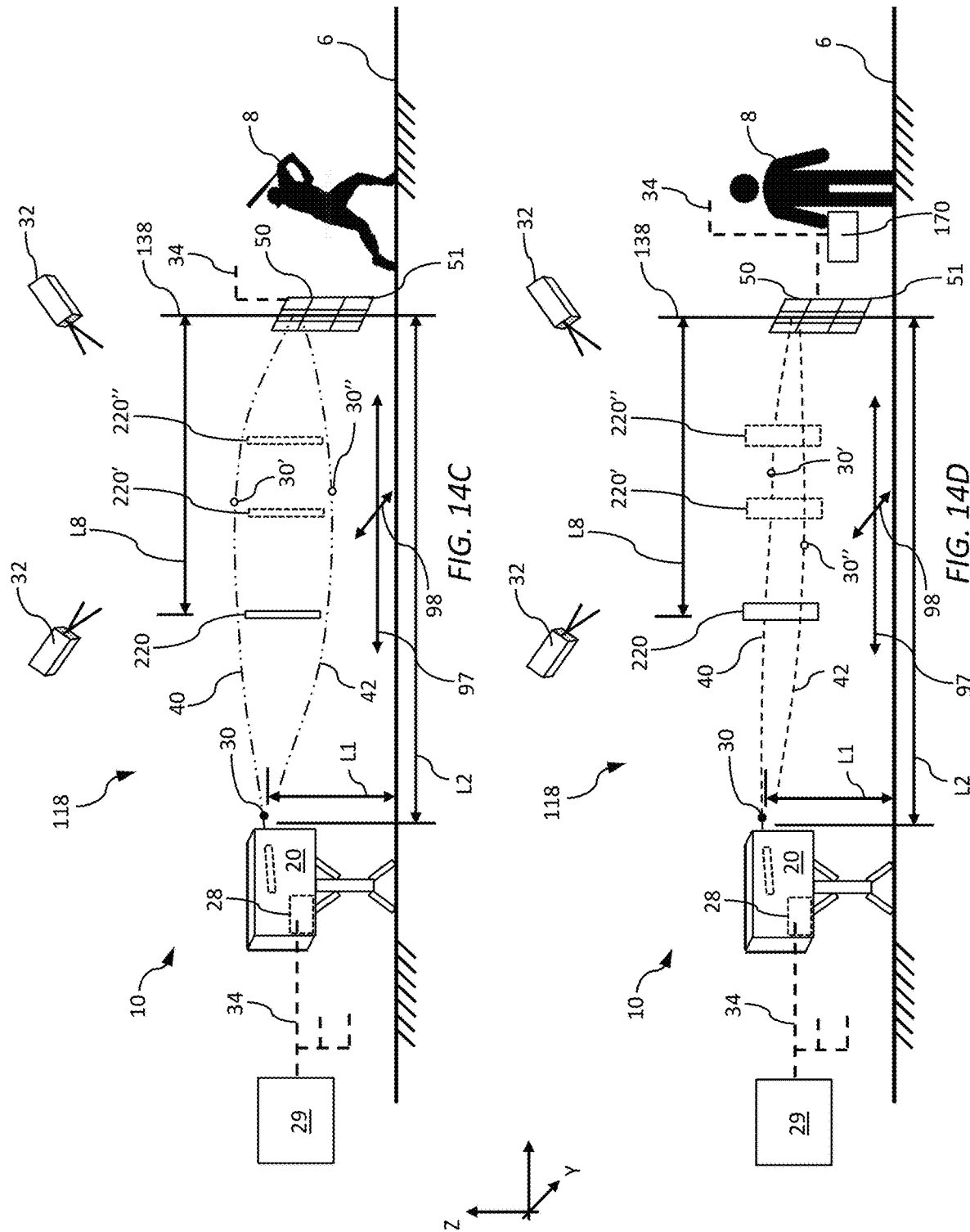

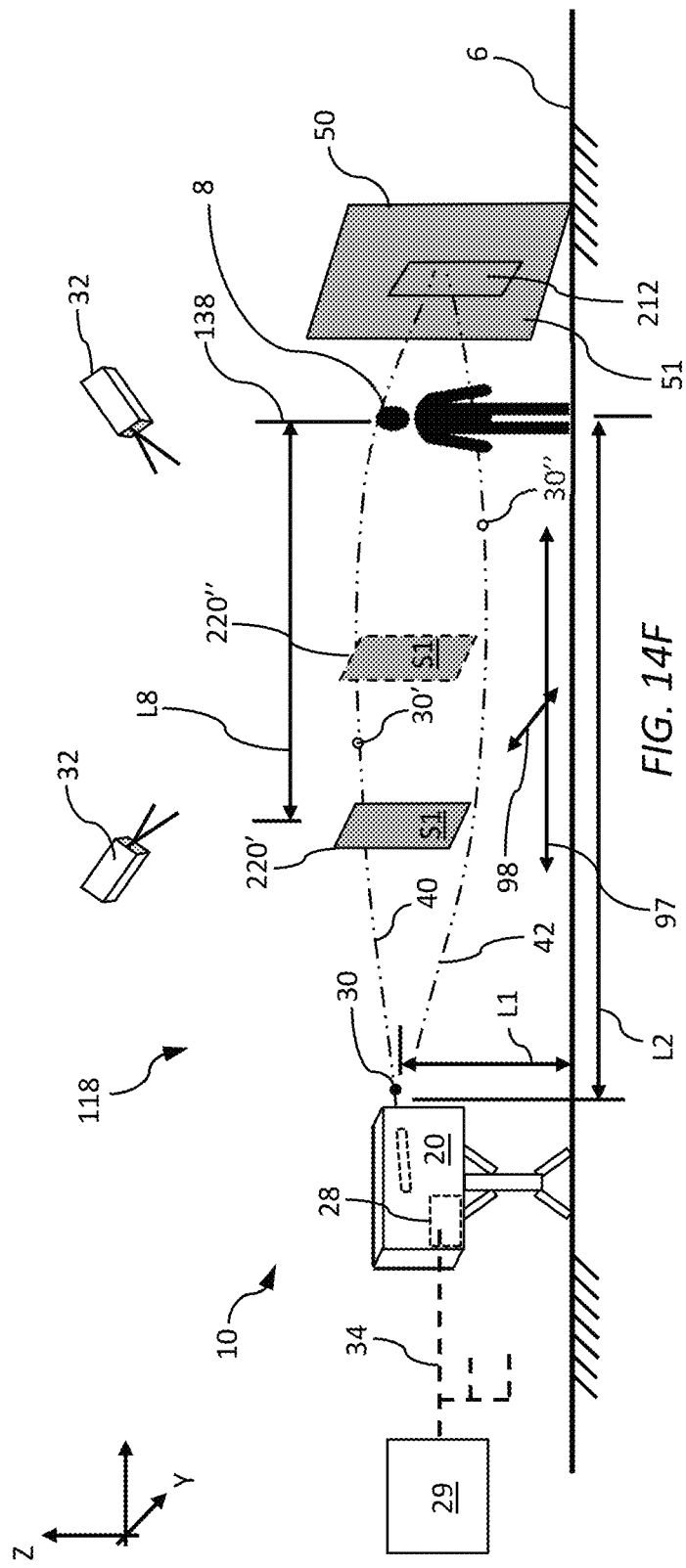

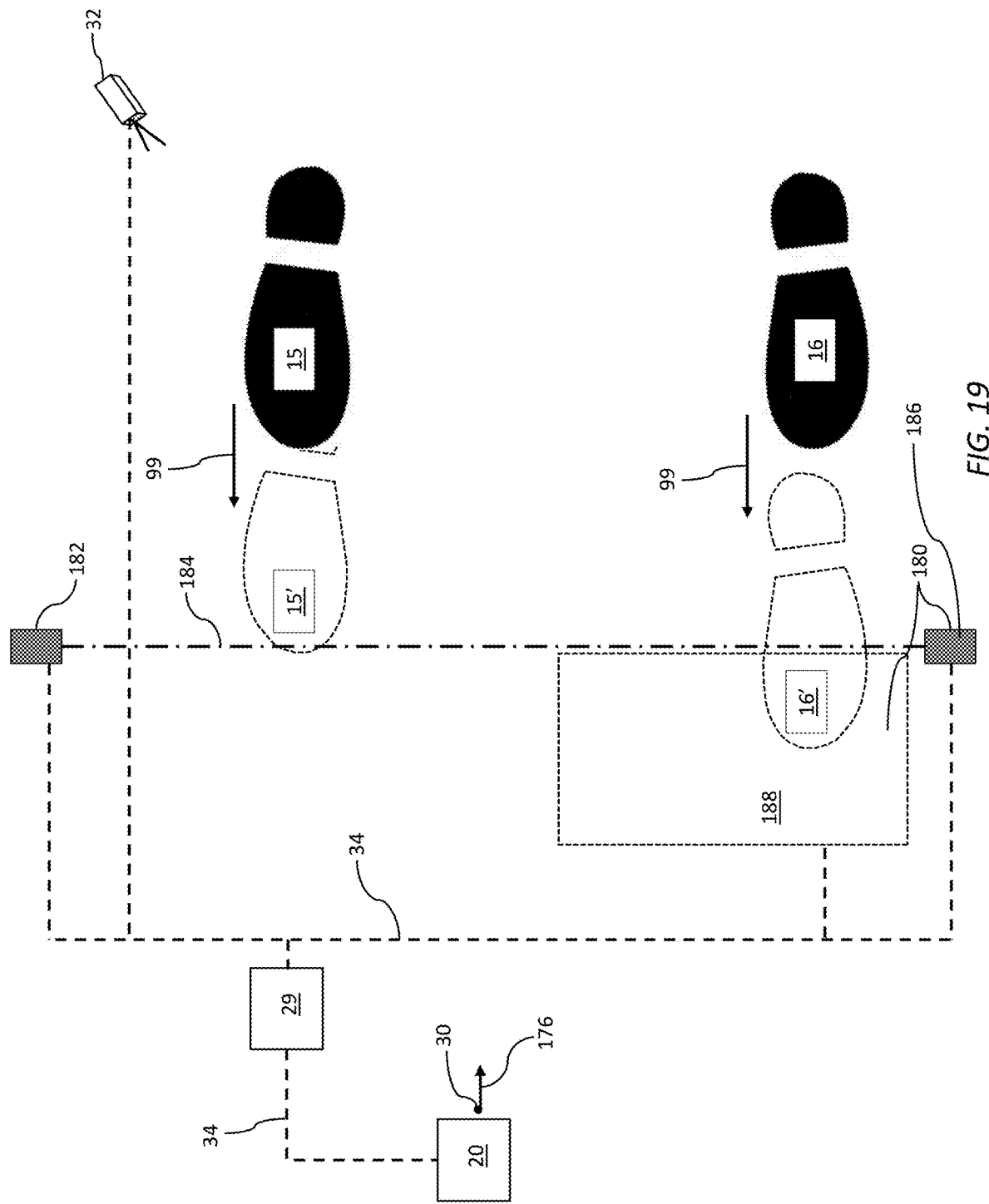

TRAINING SYSTEMS AND METHODS

CROSS-REFERENCE TO RELATED APPLICATION(S)

This application is a continuation and claims priority to U.S. patent application Ser. No. 17/390,572, entitled "TRAINING SYSTEMS AND METHODS," by Preston Carpenter COX et al., filed Jul. 30, 2021, which application claims priority under 35 U.S.C. § 119(e) to U.S. Provisional Application No. 63/149,351, entitled "TRAINING SYSTEM AND METHOD OF USING SAME," by Preston Carpenter COX et al., filed Feb. 14, 2021, and to U.S. Provisional Application No. 63/203,149, entitled "TRAINING SYSTEM AND METHOD OF USING SAME," by Preston Carpenter COX et al., filed Jul. 9, 2021, of which all three application are assigned to the current assignee hereof and incorporated herein by reference in their entireties.

TECHNICAL FIELD

The present invention relates, in general, to the field of training individuals to improve their performance in their field of work or play. More particularly, present embodiments relate to a system and method for projecting an object toward a target and a trainee (or individual) interacting with the object.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by the data processing apparatus, cause the apparatus to perform the actions.

One general aspect includes a method for sports training. The method also includes determining game parameters of a game trajectory of a sports object that was projected along the game trajectory in a real-time sports event; and based on the game parameters, adapting a delivery device to deliver a training object along a training trajectory that mimics at least a portion of the game trajectory, where the training object is smaller than the sports object. Other embodiments of this aspect include corresponding computer systems, apparatus, and computer programs recorded on one or more computer storage devices, each configured to perform the actions of the methods.

One general aspect includes a system for training a trainee in performing a sport. The system also includes a delivery device that projects an object toward a target along a trajectory; a sensor that is configured to detect eye characteristics of the trainee, where the trainee is configured to track the object; and a computing system configured to determine a score of the trainee based upon the detected eye characteristics. Other embodiments of this aspect include corresponding computer systems, apparatus, and computer programs recorded on one or more computer storage devices, each configured to perform the actions of the methods.

One general aspect includes a method for sports training. The method also includes projecting, via a delivery device, an object toward a target along an actual trajectory; tracking the object along at least a portion of the actual trajectory, comparing the portion of the actual trajectory to a corresponding portion of a desired trajectory, and adjusting one or more parameters of the delivery device based on the comparing. Other embodiments of this aspect include corresponding computer systems, apparatus, and computer programs recorded on one or more computer storage devices, each configured to perform the actions of the methods.

One general aspect includes a method for sports training. The method also includes projecting, via a delivery device, an object toward a target along a trajectory; tracking the object along at least a distal portion of the trajectory, where the distal portion of the trajectory includes the object arriving at the target; scoring a performance score of a trainee to track the object along the distal portion of the trajectory; and based on the scoring, increasing or decreasing a distance of the distal portion of the trajectory along which the trainee is configured to track the object prior to the object arriving at the target. Other embodiments of this aspect include corresponding computer systems, apparatus, and computer programs recorded on one or more computer storage devices, each configured to perform the actions of the methods.

One general aspect includes a method for sports training. The method also includes projecting, via a delivery device, an object toward an impact device along a trajectory; receiving the object at a target zone of the impact device, a trainee striking the impact device at an impact zone with a sports tool and scoring a performance score of the trainee to impact the impact zone at an appropriate time compared to an arrival time of the object at the target zone. Other embodiments of this aspect include corresponding computer systems, apparatus, and computer programs recorded on one or more computer storage devices, each configured to perform the actions of the methods.

One general aspect includes a method for sports training. The method also includes projecting, via a delivery device, an object toward a target along a trajectory, where the target may include a target zone; receiving the object at an actual arrival position at the target, where the actual arrival position is either inside the target zone or outside the target zone, and where a trainee is configured to send an indication, via a human-machine interface (HMI) device, when the trainee expects the object to arrive inside the target zone; comparing the indication to the actual arrival position; and determining a performance score based on the comparing. Other embodiments of this aspect include corresponding computer systems, apparatus, and computer programs recorded on one or more computer storage devices, each configured to perform the actions of the methods.

One general aspect includes a method for sports training. The method also includes projecting, via a delivery device, a first object toward a target; impacting a friction device of the delivery device with the first object; imparting a first spin and a first deflection to the first object in response to impacting the friction device, thereby projecting the first object along a first trajectory to the target; automatically adjusting, via a controller, one or more parameters of the delivery device; projecting, via the delivery device, a second object toward the target; impacting the friction device with the second object; and imparting a second spin and a second deflection to the second object, thereby projecting the second object along a second trajectory to the target. Other embodiments of this aspect include corresponding computer systems, apparatus, and computer programs recorded on one or more computer storage devices, each configured to perform the actions of the methods.

One general aspect includes a system for sports training a delivery device that projects a first object toward a target along a first trajectory and a second object toward a target along a second trajectory, the delivery device may include: a propulsion device that propels the first object or the second object from the delivery device, and a friction device that imparts a spin and a deflection to the first object or the second object as the respective first object or second object is propelled toward the target, where the friction device is automatically controlled to vary the second trajectory of the second object compared to the first trajectory of the first object.

BRIEF DESCRIPTION OF THE DRAWINGS

Features, aspects, and advantages of present embodiments will become better understood when the following detailed description is read with reference to the accompanying drawings in which like characters represent like parts throughout the drawings, wherein:

FIGS. 1A-1C are representative functional diagrams of systems and methods for training a trainee to improve coordination, vision training and/or tracking capabilities, and vision training and/or timing capabilities, in accordance with certain embodiments;

FIG. 2A is a representative functional diagram of a system and method for training a trainee to improve coordination, vision training, and/or tracking capabilities, including an impact device, in accordance with certain embodiments;

FIG. 2B is a representative functional diagram of a system and method for training a trainee to improve coordination, vision training, and/or tracking capabilities, without an impact device, in accordance with certain embodiments;

FIGS. 3A-3E are representative side views of an impact device; in accordance with certain embodiments;

FIG. 6 is a representative perspective view of a friction device for the delivery device, in accordance with certain embodiments;

FIG. 7 is a representative partial cross-sectional view along line 7-7 shown in FIG. 5, in accordance with certain embodiments;

FIGS. 8A-8D are representative partial cross-sectional views along line 8-8 in FIG. 5 of a barrel or barrel assembly of a delivery device, in accordance with certain embodiments;

FIG. 13A is a representative functional block diagram of a training system that can support a method of calibration, in accordance with certain embodiments;

FIG. 13B is a representative detailed view of a portion of the functional block diagram shown in FIG. 13A, in accordance with certain embodiments;

FIGS. 14A-14F are representative functional diagrams of systems and methods for training a trainee to improve coordination, vision training, and/or tracking capabilities through segmenting training, in accordance with certain embodiments;

FIG. 19 is a representative functional diagram of a system and method for initiating a delivery of an object along a trajectory in response to a gesture of a trainee or coach, in accordance with certain embodiments.

DETAILED DESCRIPTION

Figure 1E:
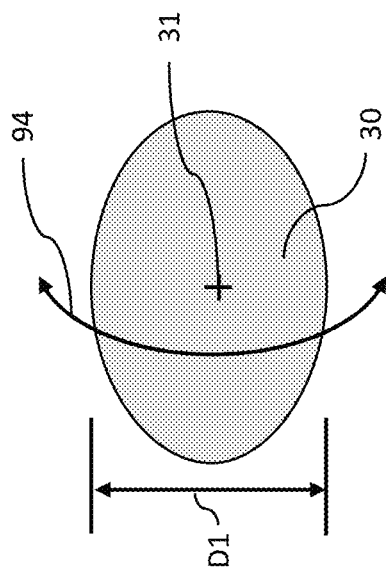
FIGS. 1D-1E are representative diagrams of an object used with a delivery device for training a trainee to improve coordination, vision training and/or tracking capabilities, and vision training and/or timing capabilities, in accordance with certain embodiments.

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings.

As used herein, the terms "comprises," "comprising," "includes," "including," "has," "having," or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present), and B is false (or not present), A is false (or not present), and B is true (or present), and both A and B are true (or present).

The use of "a" or "an" is employed to describe elements and components described herein. This is done merely for convenience and to give a general sense of the scope of the invention. This description should be read to include one or at least one and the singular also includes the plural, or vice versa, unless it is clear that it is meant otherwise.

The use of the word "about", "approximately", or "substantially" is intended to mean that a value of a parameter is close to a stated value or position. However, minor differences may prevent the values or positions from being exactly as stated. Thus, differences of up to ten percent (10%) for the value are reasonable differences from the ideal goal of exactly as described. A significant difference can be when the difference is greater than ten percent (10%).

FIGS. 1A-1C are representative functional diagrams of a system 10 for training a trainee 8 to improve coordination, vision training, and/or tracking capabilities. Such a system 10 and method of using the system as disclosed according to the embodiments herein may be particularly suited for sports training. However, it will be appreciated that other uses may be possible. Such sports may include, without limitation, baseball (FIG. 1A), tennis (FIG. 1B), or hockey (FIG. 1C). Other sports can also benefit from similar training, such as softball, lacrosse, cricket, soccer, table tennis, American football (referred to as "football"), volleyball, basketball, shooting sports, etc. Other training activities can also benefit from similar training using the systems described in this disclosure such as military training, first responder training, search and rescue training, rehabilitation training (e.g., where the trainee 8 is autistic, recovering from a stroke, recovering from an injury, or has other medical conditions), or other trainees that can benefit from eye-hand coordination training provided by the training systems described in this disclosure.

Military, first responders, and tactical officers often need to make quick but accurate decisions under stress. By improving time to recognize aspects of the field around them, they can more quickly determine risks and identify threats. Search and Rescue personnel can work in difficult, stressful, or poor operating environments. Enhanced visual skills can help reduce the time to recognize dangers, individuals, and risks of the situation. Visual skills that can be improved by the training systems in this disclosure are, but are not limited to:

Dynamic Visual Acuity,
Gaze Stabilization,
Initiation speed,
Peripheral Awareness,
Speed of Visual Processing,
Vision in Dim Illumination,
Visual Discrimination,
Concentration, or
Spatial Awareness.

FIGS. 1A, 1B, 1C show a delivery device 20 that can be used to project an object 30 toward a target zone 50 (or a trainee 8). According to an embodiment, the object 30 may be projected along a trajectory (e.g., 40, 42, 44) in a direction 66 toward the target zone 50 or trainee 8. As used herein, a "trajectory" is a representation of a flight path of an object through a three-dimensional (3D) X, Y, Z coordinate system space, where each point along the trajectory can be represented by a point in the 3D space. Each point along the trajectory can include a velocity vector that is representative of a velocity and direction of travel of the object at that point along the trajectory.

In one embodiment, the projection of the object 30 along the trajectory (40, 42, 44) may be controlled by one or more controllers 28, 29 (also referred to as "controller 28, 29") capable of controlling various aspects of the process of projection of the object 30, such that the projection is conducted along a predetermined trajectory 40, 42, or 44. The one or more controllers 28, 29 can include only one controller (28 or 29) that can control the aspects of the delivery device 20 and communicate with internal and external data sources for setting parameters of the delivery device 20 to desired values. The one or more controllers 28, 29 can also include an internal controller(s) 28 and an external controller(s) 29 that can control the aspects of the delivery device 20 and communicate with each of the controllers and with internal and external data sources for setting parameters of the delivery device 20 to desired values.

A predetermined trajectory can include a trajectory that is estimated (or determined) prior to the projection of the object 30. The predetermined trajectory can be selected by the controller 28, 29 which can be used to control one or more components of the delivery device 20 that may be used to control the trajectory of the object. The delivery device 20 can include or be communicatively coupled (wired or wirelessly) to the one or more controllers 28, 29 that can be configured to control one or more delivery variables associated with delivering the object along a predetermined trajectory 40, 42, or 44. In a non-limiting embodiment, the delivery variables can include, the position of the device in 3D-space (i.e., position in space according to X, Y, and Z planes), angle of the device relative to an intended target or trainee, distance from a target or trainee, the intended velocity of the object along the intended trajectory between the device and the target or trainee, the spin of the object along the intended trajectory between the device and the target or trainee, the weight of the object by selecting an object, surface features of the object by selecting the object, as well as others. Additional delivery variables (or parameters) are defined in the following description at least in regard to FIGS. 5A-10. In a non-limiting embodiment, these parameters can be:

air pressure supplied to the object to propel the object through a barrel with a center axis;
air volume supplied to the object;
inclination of the barrel;
azimuthal orientation of the barrel;
length of the barrel;
inclination of a friction device which comprises a ramp and a surface material on the ramp;
azimuthal orientation of the friction device around the center axis of the barrel;
azimuthal orientation of the friction device about a longitudinal axis of the friction device;
distance of the friction device from the barrel;
the surface material of the friction device;
object launch position from the delivery device, the object launch position being a location in 3D space of an X-Y-Z coordinate system;
object selection;
distance to the target; and
height of the target.

The delivery device 20 can be moved horizontally shown by arrows 60, 62, or vertically shown by arrows 64. The height L1 of the object exiting the delivery device 20 can be adjusted by moving the chassis 22 of the delivery device 20 up or down (arrows 64) a desired distance. This 3D movement of the delivery device 20 can allow users (e.g., coach 4, trainer 4, individual 8, trainee 8, or others) to adjust the position that an object 30 exits the delivery device 20. This allows the exiting object 30 to be positioned so as to emulate a human or other real-life source for delivery of a regulation object (e.g., a regulation baseball, a regulation softball, a regulation hockey puck, a regulation tennis ball, a regulation table tennis ball, a regulation lacrosse ball, a regulation cricket ball, a regulation football, and a regulation soccer ball) such as by a pitcher for baseball or softball, a quarterback for football, a skeet delivery device for shooting sports, etc. As used herein, "real-life" or "real-life" event refers to a game, practice session, or tactical situation for which the trainee is training to improve performance. The real-life event would be those events that use regulation equipment to perform the sport or tactical operation or situations.

Additionally, the object 30 trajectory can be projected from the delivery device 20 at an appropriate angle A1 relative to a surface 6. A guide 24 can be used to cause the object to exit the delivery device 20 at an angle and cause the object to experience varied resistance when it is ejected from the guide 24. The guide 24 can include a barrel and a friction device for imparting spin and deflection to the object to project the object 30 along a predetermined trajectory. A controller 28, 29 can control the angle and position of the guide 24, as well as select the predetermined (or desired, or expected) trajectory from a plurality of trajectories or define the predetermined trajectory based on collected data from data sources. In a non-limiting embodiment, each predetermined trajectory (e.g., trajectories 40, 42, 44) can include any parameters needed to set up the delivery device 20 to deliver the object 30 along that particular predetermined trajectory (e.g., trajectories 40, 42, 44). In a non-limiting embodiment, the parameters can include an azimuthal direction of the guide 24 to produce a desired azimuthal direction of an object 30 exiting the delivery device 20. The parameters can also include the amount and location of resistance to be applied to the object as the object is propelled toward the exit of the delivery device 20. These will be described in more detail below with regard to the delivery device 20.

In a non-limiting embodiment, the parameters can also include the force to be applied to the object 30 that will propel the object 30 from the delivery device 20 and cause the object to travel along the predetermined trajectory (e.g., trajectories 40, 42, 44). In a non-limiting embodiment, the force can be applied to the object 30 via pneumatic, hydraulic, electrical, electro-mechanical, or mechanical power sources that can selectively vary the amount of force applied to the object 30. The parameters can also include which one of a plurality of objects 30 should be chosen to provide the desired trajectory. The plurality of objects 30 can have many different features which are described in more detail below. The controller 28, 29 can select the object 30 that is needed to produce the desired trajectory. The controller 28, 29 can control an alert feature 26 (such as turn ON or OFF a light, turn ON or OFF an audible signal, play a synchronized video of a real-life delivery source, etc.) to indicate that an object 30 is about to be projected from the delivery device 20 toward the target zone 50. The alert feature 26 can be any device that can alert the trainee 8 to be ready for the object 30 to exit the delivery device 20.

In a non-limiting embodiment, the object 30 can be a spherical or substantially spherical object used for training purposes. The object 30 may be shaped to represent a desired sport. In a non-limiting embodiment, the object 30 can come in different colors such as white, yellow, orange, red, blue, tan, grey, black, or a luminescent color. The color of the object 30 can be selected for the sport for which the trainee 8 is being trained or for the type of training being used. In a non-limiting embodiment, a colored pattern (e.g., red, yellow, white, green, blue, orange, or black pattern) can be applied on the object 30 to differentiate it from other objects 30. The colored pattern can be used to assist the trainee 8 in focusing intently on the object 30 so that they may pick up and track a particular sports ball quicker. The object may have one or more surface features (e.g., smooth, dimples, bumps, recesses, ridges, grainy texture, etc.) that facilitate delivery along various trajectories. In a non-limiting embodiment, the object 30 can be made from a material such as acrylonitrile butadiene styrene, polylactic acid, calcium carbonate, recycled paper, cotton, foam, plastics, calcites, rubber, a metal such as steel, lead, copper, aluminum, or metal alloys, a plant-based material, or a fungus-based material.

In at least one embodiment, the device can include a magazine that may contain a plurality of objects. The objects 30 in the magazine can be substantially the same or at least a portion of the objects 30 can have varied characteristics relative to the other objects 30. Object characteristics can include but are not limited to, shape, size (e.g., longest dimension or length of the object, which in the case of a sphere is the diameter and in the case of a disk is the diameter along a major surface), color, surface features, density, material (e.g., inorganic, organic, metal, polymer, ceramic, or any combination thereof), or any combination thereof. In one embodiment, the delivery device 20 can include a first magazine with a first portion of objects having a first object characteristic, and a second magazine with a second portion of objects having a second object characteristic different from the first object characteristic. In one embodiment, the device is capable of selecting a single object from the first portion or the second portion. Various parameters may be used to select different objects, which may include, but is not limited to, a method of training (e.g., a preselected training protocol), a measured or scored capability of a trainee, a selection by the trainee, an instruction from one or more devices (e.g., data input from a sensor, such as a sensor associated with an impact device) communicatively coupled to the controller 28, 29.

In a non-limiting embodiment, it can be desirable for the object 30 to be sized such that it is significantly smaller than a corresponding regulation object. A corresponding regulation object is determined based upon the intended sport for which the trainee is training. For example, when training for baseball, the corresponding regulation object would be the regulation size of a baseball. In one non-limiting embodiment, the difference in size between the object 30 and a corresponding regulation object can be expressed as a value of Lo/Lr, wherein Lo is the largest dimension (i.e., length) of the object 30 and Lr is the largest dimension (i.e., length) of the regulation object. In at least one embodiment, the difference in size (or ration Lo/Lr) can be not greater than 0.9 or not greater than 0.8 or not greater than 0.7 or not greater than 0.6 or not greater than 0.5 or not greater than 0.4 or not greater than 0.3 or not greater than 0.2 or not greater than 0.1. Still, in another non-limiting embodiment, the difference in size can be at least 0.001 or at least 0.002 or at least 0.004 or at least 0.006 or at least 0.008 or at least 0.01 or at least 0.02 or at least 0.03 or at least 0.05 or at least 0.07 or at least 0.1 or at least 0.15 or at least 0.2 or at least 0.25 or at least 0.3. It will be appreciated that the difference in size between the object 30 and a corresponding regulation object (Lo/Lr) can be within a range including any of the minimum and maximum values noted above, including, for example, but not limited to at least 0.001 and not greater than 0.9 or within a range of at least 0.001 and not greater than 0.5 or within a range of at least 0.002 and not greater than 0.006.

In a non-limiting embodiment, the diameter D1 (see FIGS. 1D, 1E) of the object 30 can be at least 0.05 inches, at least 0.06 inches, at least 0.07 inches, at least 0.08 inches, at least 0.09 inches, at least 0.10 inches, at least 0.110 inches, at least 0.118 inches, at least 0.120 inches, at least 0.125 inches, at least 0.130 inches, at least 0.135 inches, at least 0.140 inches, at least 0.145 inches, at least 0.150 inches, at least 0.20 inches, or at least 0.25 inches.

In another non-limiting embodiment, the diameter D1 of the object 30 can be no greater than 2.0 inches, no greater than 1.90 inches, no greater than 1.80 inches, no greater than 1.70 inches, no greater than 1.60 inches, no greater than 1.50 inches, no greater than 1.40 inches, no greater than 1.30 inches, no greater than 1.20 inches, no greater than 1.10 inches, no greater than 1.00 inches, no greater than 0.90 inches, no greater than 0.85 inches, no greater than 0.80 inches, no greater than 0.75 inches, no greater than 0.70 inches, no greater than 0.65 inches, no greater than 0.60 inches, no greater than 0.59 inches, no greater than 0.55 inches, no greater than 0.50 inches, no greater than 0.45 inches, no greater than 0.40 inches.

It will be appreciated that the diameter of the object 30 may be within a range including any one of the minimum and maximum values noted above, including, for example, but not limited to at least 0.05 inches and not greater than 2.0 inches, or within a range of at least 0.05 inches and not greater than 1.10 inches, or within a range of at least 0.07 inches and not greater than 1.00 inch.

In a non-limiting embodiment, the size of the object 30 can be at least 120 times smaller than a baseball, at least 220 times smaller than a softball, at least 400 times smaller than a soccer ball, at least 25 times smaller than a table tennis ball, at least 90 times smaller than a lacrosse ball, at least 40 times smaller than a hockey puck, at least 70 times smaller than a clay pigeon (for shooting sports), at least 110 times smaller than a cricket ball.

In a non-limiting embodiment, the weight of the object 30 can be at least 0.001 ounces, at least 0.002 ounces, at least 0.003 ounces, at least 0.004 ounces, at least 0.005 ounces, at least 0.006 ounces, at least 0.007 ounces, at least 0.008 ounces, at least 0.009 ounces, at least 0.010 ounces, at least 0.011 ounces, at least 0.012 ounces, at least 0.013 ounces, at least 0.014 ounces, at least 0.015 ounces, at least 0.20 ounces, at least 0.25 ounces, at least 0.30 ounces, at least 0.35 ounces, at least 0.40 ounces, at least 0.45 ounces, at least 0.50 ounces, at least 0.55 ounces, or at least 0.60 ounces.

In another non-limiting embodiment, the weight of the object 30 can be no greater than 10 ounces, no greater than 9 ounces, no greater than 8 ounces, no greater than 7 ounces, no greater than 6 ounces, no greater than 5 ounces, no greater than 4 ounces, no greater than 3 ounces, no greater than 2 ounces, no greater than 1.5 ounces, no greater than 1 ounce, no greater than 0.9 ounces, no greater than 0.8 ounces, no greater than 0.7 ounces, no greater than 0.6 ounces, no greater than 0.5 ounces, no greater than 0.4 ounces, no greater than 0.3 ounces, no greater than 0.2 ounces, no greater than 0.1 ounces, no greater than 0.09 ounces, no greater than 0.08 ounces, or no greater than 0.05 ounces.

It will be appreciated that the weight of the object 30 may be within a range including any one of the minimum and maximum values noted above, including, for example, but not limited to at least 0.001 ounces and not greater than 10 ounces, or within a range of at least 0.07 ounces and not greater than 0.9 ounces, or within a range of at least 0.002 ounces and not greater than 5 ounces, or within a range of at least 0.002 ounces and not greater than 1.5 ounces. In a non-limiting embodiment, other sizes, and weights of the object 30 can be used with the delivery device 20 to project the object 30 toward the target zone 50.

The weight of the object 30 can be adjusted for different training purposes and achieving various predetermined trajectories (e.g., 40, 42, 44). The weight can depend on the size and materials used for the specific object 30 that support different training processes. The variation of weight can result in speed changes of the object 30.

In a non-limiting embodiment, the shape of the object 30 can be substantially spherical. In another non-limiting embodiment, the object can be non-spherical, such as spheroidal. In another non-limiting embodiment, the object 30 can also have surface features (e.g., dimples, divots, holes, recesses, ridges, bumps, grainy textures, etc.) for trajectory modification. The shape of the object 30 can be tailored to emulate certain predetermined trajectories such as knuckle ball throws, kicks from a soccer ball, etc.

In a non-limiting embodiment, the materials that make up the object 30 can be acrylonitrile butadiene styrene, polylactic acid, calcium carbonate, paper, cotton, or foam, any poly-based plastics, or plastics in general, calcites, metal such as steel, lead, copper or aluminum, rubber, a plant-based material, or a fungus-based material. In a non-limiting embodiment, the object 30 can be coated with glow in the dark colors. This can be used in various training methods for vision training, such as segmenting training and strike zone training (described later).

In a non-limiting embodiment, the object 30 can be illuminated by ultraviolet lights such as black lights for isolated training processes for vision tracking. Being smaller than the regulation objects, the object 30 can be safer than regulation objects. A user may need to only wear safety glasses or a mask.

The delivery device 20 can be positioned at a distance L2 from a target zone 50 or trainee 8. In a non-limiting embodiment, the distance L2 can be at least 3 feet, at least 4 feet, at least 5 feet, at least 6 feet, at least 7 feet, at least 8 feet, at least 9 feet, at least 10 feet, at least 11 feet, at least 12 feet, at least 13 feet, at least 14 feet, at least 15 feet, at least 16 feet, at least 17 feet, at least 18 feet, at least 19 feet, at least 20 feet, at least 25 feet, at least 30 feet, at least 35 feet, or at least 40 feet.

In another non-limiting embodiment, the distance L2 can be no greater than 210 feet, no greater than 205 feet, no greater than 200 feet, no greater than 190 feet, no greater than 180 feet, no greater than 170 feet, no greater than 160 feet, no greater than 150 feet, no greater than 140 feet, no greater than 130 feet, no greater than 120 feet, no greater than 110 feet, no greater than 100 feet, no greater than 90 feet, no greater than 80 feet, no greater than 70 feet, no greater than 60 feet, no greater than 55 feet, no greater than 50 feet, no greater than 45 feet, no greater than 40 feet, no greater than 35 feet, no greater than 30 feet, no greater than 25 feet, or no greater than 20 feet.

It will be appreciated that the distance L2 may be within a range including any one of the minimum and maximum values noted above, including, for example, but not limited to at least 5 feet and not greater than 200 feet, or within a range of at least 5 feet and not greater than 55 feet, or within a range of at least 15 feet and not greater than 50 feet, or within a range of at least 15 feet and not greater than 40 feet, or within a range of at least 5 feet and not greater than 15 feet, or within a range of at least 10 feet and not greater than 25 feet.

However, farther distances are achievable with increased power projecting the object 30 toward the target zone 50. In a non-limiting embodiment, the target zone 50 can be a rectangle defined by a height L5 and a width L4 and can represent a relative position in space, or the target zone 50 can be a physical collection device that captures the objects 30 that enter individual target segments 76. The target can be moved up or down (arrows 68, FIG. 4) to position the target zone 50 at the desired height L3. An imaging sensor 32 can capture imagery of the trainee 8 and communicate the imagery to the controller 28, 29. In a non-limiting embodiment, the imaging sensor 32 can include a camera, a 2D camera, a 3D camera, a LiDAR sensor, a smartphone, a tablet, a laptop, or other video recorders.

The target zone 50 can be divided into a plurality of target segments 76 and the controller 28, 29 can initiate the projecting of the object 30 through a predetermined trajectory (e.g., trajectories 40, 42, 44) toward a specific target segment 76 or toward an area outside of the target zone 50 for various training methods. For example, as in baseball or softball training, in the beginning of a training session, the controller 28, 29 (via selections from a coach/trainer 4, the trainee 8 or another user) can deliver fast balls along the trajectory 42 that can arrive at the target zone 50 in the center target segment 76 (or any other appropriate segment 76). This can be used to help train the trainee 8 to recognize the object 30 and track it through the trajectory 42 through consistent training using the trajectory 42.

When scoring of this activity indicates that the trainee 8 has mastered tracking the object 30 through at least a portion of the trajectory 42, then other trajectories can be selected for additional training. These other trajectories can be designed by the trainee 8, the coach 4, other individual, or controller 28, 29 for the particular training method. These other trajectories can also be designed to mimic at least a portion of the trajectories of a sports object that was projected through one or more game trajectories in a real-life event by a real-life athlete. In this type of training, the trainee 8 can train like they are facing the real-life athlete that projected the sports object along the one or more game trajectories. The scoring can be determined via imagery captured by one or more imaging sensors or by a coach/trainer 4 visually observing the interaction of the trainee 8 with the object 30. The controller 28, 29 can analyze the imagery to determine the performance of the trainee 8 to the training goals or criteria for the training method being performed. The controller 28, 29 can then establish a score for the trainee 8, which can be used to provide feedback to the trainee 8, coach/trainer 4, or other user for improving the trainee's performance. The score can be compared to previous scores to identify trends in the trainee's performance.

For a fast ball simulation, the object 30 can be projected by the delivery device 20 along the trajectory 42. The object 30 can be seen traveling along the trajectory 42 as indicated by the object position 30". For other trajectories, such as 40, 44 (which can be more complex trajectories), the object 30 can be seen traveling along the trajectory 40, 44 as indicated by positions 30' and 30".

Figure 1D:
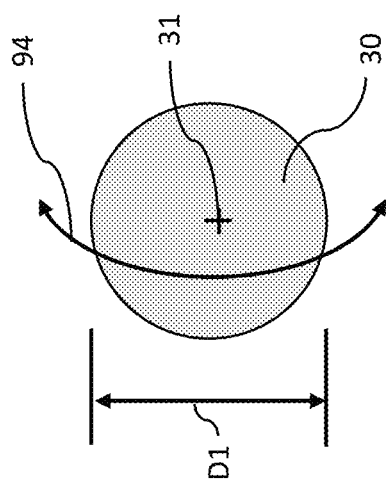

FIGS. 1D, 1E are representative side views of an example object 30 which can be of various shapes and sizes. In a non-limiting embodiment, the object 30 in FIG. 1D is shown to be a sphere with center axis 31 and diameter D1. The object 30, when projected by the delivery device 20, can have a spin 94 imparted to the object 30 by the delivery device 20. The spin 94 can be in any rotational direction around the axis 31. In another non-limiting embodiment, the object 30 in FIG. 1E is shown to be a spheroid with center axis 31 and diameter D1 that is the shortest diameter of the spheroid shape. The object 30, when projected by the delivery device 20, can have a spin 94 imparted to the object 30 by the delivery device 20. The spin 94 can be in any rotational direction around the axis 31. The spin 94 is shown to rotate the object 30 about the axis 31 similar to a spiral throw of a football. However, the spin 94 can also rotate the object 30 end over end about the axis 31 and any rotational direction in between.

In a non-limiting embodiment, the spin 94 can be "0" zero, at least 1 RPM, at least 2 RPMS, at least 3 RPMS, at least 4 RPMS, at least 5 RPMS, at least 10 RPMS, at least 20 RPMS, at least 50 RPMS, at least 100 RPMS, at least 200 RPMS, or at least 300 RPMS.

In a non-limiting embodiment, the spin 94 can be no greater than 120,000 RPMs, no greater than 116,000 RPMs, greater than 115,000 RPMs, no greater than 110,000 RPMs, no greater than 105,000 RPMs, no greater than 100,000 RPMs, no greater than 90,000 RPMs, no greater than 80,000 RPMs, no greater than 70,000 RPMs, no greater than 60,000 RPMs, no greater than 50,000 RPMs, no greater than 40,000 RPMs, no greater than 30,000 RPMs, no greater than 20,000 RPMs, no greater than 15,000 RPMs, no greater than 14,000 RPMs, no greater than 13,000 RPMs, no greater than 12,000 RPMs, no greater than 11,000 RPMs, no greater than 10,000 RPMs, no greater than 9,000 RPMs, no greater than 8,000 RPMs, no greater than 7,000 RPMs, no greater than 6,000 RPMs, or no greater than 5,000 RPMs.

It will be appreciated that the spin 94 of the object 30 may be within a range including any one of the minimum and maximum values noted above, including, for example, but not limited to at least "0" zero RPMs and not greater than 11,000 RPMs ounces, or within a range of at least 1 RPM and not greater than 116,000 RPMs, or within a range of at least 1 RPM and not greater than 115,000 RPMs, or within a range of at least 100 RPMs and not greater than 10,000 RPMs.

FIG. 2A is a representative functional diagram of a system 10 for training a trainee 8 to improve eye-hand coordination in various sports. This system is similar to the systems shown in FIGS. 1A-1C, except that an impact device is included at a distance L2 from the delivery device 20. The target zone 50 can be seen to be as a physical collection device that captures the projected objects 30 within the target segment 76 in which the object arrives at the target zone 50. The impact device 52 can have a platform 54 for mobility. The target zone 50 can be positioned on one side of the impact device 52 with a user impact zone 56 on an opposite side of the impact device 52. In this configuration, generally, after the trainee 8 has progressed from the training exercise of tracking the object 30 through the trajectories, the trainee 8 can use a regulation sports tool 12 (see FIGS. 1A-1C) to strike (or impact) the zone 56 preferably at the appropriate time that the object 30 is captured in the target zone 50.

The impact device 52 can include sensors 58 in the user impact zone 56 to detect when the regulation sports tool 12 impacts the impact zone 56. Sensors in the target zone 50 can determine the time when the object 30 arrived at the target zone 50 and possibly the position in the target zone 50 (e.g., which target segment 76). Comparing the time the sports tool 12 impacts the impact zone 56 and the time when the object 30 is detected at the target zone 50 can provide a scoring for the trainee 8 and encourage the trainee 8 to improve their performance of impacting the zone 56 at the appropriate time such that the trainee 8 would have contacted correctly with the object 30, or in real-game situations, a regulation object.

In a non-limiting embodiment, the impact device 52 can comprise a support structure with a target zone 50 on one side and an impact zone 56 on an opposite side, with the target zone 50 comprising sensors 51 to detect reception time and position of the projected object 30, and the impact zone comprising sensors 58 to detect reception time and position of an impact of a sports tool 12 wielded by the trainee 8. The impact zone 56 can also comprise several other types of impact material for receiving an impact from the sports tool 12 wielded by the trainee 8. In a non-limiting embodiment, the impact material can be a padded (or weighted) panel as shown in FIG. 2A, a padded (or weighted) bag as shown in FIG. 3A, an object (such as a puck, a ball, a bag, etc.) perched on a structure as shown in FIG. 3B, a suspended object (such as a puck, a ball, a bag, etc.) as shown in FIG. 3C, a net in tension as shown in FIG. 3D, or a rope or resistance band in tension as shown in FIG. 3E.

Any of these impact devices 52 can be used in one or more training methods that project an object 30 along a predetermined trajectory toward a target zone 50 of the impact device 52. In a non-limiting embodiment, the trainee 8 attempts to strike the impact zone 56 with a sports tool 12 at an appropriate time and location compared to a time when and a location where the object is received at the target zone 50. The controller 28, 29 can collect data from the sensors 51, 58 and score the trainee 8 based on the trainee's performance at striking the impact zone 56 at the appropriate time and location with the sports tool 12 compared to the time and location the object 30 is received at the target zone 50.

Training with the impact device 52 can use the delivery device 20 to project the object 30 toward the target zone 50 while allowing the trainee 8 to strike the impact zone 56 with a regulation sports tool 12. This allows the trainee 8 to work on not only eye-hand coordination using the delivery device 20, but also work on body motion mechanics (e.g., swing mechanics in baseball or softball) using the regulation sports tool 12 (e.g., a regulation bat for baseball or softball, a regulation racket for tennis, a regulation stick for hockey, etc.).

In a non-limiting embodiment, the controller 28, 29 can communicate the performance score to the trainee 8 and the trainee 8 can use the performance score to know that they need to adjust their performance or that the trainee's performance is acceptable. In a non-limiting embodiment, the score can also be used to indicate that adjustments can be made to the delivery device 20 to project objects 30 along various trajectories to focus on weaknesses of the trainee 8 or improve strengths of the trainee 8. After the trainee 8, coach/trainer 4, another individual, or controller 28, 29 adjusts the delivery device 20 based on the score, the delivery device 20 can then project a subsequent object 30 along another trajectory toward the impact device 52. This process of projecting an object 30 toward the impact device 52, the trainee 8 striking the impact device 52, the controller 28, 29 scoring the trainee's performance, and adjusting the delivery device 20 based on the scoring to deliver one or more subsequent objects 30 that can continue as desired to continue the impact device training.

In a non-limiting embodiment, the sensors 51 can comprise one or more imaging sensors 32 that can capture imagery of the object 30 as it travels along the trajectory (e.g., 40, 42, 44). The imagery can be analyzed by the controller 28, 29 to determine the arrival time and arrival location of the object 30 at the target zone 50. In a non-limiting embodiment, the sensors 58 can comprise one or more imaging sensors 32 that can capture imagery of the sports tool 12 as it strikes the impact zone 56. The imagery can be analyzed by the controller 28, 29 to determine the arrival time and arrival location of the sports tool 12 at the impact zone 56. The controller 28, 29 can compare the arrival time and arrival location of the object 30 and the arrival time and arrival location of the sports tool 12 to determine the accuracy of when and where the sports tool 12 struck the impact zone 56 and establish the performance score of the trainee 8 that indicates how well the trainee 8 interacted with the object 30.

In another non-limiting embodiment, the sensors 58 can comprise one or more strain sensors that can detect a force of impact when the sports tool 12 strikes the impact zone 56. This force information can be communicated to the controller 28, 29, which can determine an estimated trajectory of a regulation object if the sports tool 12 had impacted the regulation object.

FIG. 2B is a representative functional diagram of a system 10 for training a trainee 8 to improve eye-hand coordination in various real-life events (e.g., sports events, training events, tactical situations, etc.). This system is similar to the systems shown in FIGS. 1A-1C, with an imaging sensor that can monitor, capture, or record the interaction of the trainee 8 with an object 30 delivered from the delivery device 20 to the target zone 50. The target zone 50 can be seen as a spatial representation of the area in which the trainee 8 wishes to impact the object 30 with a sports tool 12. The imaginary target zone 50 can be at a distance L2 from the exit of the delivery device 20.

For training method 114, the delivery device 20 can be configured by the controller 28, 29 to deliver an object 30 along a predetermined trajectory (e.g., 40, 42. 44) to the target zone 50. The predetermined trajectory can direct the object 30 to one of the multiple target segments 76 in the target zone or outside the target zone 50 (if desired). The trainee 8 can be in a position to swing a sports tool 12 at the object as it arrives at the target zone 50. In a particular embodiment, the sports tool 12 can be a specialized tool for training purposes. For example, the sports tool 12 can be a significantly smaller diameter bat to require increased precision on the part of the trainee 8 to correctly hit the object 30 proximate the target zone 50. However, using a smaller sports tool 12 can minimize swing mechanics training but can be beneficial to train more precise control over the position of the sports tool 12. The trainee 8 or coach/trainer 4 or controller 28, 29 can score the trainee's performance and rate it as being better, worse, or the same. The trainee 8 (or coach/trainer 4 or controller 28, 29) can then select the next object and trajectory for the trainee's next attempt at hitting the object 30 as it arrives at or substantially at the target zone 50. The process can be repeated as often as needed for the trainee 8 to achieve the desired performance level of hitting the object 30 when the object is being received at the target zone.

An imaging sensor 32 can capture imagery of the object 30 traveling along the predetermined trajectory (e.g., 40, 42, 44), the ability of the trainee 8 to track the object along the trajectory with their eyes, and the reaction time and motion of the trainee 8 as they swing at the object 30. The imagery can be used by the controller 28, 29, the coach/trainer 4, or the trainee 8 to assess the trainee's performance and determine a score that indicates a variance from a desired performance. Any scoring described in this disclosure can be used to track over time progress (of lack thereof) of the trainee 8 as the trainee 8 progresses through the training methods. Any scoring described in this disclosure can be used to identify weaknesses or strengths in the trainee 8, and the delivery device 20 can automatically adjust (or be manually adjusted via user input) its parameters to focus on these weaknesses or strengths. The scoring can also be compared between any of the training methods described in this disclosure to determine an overall performance score for the trainee 8. Correlating or analyzing the scoring of the trainee in various training methods can identify additional points of weakness or strength that a single training method may not so easily identify.

This method 114 can be different than the method 112 in that method 112 can focus on swing mechanics of the trainee 8 while using a standard regulation sports tool 12 to impact the impact device at substantially the same time as the object arriving at the target zone. However, the training method 114 can focus on the hand-eye coordination required to contact an object (that is smaller than the regulation objects) with a sport tool 12 (e.g., can be a specialized sports tool 12 that is smaller than a regulation sports tool for that sport). By training with the smaller devices, the trainee 8 can be more precise when using a regulation sports tool 12 to impact a regulation object.

Figure 4:
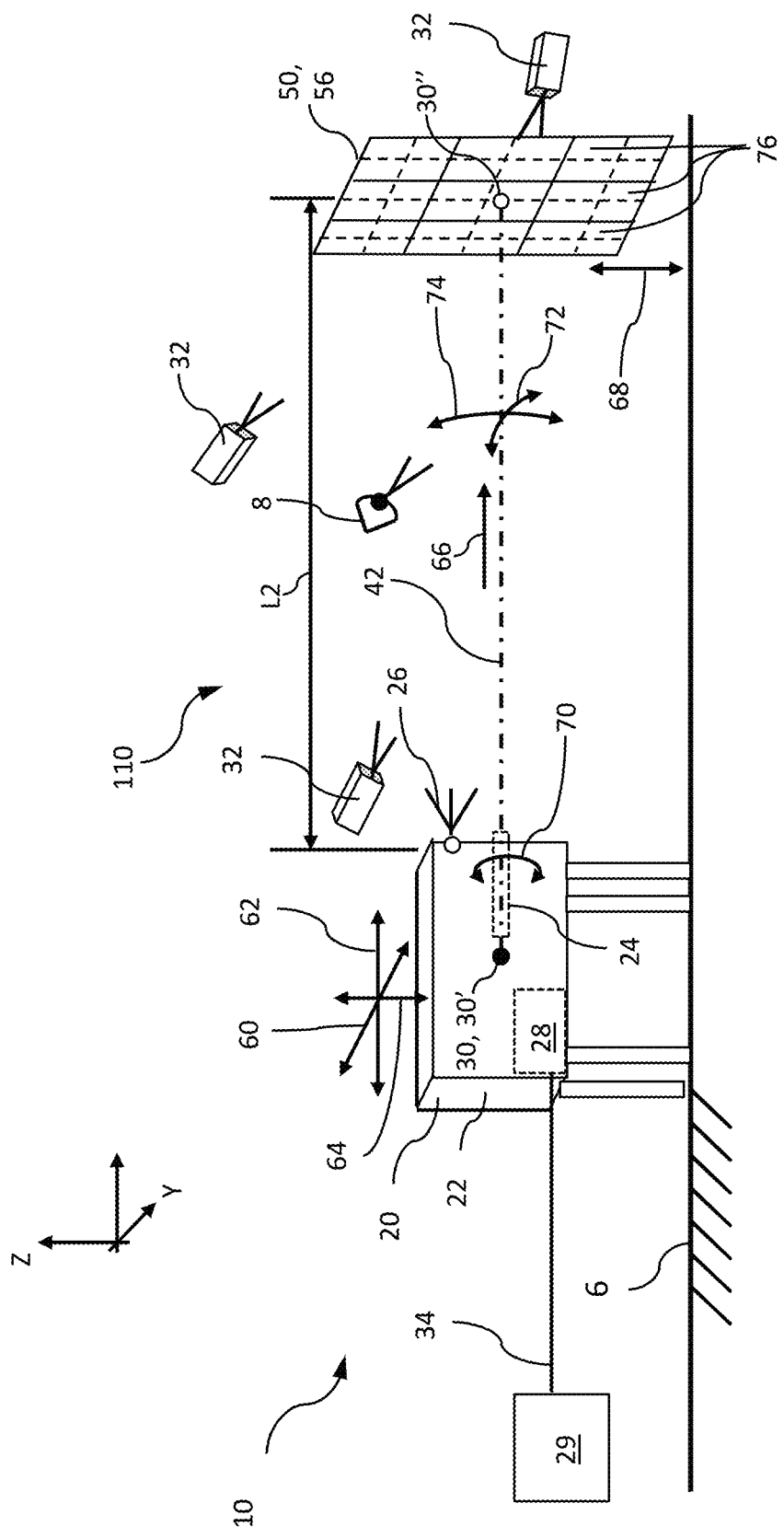
FIG. 4 includes a representative functional diagram of a system and method for training a trainee to improve coordination, vision training, and/or tracking capabilities, in accordance with certain embodiments.

FIG. 4 is a representative functional diagram of a system 10 for training a trainee 8 to improve eye-hand coordination in various sports. The delivery device 20 can be adjusted in various ways to facilitate projecting the object 30 along a predetermined trajectory 40, 42, 44 toward a target zone positioned at a distance L2 from the delivery device 20. Distance L2 can be at least 5 feet, or at least 10 feet, or at least 15 feet, or at least 20 feet, or at least 25 feet, or at least 30 feet, or at least 35 feet, or at least 40 feet, or at least 45 feet, or at least 50 feet, at least 55 feet, or at least 75 feet, or up to 100 feet.

One or more imaging sensors 32 can be used to capture and record the travel of the object 30 along a predetermined trajectory (e.g., 40, 42, 44). The imaging sensors 32 can be placed at any position around the system 10 with at least three possible positions indicated in FIG. 4. Users (e.g., a coach 4, trainer 4, trainee 8, individual 8, or others) can also track the object along the predetermined trajectory and score the repeatability of the object 30 to travel along the predetermined trajectory. The imaging sensors 32 can capture and record how the eyes of the trainee 8 track the object 30 along the predetermined trajectory. Imagery collected via the imagery sensors 32 can be analyzed by a local controller 28 or a remotely located controller 29 to determine how the trainee 8 tracks the object 30 along a predetermined trajectory and the controller(s) 28, 29 can score the ability of the trainee 8 to track the object 30 along a predetermined trajectory. The score can be used to improve the capability of the trainee to track the object 30, adjust the delivery device 20, or select subsequent trajectories of another object 30 (such as when the trainee 8 performs well enough to progress to a more difficult trajectory).

In a non-limiting embodiment, the imaging sensors 32 can also capture and record how other portions of a body of a trainee moves while the trainee is tracking the object 30. For example, the imaging sensors 32 can collect imagery of head movement as the trainee 8 tracks the object along the predetermined trajectory (e.g., 40, 42, 44). Scoring can indicate how well the trainee minimizes head movement during the object tracking. The imagery can also be used by the controller 28, 29 to determine if another portion of the body moves correctly or incorrectly. For example, arm movement, hip rotation, shoulder movement, etc., can be analyzed as the trainee 8 tracks the object 30 toward the target zone 50, such as in preparation for maneuvering the sports tool 12. The controller(s) 28, 29 can score the body motion to provide positive or negative feedback to the trainee 8 so they can improve their body control. The controllers 28, 29 can also analyze the imagery to calibrate the delivery device 20, similar to sighting in a rifle on a rifle range. By recording the trajectory traveled by the object 30, the controllers can indicate if the actual trajectory correctly correlates to the desired (or predetermined, expected) trajectory.

The delivery device 20 can include a guide 24 that is used to change the exit angle A1 and rotation of the object 30 as it leaves the delivery device 20. In a non-limiting embodiment, the guide 24 can be tilted in any direction including horizontal arc length (arrows 72) and vertical arc lengths (arrows 74) to allow the guide to point the object at any angle within a cone-shaped region with the end of the cone at the exit point of the object 30 and expanding in diameter as the distance from the delivery device 20 increases. The guide 24 can also vary an amount of spin (i.e., varied RPMs) on the object 30 as well as a direction of the rotation of the spin relative to the delivery device 20 by rotation (arrows 70) of the guide 24. The guide 24 can also vary an interference of the object 30 with a friction device to impart various spin rates (RPMs) of the object 30. The controller 28, 29 can control the speed at which the object 30 is projected from the delivery device 20. In a non-limiting embodiment, with this degree of control, the object 30 can be tailored to reproduce substantially any desired trajectory, where the desired trajectory can be the trajectory of a baseball pitch, a softball pitch, a soccer kick, a hockey player shot on goal with a puck, a football pass, a cricket pitch, a lacrosse throw, a tennis volley, a skeet delivery for shooting sports, as well as many other regulation objects in other sports or real-life events.

FIG. 4 can also represent a method 110 for recognition training. This method can be referred to as tracking: Strike Path Recognition training and is generally applicable to baseball or possibly softball. It should be understood that this type of training can also be used for other sports training, such as emulating straight shots at the goal in hockey, center shots on goal for soccer, etc. The method uses the repetitive projection of the object 30 along a single predetermined trajectory so the trainee can train their vision and brain to focus on the smaller object 30 and recognize its trajectory faster than before training. A purpose of this method 110 can be to improve a trainee's ability to recognize a strike path of the object 30. The controller 28, 29 can begin the method 110 by throwing Dead Red (Center of Strike Zone) fastballs so the trainee 8 can recognize and develop their vision and brains to recognize the path of a strike-through successive repetition of the objects 30 traveling the predetermined trajectory 42 that can emulate a fast ball down the middle of home plate. It should be understood that the fast ball trajectory can be aimed at any location on the target zone 50, which in this example can represent a strike zone.

The quicker the trainee's brain recognizes a fast ball strike, the better chance the trainee has to connect with the fast ball and get a hit. Training with the object 30, which is much smaller than a baseball, can train the trainee's vision and brain to process the trajectory information quicker and more quickly determine a ball or strike trajectory. Strike Path Recognition of Dead Red pitches can be important because these may be the best pitches to hit for average and distance. It should be understood that the delivery device 20 can be programmed to throw both strikes and balls, but it may be preferable to throw a clear majority of pitches to be strikes. Therefore, the training can improve the ability of the trainee's vision and brain to see the path of the strikes. The method 110 (i.e., Strike Path Recognition training method)

can train the trainee 8 to know and more quickly recognize the more optimum trajectories that may yield more favorable results.

If the trainee 8 knows a strike path trajectory very well, then a trajectory outside the Strike Zone Path should appear odd, different, and not right, and allow the trainee 8 to recognize these trajectories faster and enable a faster decision by the trainee 8 to disregard an object traveling along the odd trajectory. It may be desirable to project objects 30 along only a "Strike Path" trajectory and limit trajectories that are delivered outside the target zone 50 to only certain conditions such as when specifically requested by the trainee 8 or a coach 4 or another other person or controller 28, 29. The controller 28, 29 can be programmed to project an object 30 along an "outside target zone" trajectory during a sequence of predetermined trajectories (such as a sequence of pitches, a sequence of volleys, a sequence of throws, etc.). The importance of improved Strike Path Recognition can be manifested in a trainee 8 getting ahead in a strike/ball count, which is a more favorable position to be in when facing a pitcher in baseball. Batters in favorable counts tend to hit much higher averages (100 pts higher) than batters who get into an unfavorable count.

The method 110 can include operations of powering up the system 10, verifying the correct objects 30 and the correct number of objects 30 are installed in the delivery device 20, adjusting the speed to deliver an appropriate speed of the objects 30 according to the desired training, via a human machine interface selecting the training protocols for throwing Dead Red Fastballs, stepping up to the target zone of the system 10, and initiating delivery of the object 30 along a predetermined trajectory. In a non-limiting embodiment, the human machine interface (HMI) can be a graphical user interface GUI, a touch screen, mechanical interface panel switches, a button, a stride sensor, signal generator that creates and sends a signal via wired or wireless communications to the controller 28, 29, or an audio sensor to detect audio signals (such as voice commands) that can be recognized by the controller 28, 29, etc. In a non-limiting embodiment, the HMI device input can be a sensor reading, imaging sensors, hand-held computer system interface, hand-held motion sensors, motion sensors, light pointer, touch screen input, audible signal, trigger, key stroke entry, mouse click, or combinations thereof. The controller 28, 29 can read a file record from a controller's non-transitory storage medium that contains the desired parameters for the delivery device 20 to project an object along the predetermined trajectory. The controller 28, 29 can command the delivery device 20 to move an object to a start location, and the controller 28, 29 can then command the delivery device 20 to project the object 30 along the predetermined trajectory to the target zone 50. The delivery device 20 can be commanded by the controller 28, 29 to repeat reading the file record, setting up the delivery device 20, and projecting the object 30 along the predetermined trajectory for delivering as many objects 30 to the target zone as desired.

The trainee 8 located proximate to the target zone focuses on and tracks the object 30 along at least a portion of the predetermined trajectory 42 with the trainee 8 attempting to keep a direct line of sight to the object 30 and remain focused on the object 30 as it travels along at least a portion of the predetermined trajectory 42.

The controller 28, 29 (or coach 4, or trainee 8) can analyze the performance of the trainee 8 and offer feedback of the trainee's performance by providing, to the trainee 8, a score of their performance which can be determined by the controller 28, 29 (or coach, trainer 4, trainee 8) via analysis of captured imagery from the imaging sensors 32 or other feedback instrumentation (e.g., sensors 51, 58, 32 of the impact device 52).

Referring again to FIG. 2A, the configuration of the system 10 with the impact device 52 at the target zone 50 can be used for a training method 112 which can be referred to as swing mechanics training. In a non-limiting embodiment, the method 112 can also be easily adapted to provide swing mechanics training for other sports such as cricket, tennis, table tennis, soccer, or any sport that requires impact with a moving object. Generally, after the trainee 8 scores at a sufficient level in the method 110 (Strike Path Recognition method), then the coach/trainer 4 or trainee 8 or controller 28, 29 can initiate the training method 112 (Swing Mechanics Training method 112). Training method 112 allows a trainee 8 to take a full swing at the object 30 while maintaining proper swing mechanics.

In a non-limiting embodiment, the training method 112 can include the impact device 52 so a trainee 8 can take a full swing at the object 30 while impacting the impact device 52. The method 112 promotes the trainee's balance and allows the coach/trainer 4 (and possibly the controller 28,29) to examine the true swing mechanics of the trainee 8 from initial hand load, thru a swing including the point of contact of the impact device 52 with a sports tool 12 and including swing follow-thru.

The impact device 52 can include a weighted panel as shown in FIG. 2A (or weighted bag as shown in FIG. 3A), with the size and weight of the panel tailored for the size and strength of the trainee 8. The weighted panel can include a soft inner core surrounded by three layers of various materials, to protect the soft inner core from impacts of the sports tool 12 and to minimize effects to the trainee of the impact of the sports tool 12 on the impact device 52. The weighted panel can be any shape, such as cylindrical, square, rectangular, polygonal, etc. As stated above, an impact zone 56 can be attached to one side of the impact device 52 with the target zone positioned on an opposite side of the impact device 52. The target zone 50 can be configured to capture the objects 30 as they impact individual target segments 76 in the target zone 50.

The impact device 52 can be attached to a mobile platform 54, which can represent home plate in baseball or softball or a goalie position in hockey. The platform 54 and the impact device 52 are designed so that the impact device 52 does not move when impacted by the sports tool 12. The impact zone is designed to absorb substantially all the energy delivered by the sports tool 12. The mobile platform 54 allows for easy placement and removal of the impact device 52 to accommodate other training methods (such as Strike Path Recognition training) that do not need the impact device 52.

With the trainee 8 positioned proximate the impact device 52 in an appropriate position to deliver an impact to the impact zone 56 and swing or manipulate the sports tool 12 as the trainee 8 would normally in a game situation, the delivery device 20 can then be commanded to project an object 30 along a predetermined trajectory toward a target segment 76 of the target zone 50 or outside the target zone 50. The trainee 8 can then attempt to track the projected object 30 along at least a portion of the predetermined trajectory. The trainee 8 can then swing the sports tool 12 in an attempt to hit the impact zone 56 at the appropriate time compared to when the object 30 is being received at the target segment 76. The appropriate time refers to the time of the impact of the sport tool 12 with the impact zone 56 that would have resulted in a correct time of impact with the object 30 if the object 30 were allowed to continue along the predetermined trajectory as if the impact device 52 were not there. The impact zone 56 can include sensors 58 that sense when the sports tool 12 impacts the impact zone 56 and can send the sensor data to the controller 28, 29 to log the time of the impact. The sensors 58 can also be positioned to detect a location of the impact of the sports tool 12 in the impact zone 56. Therefore, the sensor data supplied to the controller 28, 29 can include both a time stamp and a location of the impact in the impact zone. The sensors 58 may also be configured to detect a force of the impact so the controller 28, 29 can calculate how much force would have been applied and where it would have been applied to a regulation object.

The target zone 50 can also include sensors 51 that can sense when the object impacts a target segment 76 and when the sensor(s) from the target segment 76 communicates the detection (sends sensor data) to the controller 28,29, then the controller 28, 29 would know which segment 76 received the object since the controller 28, 29 knows which sensors are in which segments 76. Therefore, with the knowledge of where and when the object impacted the target zone 50 and the knowledge of where, when, and how much force is applied to the impact zone 56, the controller 28, 29 can calculate a score of the trainee's attempt to impact the impact zone at the appropriate time and position and provide that score to the trainee 8, the trainer 4, the coach 4, or others to assist the trainee 8 in improving his performance.

The method 112 can include the operations of powering up the system 10, verifying correct objects 30 and correct amount of objects 30 are installed in the delivery device 20, adjusting the speed to deliver the appropriate speed of the objects 30 according to the desired training, via a human machine interface selecting the training protocols for projecting objects 30 one at a time along one or more predetermined trajectories, stepping up to the target zone of the system 10, and initiating delivery of the object 30 along a predetermined trajectory. In a non-limiting embodiment, the human machine interface can be a graphical user interface GUI, a touch screen, a mechanical interface panel switches, a button, a stride sensor, voice commands recognized by the controller 28, 29, commands via remote control or wireless communications to the controller 28, 29, etc. The controller 28, 29 can read a file record from a controller's non-transitory storage medium that contains the desired parameters for the delivery device 20 to project an object along a predetermined trajectory. The controller 28, 29 can command the delivery device 20 to move an object to a start location, and the controller 28, 29 can then command the delivery device 20 to project the object 30 along the predetermined trajectory to the target zone 50. After each projection of the object 30, the coach/trainer 4 can score the trainee's performance and provide the score and any additional feedback to the trainee 8 to help the trainee 8 improve their timing, power, placement, and swing mechanics to improve their performance. The delivery device 20 can be commanded by the controller 28, 29 to repeat reading the file record, setting up the delivery device 20, and projecting the object 30 along the predetermined trajectory for delivering as many objects 30 to the target zone as desired, and the coach/trainer 4 can provide scoring and feedback as needed to assist the trainee 8 to improve performance.

The trainee 8 located proximate to the target zone focuses on and tracks the object 30 along at least a portion of the predetermined trajectory with the trainee 8 keeping a direct line of sight to the object 30 and remaining focused on the object 30 as it travels along the predetermined trajectory. The trainee 8 then attempts to hit the object 30 by swinging the sports tool 12 (e.g., a baseball bat) toward the object 30. The training method trains the trainee to focus on the object 30 as it travels to the target zone and strikes the impact zone 56 at the same time when the object 30 impacts the target zone 50. Variations between the time the sports tool 12 strikes the impact device 52 and when the object 30 strikes the target zone 50 can be scored with higher scores representing smaller variations in time between the two strikes (or impacts). The power of the impact of the sports tool 12 on the impact zone 56 and the location of the impact in the impact zone 56 can also be used to determine a score that indicates how close the trainee was to hitting the desired location with the desired amount of power.

The controller 28, 29 (or coach 4) can analyze the performance of the trainee 8 and offer feedback of the trainee's performance by providing, to the trainee 8, a score of their performance which can be determined by the controller 28, 29 (or coach, trainer 4) via analysis of captured imagery from the imaging sensors or other feedback instrumentation (e.g., sensors in the impact device 52).

Figure 5:
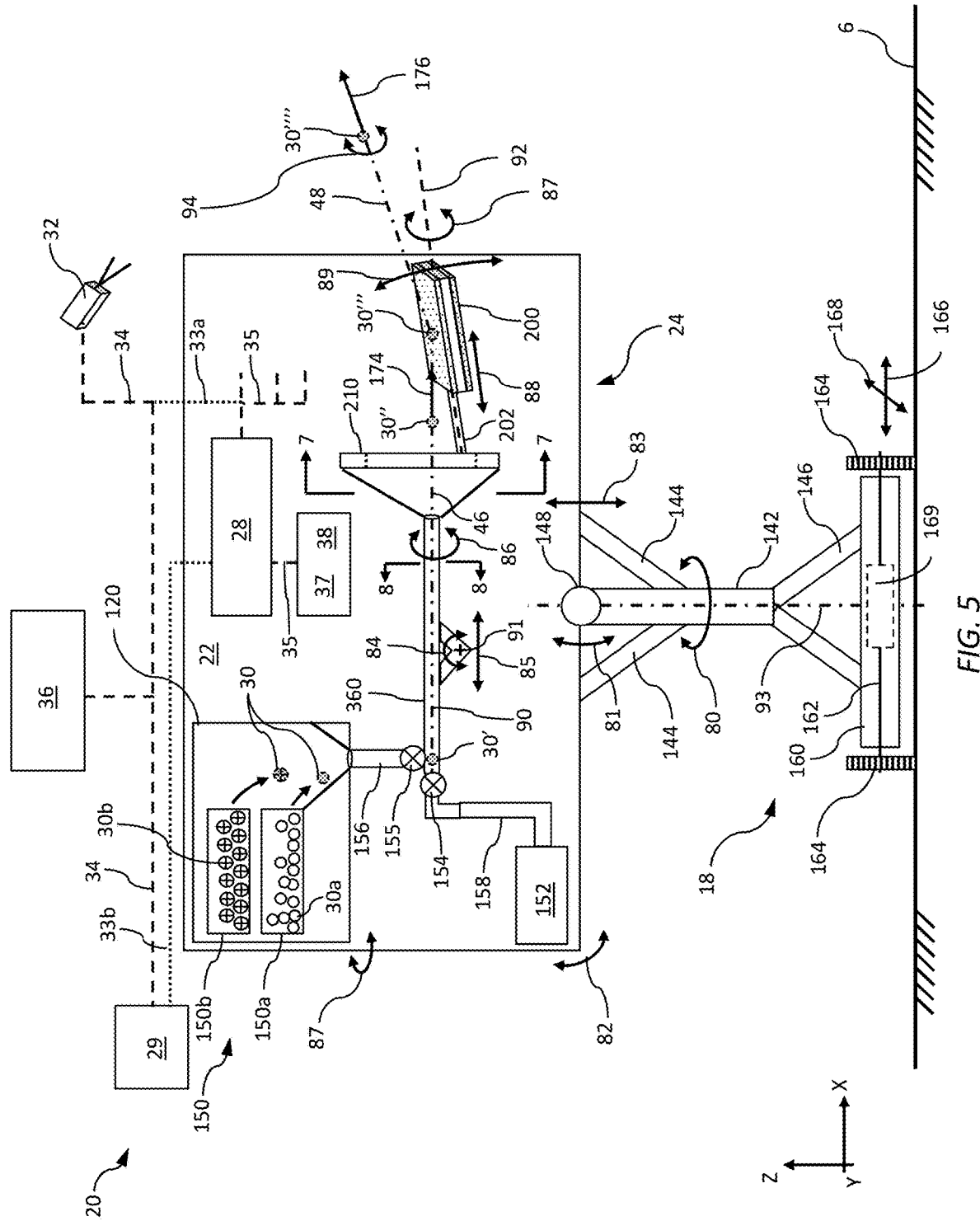
FIG. 5 is a representative functional block diagram of an object delivery device that can support the systems and methods of the current disclosure, in accordance with certain embodiments.
Figure 9:
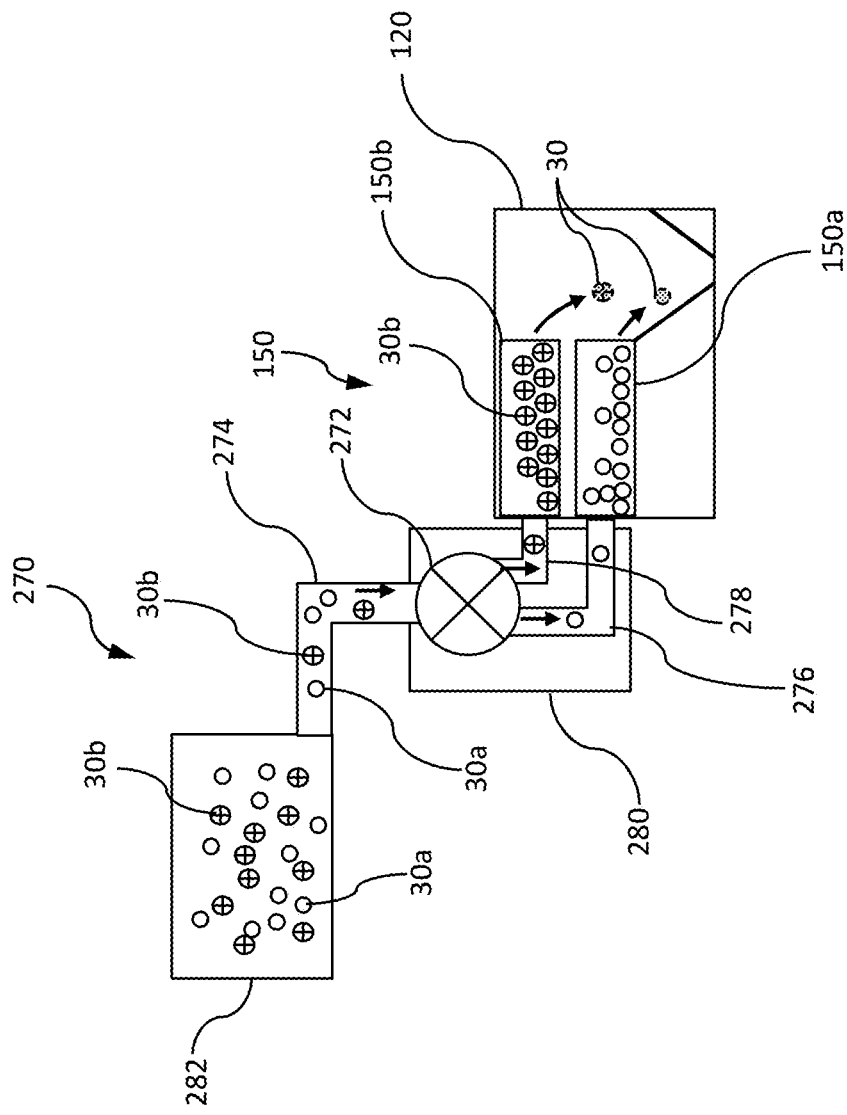
FIG. 9 is a representative functional block diagram of an object sorter for a delivery device that can support the systems and methods of the current disclosure, in accordance with certain embodiments.

FIG. 5 is a representative functional block diagram of an object 30 delivery device 20 that can support the systems and methods of the current disclosure, as well as other systems and methods. The delivery device 20 can include a chassis 22 adjustably mounted to a base 18 that can move the delivery device 20 along a surface 6 in directions 166, 168. The delivery device 20 can include one or more local controllers 28 (referred to as controller 28) that can be communicatively coupled to components within the delivery device 20 via a network 35 as well as communicatively coupled to one or more remote controllers 29, one or more imaging sensors 32, and one or more external databases 36 via one or more networks 33a, 33b, 34. In some network configurations, the network 35 can include one or more internal networks 35 for communicating to components of the delivery device 20. The controller 28 can be communicatively coupled to a non-transitory memory 37 that can store a delivery device parameter database 38. Sets of delivery device parameters can be stored in the database 38, where each set can be used to configure, via the controller 28, 29, the delivery device 20 to deliver an object 30 along a respective predetermined trajectory. These internal networks 35 can include networks with standard or custom network protocols to transfer data and commands to/from the delivery device 20 components.

The one or more remote controllers 29 (referred to as controller 29) can be communicatively coupled to the local controller 28 via a network 33a that communicatively couples the external network 34 to the internal network 35 (with network 33b not connected). In this configuration, the remote controller 29 can command and control the delivery device 20 components directly without the direct intervention of the local controller 28. However, in a preferred embodiment, the controller 29 can be communicatively coupled to the controller 28 via the network 33b, which is not directly coupled to the network 34 (with network 33a not connected). In this configuration, the controller 29 can communicate configuration changes (or other commands and data) for the delivery device 20 to the controller 28, which can then carry out these changes to the components of the delivery device 20. If should be understood, in another configuration, the networks 33a, 33b, 34, 35 can all be connected with the controllers 28, 29 managing the communications over the networks.

In a non-limiting embodiment, the delivery device 20 can include a guide 24 that can modify the trajectory and spin of the object 30 as the object 30 is projected toward the target zone 50 or trainee 8. The guide 24 can include a barrel 360 with a center axis 90 through which the object 30 can be projected toward a friction device 200. The friction device 200 can have a center axis 92 and can be rotated about the center axis 92 to alter the engagement of the object 30 when it impacts the friction device 200 at position 30". An object 30 can be received from the object storage area 120 and located at position 30' in a first end of the barrel 360. A pressurized air source 152 can be fluidically coupled to the first end of the barrel 360 via conduit 158, with the delivery of a volume of pressurized air controlled by a valve 154. The valve 154 and the air source 152 can be controlled by the controller 28, 29 to adjust the air pressure applied to the object 30 at position 30' as well as the volume of air applied. It should be understood that pressurized air is only one possible option for delivering a desired force to the object 30 to project the object 30 through the barrel 360. Pneumatics other than pressurized air can be used as well as hydraulics, electrical, electro-mechanical, or mechanical power sources that can supply the desired force to the object 30 to project the object 30 through the barrel 360.

In a non-limiting embodiment, an air pressure can be at least 3 PSI (i.e., pressure per square inch), at least 4 PSI, at least 5 PSI, at least 6 PSI, at least 7 PSI, at least 8 PSI, at least 9 PSI, at least 10 PSI, at least 20 PSI, at least 30 PSI, at least 40 PSI, at least 50 PSI, at least 60 PSI, at least 70 PSI, at least 80 PSI, at least 90 PSI, at least 100 PSI.

In another non-limiting embodiment, the air pressure can be no greater than 220 PSI, no greater than 210 PSI, no greater than 200 PSI, no greater than 190 PSI, no greater than 180 PSI, no greater than 170 PSI, no greater than 160 PSI, no greater than 150 PSI, no greater than 140 PSI, no greater than 130 PSI, no greater than 120 PSI, no greater than 110 PSI, no greater than 100 PSI, or no greater than 90 PSI.

It will be appreciated that the air pressure may be within a range including any one of the minimum and maximum values noted above, including for example, but not limited to at least 5 PSI and not greater than 220 PSI inches, or within a range of at least 5 PSI and not greater than 200 PSI, or within a range of at least 10 PSI and not greater than 200 PSI, or within a range of at least 5 PSI and not greater than 180 PSI.

In a non-limiting embodiment, a length of the barrel 360 can be at least 2 inches, at least 3 inches, at least 4 inches, at least 4.5 inches, at least 5 inches, at least 5.5 inches, at least 6 inches, at least 7 inches, at least 8 inches, at least 9 inches, at least 10 inches, at least 11 inches, or at least 12 inches.

In another non-limiting embodiment, the length of the barrel 360 can be no greater than 48 inches, no greater than 36 inches, no greater than 24 inches, no greater than 23 inches, no greater than 22 inches, no greater than 21 inches, no greater than 20 inches, no greater than 19 inches, no greater than 18 inches, no greater than 17 inches, no greater than 16 inches, no greater than 15 inches, no greater than 14 inches, no greater than 13 inches, no greater than 12 inches, no greater than 11 inches, no greater than 10 inches, no greater than 9 inches, no greater than 8 inches, no greater than 7 inches, no greater than 6 inches, no greater than 5.5 inches.

It will be appreciated that the length of the barrel 360 may be within a range including any one of the minimum and maximum values noted above, including, for example, but not limited to at least 2 inches and not greater than 48 inches, or within a range of at least 4.5 inches and not greater than 24 inches, or within a range of at least 4.5 inches and not greater than 5.5 inches, or within a range of at least 3 inches and not greater than 12 inches.

When the valve 154 is actuated, a controlled volume of pressurized air (or other pressurized gas) can be delivered to the first end of the barrel 360 for a predetermined length of time to force the object 30 to be propelled through the barrel 360 at a predetermined velocity, such that at position 30" the object 30 achieves a desired velocity vector 174. The velocity vector 174 can range from 25 miles per hour to 135 miles per hour. If the friction device 200 is not in a position to interfere with the trajectory 46 of the object 30 as it is propelled from a second end of the barrel 360, then the object 30 may continue along trajectory 46 and exit the delivery device 20 without having additional spin or deflection imparted to the object 30 by the friction device 200. This may be used for delivering "fast balls" along the predetermined trajectory 42 since the object does not engage the friction device 200 before it exits the delivery device 20.

However, if the friction device 200 is positioned to interfere with the object 30 as it is propelled from the second end of the barrel 360, then object 30 can engage (or impact) the friction device 200 at position 30''', thereby deflecting the object 30 from the axis 90 of the barrel 360 at an angle and imparting a spin 94 to the object. Impacting the friction device 200 can cause the object 30 to begin traveling along a predetermined trajectory 40 with an altered velocity vector 176 at position 30''''. The amount of spin 94 and the amount of deflection from trajectory 46 to trajectory 48 can be determined by the velocity vector 174 of the object 30 at position 30", the spin of the object 30 at position 30", the azimuthal position of the friction device 200 about its center axis 92, the azimuthal position of the friction device 200 about the center axis 90 of the barrel 360, the incline (arrows 89) of the friction device 200 relative to the center axis 90, the length (arrows 88) of the friction device 200, and the surface material on the friction device 200. The object 30 can then continue along the predetermined trajectory 48 to the target zone 50 or toward the trainee 8.

If another trajectory is desired, then the controller 28, 29 can modify the parameters of the delivery device 20 (such as changing the velocity vector 174 and spin of the object 30 at position 30", changing the azimuthal position of the friction device 200 about its center axis 92, changing the azimuthal position of the friction device 200 about the center axis 90 of the barrel 360, changing the incline (arrows 89) of the friction device 200 relative to the center axis 90, changing the length (arrows 88) of the friction device 200, or changing the surface material on the friction device 200) to deliver a subsequent object 30 along a new predetermined trajectory 48.

In a non-limiting embodiment, in addition to these parameters mentioned above, there are also parameters of the barrel position and delivery device 20 chassis 22 position that can be used to alter a trajectory of an object 30 to travel along a predetermined trajectory (e.g., 40, 42, 44) to a target zone (or trainee 8). Some of these parameters affect the orientation of the barrel 360 within the delivery device 20, while others can affect the orientation and position of the chassis 22 of the delivery device 20 relative to a surface 6, while others affect selecting an object 30 to be propelled from the barrel 360. In a non-limiting embodiment, all these parameters can have an impact on the trajectory of the object 30 as it is projected from the delivery device 20 toward the target zone 50 or trainee 8.

The barrel 360 can be rotated (arrows 86) about its center axis 90. This can be beneficial if the barrel 360 includes a non-smooth inner surface, such as an internal bore of the barrel 360 with rifling grooves (i.e., a surface with helically oriented ridges or grooves along the internal bore of the barrel 360) that can impart a spin (clockwise or counter-clockwise) to the object 30 as the object 30 travels through the internal bore of the barrel 360. Other surface features can also be used on the internal bore of the barrel 360 to affect the spin of the object 30 as it travels through the barrel 360.

The barrel 360 can be rotated (arrows 84) about the axis 91 to adjust the direction of the object 30 as it exits the barrel 360. The barrel 360 can also be moved (arrows 85) to adjust a distance between the exit end of the barrel 360 and the friction device 200.

The friction device 200 can be coupled to a structure (e.g., structure 210 via support 202) that can be used to rotate the friction device 200 about the center axis 90 of the barrel 360. This can be used to change the deflection angle imparted to the object 30 when it impacts the friction device 200 at position 30'''.

The chassis 22 can be rotationally mounted to a base 18 at pivot point 148. Actuators 144 can be used to rotate the chassis 22 about the X-axis (arrows 81) or the Y-axis (arrows 82) relative to the surface 6 by extending/retracting. There can be four actuators 144 positioned circumferentially about the center axis 93. The base 18 can rotate the chassis 22 about the Z-axis (arrows 80) relative to the surface 6. The support 142 can be used to raise or lower (arrows 83) the chassis 22 relative to the surface 6. Supports 146 can be used to stabilize the support 142 to the support structure 160. The support structure 160 can have multiple wheels 164 with multiple axles 162 to facilitate moving the support structure 160 along the surface 6 in the X and Y directions (arrows 166, 168). The support structure 160 can house an optional controller 169 for controlling the articulations of the base 18 to orient the chassis 22 in the desired orientation. This controller 169 can be positioned at any location in or on the base 18 as well as in or on the chassis 22. It is not required that the controller 169 be disposed in the support structure 160.

In a non-limiting embodiment, the delivery device 20 can include one or more storage bins 150 for storing objects 30 and delivering an object 30 to the barrel 360 at position 30'. In the example shown in FIG. 5, there are two storage bins 150a, 150b, but it should be understood that more or fewer storage bins 150 can be used in keeping with the principles of this disclosure. Storage bin 150a can contain objects 30a with storage bin 150b containing objects 30b. The controller 28, 29 (or coach 4, or trainee 8, or another individual) can select which storage bin 150a, 150b is to provide the object 30 to the barrel 360 at position 30'. If the object 30a is selected, then the storage bin 150a can release one object 30a that can be directed to the position 30' via a conduit 156. If the object 30b is selected, then the storage bin 150b can release one object 30b that can be directed to the position 30' via a conduit 156. Only one object 30a or 30b is released at a time in this configuration.

However, the conduit 156 can be a collection conduit that receives each object 30a or 30b and holds them in a chronological order in the conduit 156 as to when they were received at the conduit 156 from the storage bins 150a, 150b. A mechanism 155 can be used to release the next object (30a or 30b) into the barrel 360 at position 30', thereby delivering the objects 30a, 30b to the barrel 360 in the order they were received at the conduit 156. Even if only one object 30a, 30b is released to the conduit 156, the mechanism 155 can still be used to prevent the escape of pressurized gas into the conduit 156. However, the mechanism 155 is not required. Other means can be provided to prevent loss of pressurized gas through any other path other than through the barrel 360.

FIG. 6 is a representative perspective view of a friction device 200 for the delivery device 20. As similarly described above, the friction device 200 can be rotated about its axis 92 (arrows 87) as well as being rotated about the axis 90 of the barrel 360 (arrows 96). A support (e.g., support 202) can be used to support and rotate the friction device 200 about the axis 92. The barrel 360 can be rotated about the axis 90 (arrows 86) and moved toward or away from the friction device 200 (arrows 85). The object 30 can exit the barrel 360 with a velocity vector 174 at position 30''. If the object 30 impacts the friction device 200 at position 30''', then a spin 94 can be imparted to the object 30 as well as deflecting the object 30 substantially by an angle A1 relative to the center axis 90 of the barrel 360. The object 30 can travel along the resulting trajectory 48 from the object 30 impacting the friction device 200. The object 30 can have a resulting velocity vector 176 at position 30''.

In a non-limiting embodiment, the velocity vector 174, 176, 178 can be a velocity directed in any 3D direction, with the velocity of the object 30 being at least 4 MPH (i.e., miles per hour), at least 5 MPH, at least 6 MPH, at least 7 MPH, at least 8 MPH, at least 9 MPH, at least 10 MPH, at least 15 MPH, at least 20 MPH, at least 25 MPH, at least 30 MPH, at least 35 MPH, at least 40 MPH, at least 45 MPH, at least 50 MPH, at least 55 MPH, at least 60 MPH, at least 65 MPH, at least 70 MPH, at least 75 MPH, at least 80 MPH, at least 90 MPH, or at least 100 MPH.

In another non-limiting embodiment, the velocity vector 174, 176, 178 can be a velocity directed in any 3D direction, with the velocity of the object 30 being no greater than 220 MPH, no greater than 210 MPH, no greater than 200 MPH, no greater than 190 MPH, no greater than 180 MPH, no greater than 170 MPH, no greater than 160 MPH, no greater than 150 MPH, no greater than 145 MPH, no greater than 140 MPH, no greater than 135 MPH, no greater than 130 MPH, no greater than 125 MPH, no greater than 120 MPH, no greater than 115 MPH, no greater than 110 MPH, no greater than 105 MPH, no greater than 100 MPH, no greater than 95 MPH, no greater than 90 MPH, no greater than 85 MPH, no greater than 80 MPH, no greater than 75 MPH, no greater than 70 MPH, no greater than 65 MPH, no greater than 60 MPH, no greater than 55 MPH, no greater than 50 MPH, no greater than 45 MPH, or no greater than 40 MPH.

It will be appreciated that the velocity of the object 30 at the velocity vector 174, 176, 178 may be within a range including any one of the minimum and maximum values noted above, including for example, but not limited to at least 5 MPH and not greater than 75 MPH, or within a range of at least 15 MPH and not greater than 100 RPM, or within a range of at least 15 MPH and not greater than 220 MPH.

In a non-limiting embodiment, the friction device 200 can include a ramp 206 with one or more surface materials attached to it. The surface material controls a friction applied to the object 30 when the object 30 impacts the friction device 200. Therefore, it can be beneficial to allow the delivery device 20 to automatically select between various surface materials (e.g., 204, 205, 208). One side of the ramp 206 can have multiple surface materials 204, 205 attached thereto. Moving the friction device 200 axially (arrows 88) can cause the object to impact either the surface material 204 or 205. If the surface materials 204, 205 have different textures or friction coefficients, then impacting one or the other can alter the spin 94 or trajectory 48 of the object 30 when it impacts the friction device 200. The ramp 206 can also have one or more surface materials (e.g., 208) attached to an opposite side of the ramp 206. The ramp 206 can be configured to rotate about the axis 92 such that the surface material 208 is positioned to impact the object 30 at position 30''''. The surface materials 204, 205, 208 can be various wool fibrous materials, plastics, cottons, foam rubbers, metals such as steel, lead, copper, aluminum, or metal alloys, plant-based material, or fungus-based material.

In a non-limiting embodiment, the surface material 204, 205, 208 can have a friction coefficient that is at least 0.010, at least 0.015, at least 0.20, at least 0.25, at least 0.30, at least 0.35, at least 0.40, at least 0.45, at least 0.50, at least 0.55, at least 0.60, at least 0.65, at least 0.70, at least 0.75, at least 0.80, at least 0.85, at least 0.090, at least 0.095, at least 0.10, at least 0.15, at least 0.20, at least 0.30, at least 0.40, at least 0.50, at least 0.60, at least 0.70, at least 0.80, at least 0.90, or at least 1.00.

In another non-limiting embodiment, the surface material 204, 205, 208 can have a friction coefficient that is no greater than 1.50, no greater than 1.45, no greater than 1.40, no greater than 1.35, no greater than 1.30, no greater than 1.25, no greater than 1.20, no greater than 1.15, no greater than 1.10, no greater than 1.05, no greater than 1.00, no greater than 0.95, no greater than 0.90.

It will be appreciated that the friction coefficient may be within a range including any one of the minimum and maximum values noted above, including, for example, but not limited to at least 0.20 and not greater than 1.35, or within a range of at least 0.01 and not greater than 1.50, or within a range of at least 0.25 inches and not greater than 1.35.

FIG. 7 is a representative partial cross-sectional view of the friction device 200 along line 7-7 as shown in FIG. 5. The structure 210 can rotate (arrows 95) about the center axis 90 of the barrel 360. With the friction device 200 coupled to the structure 210 via the rotatable support 202, the friction device 200 can be rotated (arrows 96) about the center axis 90. The friction device 200 can be inclined relative to the center axis 90 by being raised up or down (arrows 89) relative to the center axis 90. Therefore, the friction device 200 can be positioned at any azimuthal position about the center axis 90 as well as being rotated about its own axis 92 (arrows 87). When the object 30, traveling along the trajectory 46, impacts the friction device 200 it can be deflected from the friction device 200 along a trajectory 48 with a spin 94 at position 30''''. The desired spin 94 to the object 30 can also be represented as the desired yaw, pitch, and roll of the object 30.

FIGS. 8A-8D are representative partial cross-sectional views along line 8-8 as shown in FIG. 5 of a barrel 360 or barrel assemblies 370 of a delivery device 20. FIG. 8A shows a single barrel 360 with a smooth internal bore 368 and an outer surface 362. This barrel 360 can be used to minimize spin imparted to the object 30 as the object travels along the trajectory 46 through the barrel 360. FIG. 8B shows a single barrel 360 with a grooved internal bore 368 with grooves 364 and ridges 366. These grooves 364 and ridges 366 can be referred to as "rifling" of the barrel 360. The grooves 364 and ridges 366 can form helically oriented paths along the internal bore of the barrel 360 that can impart either clockwise or counterclockwise rotation of the object 30 as it travels along the barrel 360. However, the grooves 364 and ridges 366 can be parallel with the center axis 90 to minimize rotation of the object 30 along the trajectory 46 in the barrel 360.

In a non-limiting embodiment, an inner diameter D2 of the internal bore 368 can be larger than the object diameter D1 by at least 0.01% of D1, at least 0.1% of D1, at least 0.2% of D1, at least 0.3% of D1, at least 0.4% of D1, at least 0.5% of D1, at least 0.6% of D1, at least 0.7% of D1, at least 0.8% of D1, at least 0.9% of D1, at least 1.0% of D1, at least 1.1% of D1, at least 1.2% of D1, at least 1.3% of D1, at least 1.4% of D1, at least 1.5% of D1, at least 1.6% of D1, at least 1.7% of D1, at least 1.8% of D1, at least 1.9% of D1, or at least 2.0% of D1.

In another non-limiting embodiment, the inner diameter D2 of the internal bore 368 can be larger than the object diameter D1 by no greater than 20% of D1, no greater than 19% of D1, no greater than 18% of D1, no greater than 17% of D1, no greater than 16% of D1, no greater than 15% of D1, no greater than 14% of D1, no greater than 13% of D1, no greater than 12% of D1, no greater than 11% of D1, no greater than 10% of D1, no greater than 9% of D1, no greater than 8% of D1, no greater than 7% of D1, no greater than 6% of D1, no greater than 5% of D1, no greater than 4% of D1, no greater than 3% of D1, no greater than 2% of D1, or no greater than 1% of D1.

It will be appreciated that inner diameter D2 of the internal bore 368 may be larger than the object diameter D1 within a range including any one of the minimum and maximum values noted above, including, for example, but not limited to at least 0.01% of D1 and not greater than 20% of D1, or within a range of at least 0.1% of D1 and not greater than 10% of D1, or within a range of at least 0.1% of D1 and not greater than 2% of D1.

FIG. 8C shows a barrel assembly 370 that can include multiple barrels 360. In this example configuration, the barrel assembly 370 includes four barrels (360a, 360b, 360c, 360d) that can be rotated together around axis 374 (arrows 372). Each of the barrels 360a, 360b, 360c, 360d can have grooved or smooth bores. Therefore, the controller 28, 29 or user 4, 8 can select which of the barrels to be used in delivering the object 30. In FIG. 8C, the top barrel 360a is in the position of receiving the object 30 and delivering the object along the trajectory 46 and axis 90. If the assembly 370 were rotated clockwise (arrows 372) by one barrel position, then the barrel 360d can be positioned to receive the object 30 and deliver the object along the trajectory 46 and axis 90.

FIG. 8D shows a barrel assembly 370 that can include multiple barrels 360. In this example configuration, the barrel assembly 370 includes two barrels (360a, 360b) that can be moved side to side (arrows 376). Each of the barrels 360a, 360b, can have grooved or smooth bores. Therefore, the controller 28, 29 or user 4, 8 can select which of the barrels to be used in delivering the object 30. In FIG. 8D, the left barrel 360a is in the position of receiving the object 30 and delivering the object along the trajectory 46 and axis 90. If the assembly 370 were moved to the left (arrows 376), then the barrel 360b can be positioned to receive the object 30 and deliver the object along the trajectory 46 and axis 90. It should be understood that various other barrel or barrel assembly configurations can be used in keeping with the principles of this disclosure.

In a non-limiting embodiment, an object sorter 270 with body 280 may be provided to automatically sort a variety of different objects 30 and deliver the sorted objects (e.g., 30a, 30b) to multiple storage bins 150 (e.g., 150a, 150b) in the delivery device 20. In this example, a bin 282 can contain multiple types of objects 30a, 30b which can have at least one different characteristic than the other objects. The various characteristics of an object can be color, shape, surface texture, surface features, size, weight, or a visually identifiable marking (e.g., bar code, Q-code, etc.). The different objects 30a, 30b can be delivered to the object sorter 272 via a conduit or passage 274. The object sorter 272 can be configured to detect the particular differences between the objects 30a and objects 30b. After identifying the differences, the sorter can deliver the appropriate objects to the appropriate storage bins 150a, 150b via passageways 276, 278. If more objects 30 are used, with additional storage bins 150 to contain the different objects 30 after being sorted, then this may require more passageways to deliver the objects to the appropriate storage bins 150.

In a non-limiting embodiment, the delivery device 20 parameters can comprise one or more of the following:
- air pressure supplied to the training object 30 to propel the training object 30 through a barrel 360 with a center axis 90;
- air volume supplied to the training object 30;
- inclination of the barrel 360;
- azimuthal orientation of the barrel 360;
- length of the barrel 360;
- barrel 360 selection;
- inclination of a friction device 200 that comprises a ramp 206 and a surface material 204, 205, 208 on the ramp 206;
- azimuthal orientation of the friction device 200 around the center axis 90 of the barrel 360;
- azimuthal orientation of the friction device 200 about a longitudinal axis 92 of the friction device 200;
- length of the friction device 200;
- the surface material 204, 205, 208 of the friction device 200;
- object launch position from the delivery device 20, the object launch position being a location in 3D space of an X-Y-Z coordinate system;
- object 30 selection;
- height of the delivery device 20;
- inclination of the delivery device 20;
- azimuthal orientation of the delivery device 20;
- distance to a target zone 50; and
- height of the target zone 50.

FIGS. 10A-10D are representative functional diagrams of systems and methods for a delivery device 20 to deliver an object 30 along at least a portion of a game trajectory 140 of a sports object 130. Each of the figures show a real-life participant 14 (such as a real-life sports player) that has delivered a regulation object 130 to a target zone 50 along a game trajectory 140. A tracking device 190 can be used to capture the game trajectory 140 of the sports object 130. The game trajectory 140 can also be captured in historical videos that can be used by the controller 28, 29 to determine the parameters of the delivery device 20 to mimic at least a portion of the game trajectory 140. Additionally, or in the alternative, the game trajectory 140 can be collected (or sent) from a statistics database 36 to the controller 28, 29, wherein the statistics database 36 contains the parameters of the game trajectory 140 that can be used to determine the parameters of the delivery device 20. For example, the statistics database 36 can be the Statcast database which is an application programming interface (API) for sports data.

A controller 28, 29 can be used to analyze the parameters of the game trajectory 140 to determine the delivery device parameters that can be used by the delivery device 20 to project a training object 30 along at least a portion of the game trajectory 140. The training object 30 can be projected along a training trajectory 40 that at least substantially mimics the game trajectory 140 for a portion of the game trajectory 140. The controller 28, 29 can determine the characteristics of the sports object 130 (such as spin 132 and velocity vector 134 at positions 130' and 130") as it travels long the game trajectory 140 as captured by the imaging sensor(s) 32. The game trajectory 140 can also include the position in the target zone at which the sports object 130 arrived.

The tracking device 190 can include a controller 192 that is communicatively coupled to a tracking sensor 194. The tracking sensor 194 can capture imagery of the game trajectory 140 or otherwise detect the parameters of the sports object 130 as it travels along the game trajectory 140. In a non-limiting embodiment, the imaging sensor 194 can include a camera, a 2D camera, a 3D camera, a LiDAR sensor, a smartphone, a tablet, a laptop, or other video recorders. The controller 192 can receive the tracking data from the tracking sensor 194 and save the tracking data for later analysis. The tracking device 190 can be communicatively coupled to the controller 28, 29 via a wireless or wired network, or the tracking data can be transferred to the controller 28, 29 from the tracking device 190 via a non-transitory memory storage (e.g., USB drive). The controller 28, 29 can request transfer of the tracking data from the tracking device 190, or the tracking device 190 can transmit the tracking data to the controller 28, 29. The tracking device 190 can store the tracking data in a non-transitory memory storage 196 or in an external statistics database 36. The controller 28, 29 can retrieve the tracking data from the tracking device 190 or from the statistics database 36.

Figure 10A:
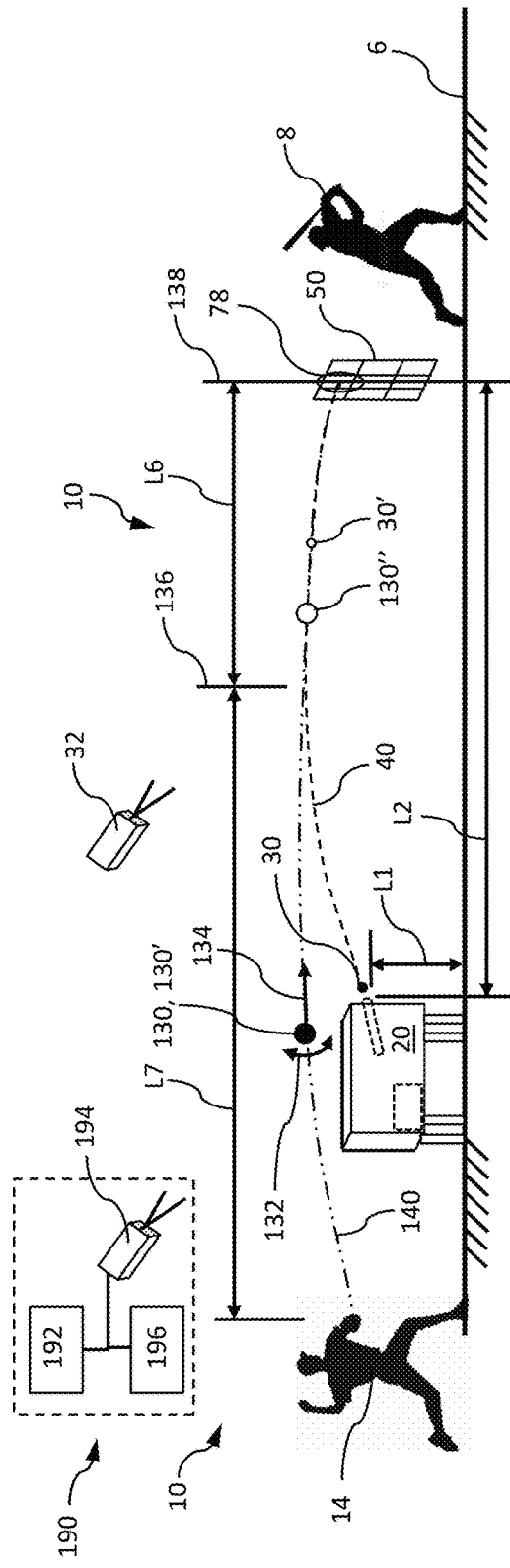
FIGS. 10A-10D are representative functional diagrams of systems and methods for a delivery device to deliver an object along at least a portion of a game trajectory of a sports object, in accordance with certain embodiments.

FIG. 10A shows a deliver device 20 at a location closer to the target zone 50 than the real-life participant 14 was in the real-life event in which the sports object 130 was delivered and positioned at a position that delivers the object 30 in a trajectory 40 that does not initially align with the game trajectory 140. In a non-limiting embodiment, the determined delivery device (DD) parameters can configure the delivery device 20 to project an object 30 along the trajectory 40 that can overlap the game trajectory 140 by a distance L6, with the distance L7 being the remaining distance of the game trajectory 140 from the first substantially common point 136 between the game trajectory 140 and the training trajectory 40. The training object 30 can be delivered to the target zone 50 consistently within a grouping 78 at the target zone 50 (at position 138). In a non-limiting embodiment, the grouping 78 can have a diameter of less than 2 inches, less than 1.9 inches, less than 1.8 inches, less than 1.7 inches, less than 1.6 inches, less than 1.5 inches, less than 1.4 inches, less than 1.3 inches, less than 1.2 inches, less than 1.1 inches, less than 1.0 inches, less than 0.5 inches, or less than 0.1 inches.

The overall distance of the game trajectory 140 is seen as being L6 plus L7 (or L6+L7). In a non-limiting embodiment, the distance L6 can be 100%, less than 100%, less than 99%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, or less than 20% of the overall distance of the game trajectory (i.e., L6+L7). In another non-limiting embodiment, the distance L6 can be greater than 5%, greater than 10%, greater than 15%, greater than 20%, greater than 25%, greater than 30%, greater than 35%, greater than 40%, greater than 45% of the overall distance of the game trajectory (i.e., L6+L7).

It will be appreciated that the distance L6 can be a percentage of the overall distance of the game trajectory with the percentage being within a range including any one of the minimum and maximum values noted above, including, for example, but not limited to at least 5% of L6+L7 and not greater than 95% of L6+L7, or within a range of at least 10% of L6+L7 and not greater than 50% of L6+L7, or within a range of at least 20% of L6+L7 and not greater than 40% of L6+L7.

Additionally, in a non-limiting embodiment, the game parameters of the game trajectory 140 can be determined by at least one of:
- tracking the game trajectory 140 during a real-time sports event, determining the game parameters for the game trajectory 140, and sending the game parameters to the controller 28, 29 in real-time or as desired after the game trajectory 140 is captured,
- tracking the game trajectory via a tracking device 190 during the real-time sports event, determining the game parameters for the game trajectory 140, storing the game parameters in a non-transitory memory 196 or database 36, and retrieving, via the controller 28, 29, the game parameters from the tracking device 190;
- tracking the game trajectory via a tracking device 190 during the real-time sports event or real-time practice session, determining the game parameters for the game trajectory 140, and retrieving, via the controller 28, 29, the game parameters from the tracking device 190;
- tracking the game trajectory 140 via a tracking device 190 during the real-time sports event or real-time practice session, determining the game parameters for the game trajectory 140, and retrieving, via the controller 28, 29, the game parameters from the tracking device 190 in real-time;
- collecting the game parameters from one or more data sources (such as memory 196 or databases 36) and sending the game parameters to the controller 28, 29;
- retrieving, via the controller 28, 29, the game parameters from a database 36; or
- combinations thereof.

In a non-limiting embodiment, the game parameters of the game trajectory 140 can comprise one or more of:
- a spin of the sports object,
- a speed of the sports object,
- a velocity vector of the sports object,
- a weight of the sports object,
- a size of the sports object,
- a surface texture of the sports object,
- a game trajectory of the sports object through a 3D space of an X-Y-Z coordinate system, and
- combinations thereof.

A plurality of game trajectories can be tracked by the tracking device 190 with game parameters determined for each one of the plurality of game trajectories. A set of parameters for the delivery device 20 can be determined for each one of the game trajectories, such that the delivery device parameters for each respective game trajectory 140 can mimic the respective game trajectory 140 by projecting a training object 30 along at least a portion of the respective game trajectory 140. By selectively adjusting (manually or automatically) the delivery device 20 based on each successive set of delivery device parameters, the delivery device 20 can mimic a set of sequential game objects projected in the real-life sports event. For example, the delivery device 20 can mimic a sequence of pitches by a specific pitcher in a baseball game (or real-life baseball practice session), a sequence of pitches by a specific pitcher in a softball game (or real-life softball practice session), a sequence of shots on goal by a specific hockey player in a hockey game (or real-life hockey practice session), a sequence of volleys hit during a tennis match (or real-life tennis practice session), etc.

Multiple sets of delivery device parameters, with each defining a predetermined trajectory 40, can be stored in the parameters database 38 as a sequence file that, when recalled by the controller 28, 29 can produce the desired sequence of predetermined trajectories 40. These sets of delivery device parameters Additionally, the sequence of training trajectories 40 can be built to emulate (or mimic) a sequence of game trajectories 140 as described above. Additionally, the sequence of training trajectories 40 can be built by a user (coach 4, trainee 8, controller 28, 29, another individual, etc.) as desired to build a tailored sequence of training trajectories 40 not necessarily related to a real-like game trajectory 140 of a game object 130.

Figure 10B:
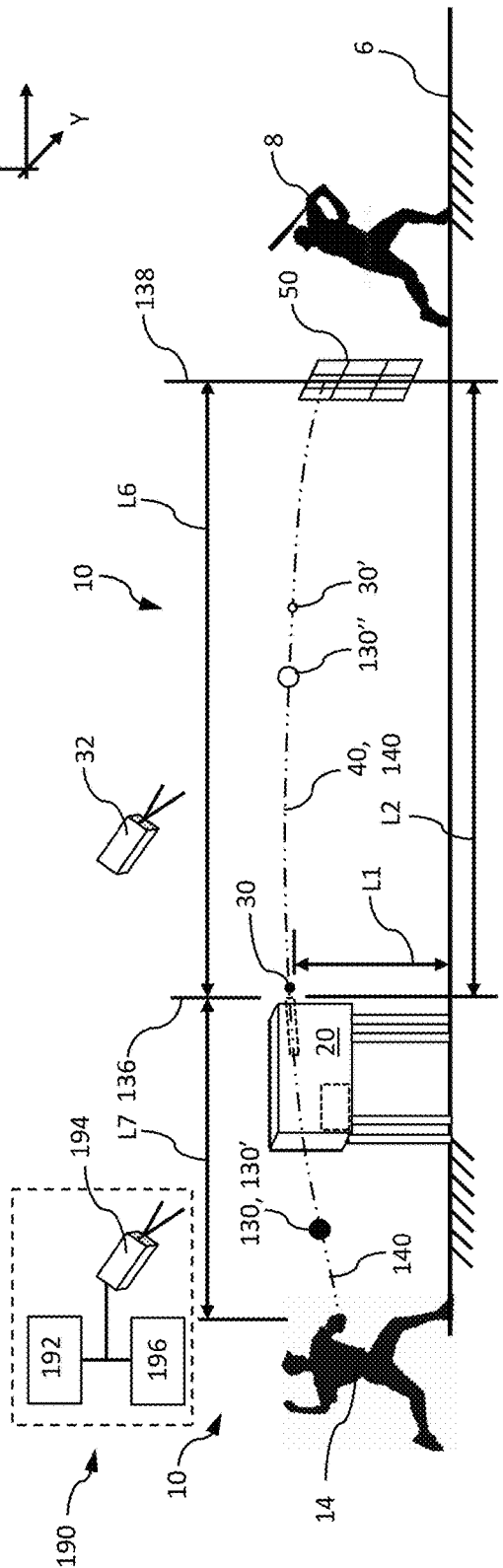

Referring now to FIG. 10B, as discussed above with regard to FIG. 10A, the tracking device 190 can track and record the game trajectories 140 of a game object 130 in a real-life sports event (which can include a real-life practice session). However, FIG. 10B differs from the training system 10 of FIG. 10A in that it projects the object 30 from the delivery device 20 substantially along the end portion of the game trajectory 140 as the object exits the delivery device 20. Therefore, a distance the object 30 travels along the game trajectory 140 (L6) can be longer than in FIG. 10A. In the FIG. 10B configuration, the delivery device 20 can be moved closer to the target zone 50 while maintaining a desired length L6 that the object 30 tracks the game trajectory 140. As can be seen the object 30 traveling along the training trajectory 40 (such as at position 30') substantially mimics the game trajectory 140 of the game object 130 (such as at position 130') to the target zone.

Figure 10C:
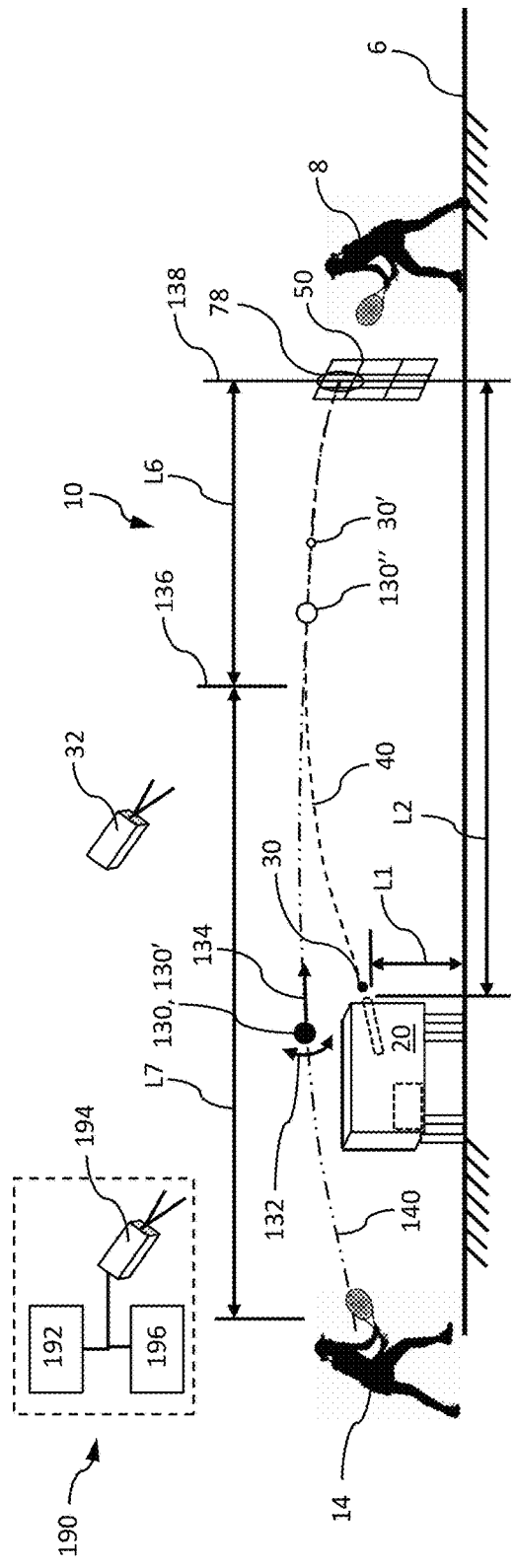
Figure 10D:
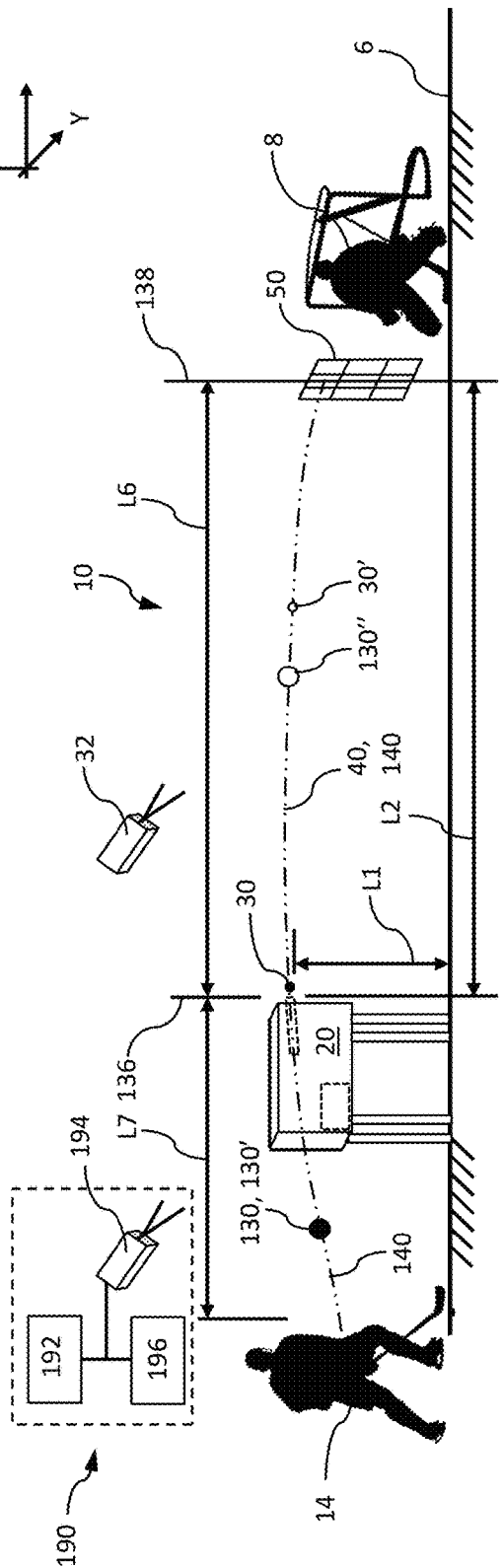

Referring now to FIGS. 10C and 10D, the description for FIGS. 10A and 10B applies to FIGS. 10C and 10D, except that the real-life participant 14 and the trainee in FIG. 10C are for the sport of tennis, and the real-life participant 14 and the trainee in FIG. 10D are for the sport of hockey. This demonstrates that the training system 10 can be used for training in multiple sports and it is not limited to baseball or softball.

Figure 11:
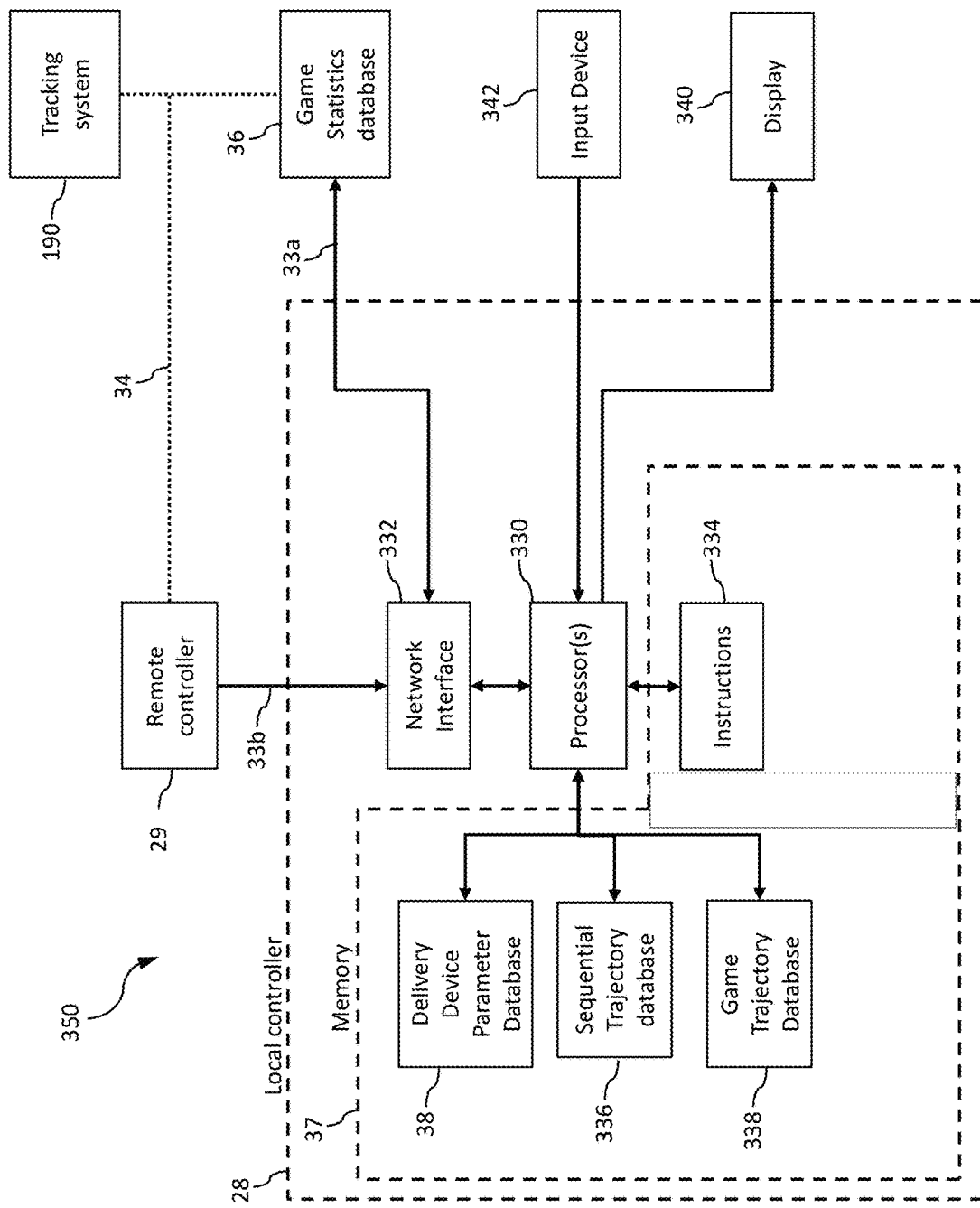
FIG. 11 is a representative functional block diagram of a control system for a training system, in accordance with certain embodiments.

FIG. 11 is a representative functional block diagram of a control system 350 for a training system 10. The local controller 28 can be communicatively coupled to the remote controller 29 via network 33b, the game statistics database 36 via network 33a, and input device 342, and a display 340. The input device 342 can provide a human-machine-interface (HMI) that accepts user inputs (trainee 8, coach 4, or others) and transmits the user inputs to one or more processors 330 of the controller 28. In a non-limiting embodiment, the input device can be a keyboard, mouse, trackball, virtual reality sensors, graphical user interface GUI, a touch screen, mechanical interface panel switches, a button, a stride sensor, microphone to input voice commands recognized by the controller 28, video sensors to detect gestures of a trainee 8 or coach 4 other individual.

In a non-limiting embodiment, the display 340 can be used to display performance scores to a user (i.e., trainee 8, coach 4, another individual, etc.), GUI interface windows, training trajectory (single or multiple), emulated game trajectory 140, and player 14 associated with the game trajectory 140, video of game trajectory 140, video of training trajectory while or after the object is projected to target zone, training statistics and trends, selection criteria objects 30, selection criteria for training trajectories 40, delivery device 20 parameters and selected parameters when selected by the input device. For example, in baseball or softball training, the display 340 can be used to display a type of pitch, the speed of delivery of object 30 at the target zone 50, a location of delivery of the object 30 at the target zone 50, text messages about the delivered object 30, animations, videos, photos, or alerts about the delivered object 30. The display is intended to provide the trainee 8 or coach 4 immediate feedback about the delivered object 30. The input device 342 and display 340 are shown separately, but they can be integrated together in a device, such as a smartphone, smart tablet, laptop, touchscreen, etc.

The network interface 332 can manage network protocols for communicating with external systems (e.g., controller 29, database 36, imagery sensors 32, tracking device 190, etc.) to facilitate communication between the processor(s) 330 and the external systems. These external systems are shown connected to the network 34, but they can also be disconnected and reconnected as needed. For example, the tracking device 190 may not be connected to the network until it is positioned on a docking station for downloading its acquired data. Additionally, the delivery device 20 may not always be connected to an external network. When it is reconnected to an appropriate external network, the communication between the external systems can again be enabled.

In a non-limiting embodiment, the processor(s) 330 can be communicatively coupled to a non-transitory memory storage 37 which can be used to store program instructions 334 and information in databases 38, 336, 338. The processor(s) 330 can store and read instructions 334 from the memory 37 and execute these instructions to perform any of the methods and operations described in this disclosure for the delivery device 20. The delivery device parameters (see parameters described above) for each training trajectory 40 can be stored in the delivery device parameter database 38 in the memory 37. This database 38 can be organized such that each training trajectory 40 that has been defined by a set of delivery device parameters can have a trajectory entry in the database 38. When this trajectory entry is accessed, the set of delivery device parameters can be transferred to the processor(s) 330, which can use the parameters to adjust the delivery device 20 components to deliver the predetermined trajectory defined by the trajectory entry.

If a user wishes to define a canned sequence of trajectories, then the processor(s) 330 (based on inputs from the input device) can assemble the sequence of trajectories including their associated delivery device parameters and store the sequence in the sequential trajectory database 336 as a retrievable set of predetermined trajectories. When accessed by the processor(s) 330, the sequential trajectory database 336 can deliver the set of predetermined trajectories to the processor(s) 330 including the delivery device parameters. The processor(s) 330 can then sequentially set up the delivery device 20 to sequentially project objects one after another to produce the desired set of predetermined trajectories in the desired order. The memory 37 may also contain a game trajectory database 338 which stores the game parameters of the game trajectories that have been received from other sources (such as the tracking device 190, the game statistics database 36, or user inputs) and can save them for later emulation by the delivery device 20.

Figure 12:
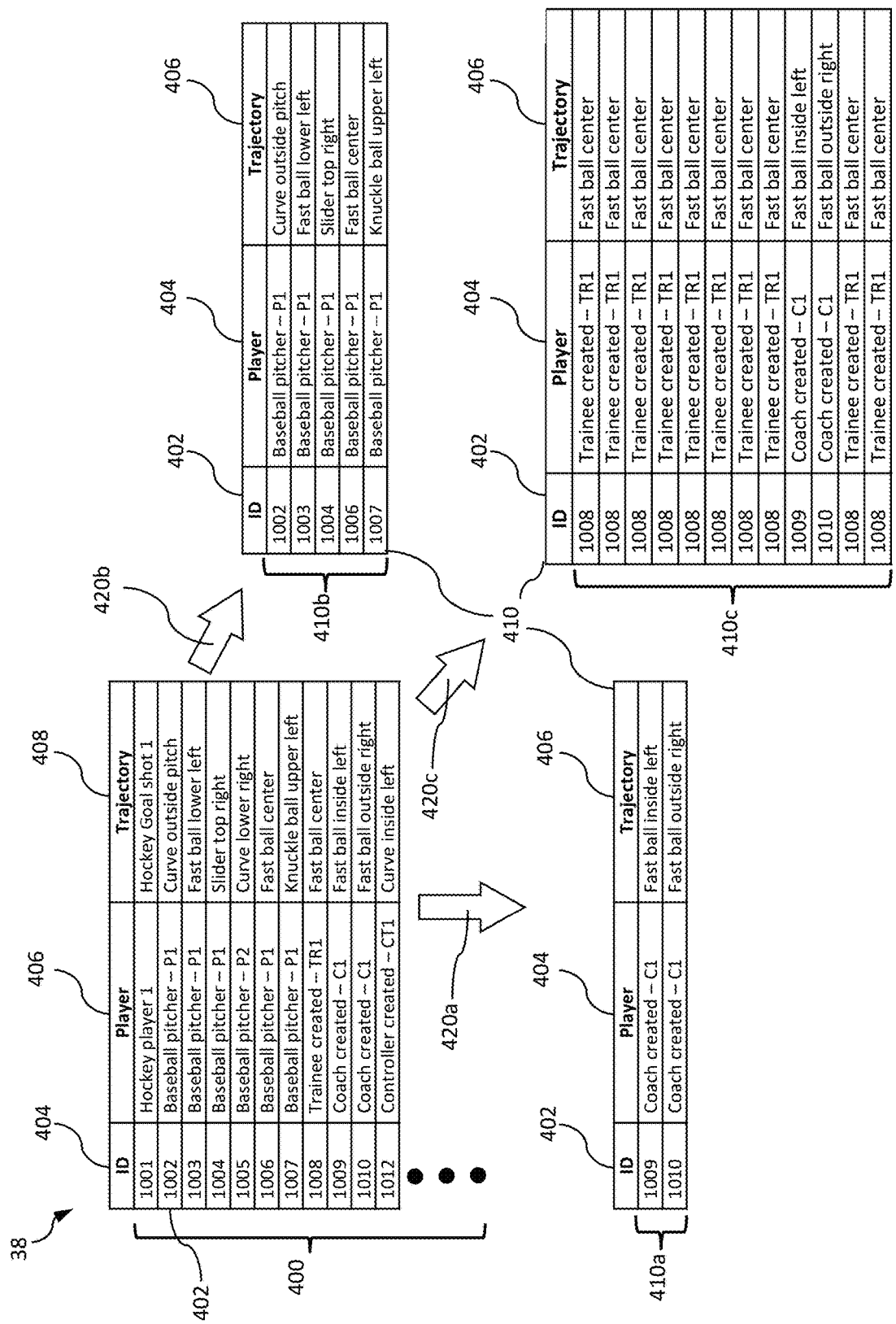
FIG. 12 is a representative functional block diagram of the parameter database for the training system, in accordance with certain embodiments.

FIG. 12 is a representative functional block diagram of the parameter database 38 which can be contained in the delivery device 20 but can also be contained in another non-transitory memory external to the delivery device 20, such as the remote controller 29. In a non-limiting embodiment, the parameter database 38 can contain multiple database entries 400 (e.g., 402) each with a unique identification (ID) 404, a player 406 associated with the entry (such as sports player, coach, controller 28, 29, trainee 8, etc.), and trajectory 408 for the entry. This list of entries 400 is shown with simplified variables for the ID 404, player 406, trajectory 408, but it should be understood that these variables can be as complicated as needed to perform the function of identifying the entry and provided guidance to the user for selecting and using it. For example, ID 1001 shows to be a trajectory from a hockey player identified as "hockey player 1" and the title indicates the trajectory to be a hockey shot on goal (no. 1). For example, ID 1002 shows to be a trajectory from a baseball pitcher labeled as "P1" and the trajectory 408 indicating that it will mimic a curve ball on the outside of the plate. The rest of the entries can be similarly identified to aid the user in knowing which one or more to select for training.

In a non-limiting embodiment, these trajectories represented by entries 400 can be individually selected to perform single or repeated training with the selected training trajectory 40. These trajectories represented by entries 400 can be randomly selected (e.g., via the controller 28, 29, or coach 4, or other means) to project subsequent objects 30 along the randomly selected trajectories which are selected from the list of entries 400. The random selection of trajectories including their associated delivery device parameters can be recorded and saved in the sequential trajectory database 336 and later retrieved to repeat the sequence of randomly selected trajectories, again. Additionally, as mentioned above with regards to the sequential trajectory database 336, the user can assemble the sequence of trajectories including their associated delivery device parameters and store the sequence in the sequential trajectory database 336 as a retrievable set of predetermined trajectories. Three examples of this process are shown for discussion purposes. Many more varieties of sequences 410 can be assembled than these shown in FIG. 12.

In a non-limiting embodiment, the entries 1009, 1010 are assembled (or compiled) 420*a* to produce a sequence 410*a* of two trajectories created by a coach 4 and appears it could be used for fast ball training.

In another non-limiting embodiment, the entries 1002-1004, 1006, and 1007 have been assembled 420*b* into a sequence 410*b* that appears to focus on a single baseball pitcher P1. This can be used to prepare for a real-life game situation (or real-life practice session) that pits the real-life pitcher P1 with the trainee 8.

In another non-limiting embodiment, the entries 1008-1010 are used to assemble 420*c* a sequence 410*c* that again appears to focus on fast ball training. The entry 1008 appears to be a training trajectory created by the trainee 8 and it has been replicated several times to create the sequence 410*c*. Entries 1009 and 1010, which appear to have been created by a coach 4, have been inserted near the end of the list. These sequences are generally user preference but can also be built to mimic a game trajectory sequence of game objects projected by a player in a real-life event (e.g., a sequence of pitches in baseball or softball).

In a non-limiting embodiment, the sequences 410*a*, 410*b*, 410*c*, as well as other sequences 410 not shown can be stored in the sequential trajectory database 336 for ease of access when the particular sequence 410 is desired to be used in training. The progression through the sequence of trajectories defined in a sequence 410 can be automatic, such that the delivery device 20 initiates the projection of the next object 30 along the next trajectory 40 in the sequence 410 based on a predetermined time interval. The time interval between each projected object 30 can be set to mimic the time interval between actual game object projections in the real-life sports event, for which the sequence 410 is mimicking. Alternatively, the predetermined time interval can be a set time, such as projecting each subsequent object after X time has elapsed since the last projection. Additionally, the predetermined time interval can be established by gestures of the trainee 8 (or coach 4) or through other user inputs.

FIG. 13A is a representative functional block diagram of a training system that can support a method of calibration 116. It should be understood that any of the training systems 10 described in this disclosure can be used for calibration. FIG. 13A is only one example of a system 10 that can be used for the calibration method 116. The training system 10 can include a delivery device 20 that can project an object 30, 430 toward a target zone 50 along a predetermined trajectory 40, 440, respectively. The controller 28, 29 can adjust the parameters of the delivery device 20 to control the trajectory of the object 30, 430. These parameters are described in more detail above with regard to FIGS. 1A, 1B, 1C, and 5-10D. In a non-limiting embodiment, the parameters control the aspects of the orientation, direction, and velocity of the object 30, 430 as it travels along its trajectory 40, 440 once projected from the delivery device 20.

For calibration, an expected trajectory 40 of the object 30 is compared to an actual trajectory 440 traveled by the object 430 after it is projected from the delivery device 20 toward the target zone 50. The expected trajectory 40 can be a trajectory whose attributes are stored in a trajectory database 336, 338 in the controller 28, 29 after the controller 28, 29 or tracking device 190 captured the trajectory 40 of the object 30 from a previous operation and saved the trajectory attributes in the database 336, 338. Alternatively, the expected trajectory 40 can be a trajectory that is captured at a beginning of the calibration method 116 and stored in the non-transitory memory 37. The expected trajectory 40 can then be used as the standard by which the subsequent actual trajectories 440 are measured against during the calibration method.

The method 116 can begin by retrieving or capturing the expected trajectory 40. The controller 28, 29 can then retrieve a set of calibration parameters from the parameters database 38, which can be a set of parameters for one or more trajectories. After adjusting the delivery device 20 based on the calibration parameters, the controller 28, 29, or user (e.g., trainee 8, coach 4) can initiate projection of an object 430 along an actual trajectory 440 toward the target zone 50. The controller 28, 29, via the imaging sensors or via the tracking device 190, can capture the attributes of the actual trajectory 440 and compare those attributes with the attributes of the expected trajectory 40. The deviations identified between the expected and actual trajectories can be used to adjust the delivery device parameters to minimize any deviations between the expected and actual trajectories, such as at least between a position 30" along the expected trajectory 40 and a position 430" along the actual trajectory 440. Sensors 51 in the target zone 50 can also be used to measure the arrival location of the object 430 at the target zone 50 and the controller 28, 29 can compare the actual location to an expected location.

After the adjustments to the delivery device 20 are made, the controller 28, 29, or user (e.g., trainee 8, coach 4) can initiate projection of subsequent object 430 along a subsequent actual trajectory 440 toward the target zone 50. The controller 28, 29, via the imaging sensors or via the tracking device 190, can capture the attributes of the subsequent actual trajectory 440 and compare those attributes with the attributes of the expected trajectory 40 to determine how effective the adjustments to the delivery device parameters were in reducing the deviations below an acceptable amount of deviation.

FIG. 13B is an expanded view of the actual and expected trajectories 440, 40 with exaggerated deviations for illustration purposes. The controller 28, 29 can analyze a plurality of corresponding positions of the objects 30, 430 along the respective trajectories to yield a satisfactory calibration of the delivery device 20. In this example, three positions along the trajectories are compared, but many more positions are preferably analyzed to ensure a valid calibration procedure. At position 430', the object 430 can be exiting the delivery device 20 with a velocity vector 476. When compared to the expected trajectory 40, the position 30' of the object 30 indicates a deviation of distance L10 between the position 30' and the position 430'. Also, the velocity vector 476 of the object 430 can be compared to the velocity vector 176 of the object 30 to identify any deviations in the vectors. The deviation distance L10 can be a result of components of the delivery device 20 that position the exit of the object from the delivery device 20, such as base 18 components, barrel 360 orientation, friction device 200 orientation, and surface material 204, 205, 208.

At position 430", the object 430 with a velocity vector 478 traveling along the actual trajectory 440 can be compared to the position 30" of the object 30 with a velocity vector 178 traveling along the expected trajectory 40. When compared to the expected trajectory 40, the position 30" of the object 30 indicates a deviation of distance L11 between the position 30" and the position 430". Also, the velocity vector 478 of the object 430 can be compared to the velocity vector 178 of the object 30 to identify any deviations in these vectors. The deviation distance L11 can be a result of variations in any of the components of the delivery device 20 or object 430 that affect the position, velocity vector, and spin of the object 430 as it travels along the actual trajectory 440.

At position 430''', the object 430 has arrived at the target zone 50 and the position 430''' can be compared to the position 30''' of the object 30 at the target zone 50. When compared to the expected trajectory 40, the position 30''' of the object 30 indicates a deviation of distance L12 between the position 30''' and the position 430'''. The deviation distance L12 can be a result of variations in any of the components of the delivery device 20 or object 430 that affect the position, velocity vector, and spin of the object 430 as it travels along the actual trajectory 440.

In a non-limiting embodiment, the controller 28, 29 can determine a score to indicate how well the delivery device 20 minimizes deviations between the actual and expected trajectories. The smaller the deviations the better the score. When the score is below a predetermined value, further calibration activities may be needed. When the score is equal to or above the predetermined value, the calibration can be seen as successful, such that the delivery device 20 (after an acceptable calibration score) can reliably deliver the object 430 or 30 substantially along an expected trajectory.

When the score is below the predetermined value, manual adjustments can be made to correct at least some of the deviations, such as replacing or repairing degraded components. However, manual adjustments can also be via user inputs to the controller 28, 29 to adjust the parameters of the delivery device 20. When the score is above or equal to the predetermined value, then the controller 28, 29 can compare the current parameters to the set of calibration parameters and create a set of offset parameters, which the controller 28, 29 can use when projecting subsequent objects such that the offset parameters can be used to modify a stored set of parameters for a predetermined trajectory such that the offset parameters compensate for the variations in the delivery device 20 identified in the calibration process.

It should also be understood that the calibration process and the creation of the set of offset parameters can be done automatically under the control of the controller 28, 29. The controller 28, 29 can initiate projection of the object 430 along the actual trajectory 440, compare the actual trajectory 440 to the expected trajectory 40, determine the score, adjust the delivery device 20 parameters if needed (if not needed, then stop), initiate projection of another object 430 along another actual trajectory 440, compare the actual trajectory 440 to the expected trajectory 40, determine the score, and repeat the process until the score is at an acceptable level. When the score is acceptable, then the controller 28, 29 can create the set of offset parameters to be used for subsequent object 30 projections to adjust delivery device 20 parameters to compensate for variations of the delivery device 20 which caused the deviations.

FIGS. 14A-14E are representative functional diagrams of systems and methods for training a trainee to improve coordination, vision training, and/or tracking capabilities through segmenting training 118. In general, for segmenting training a trainee 8 can be positioned proximate a target zone 50, at which the delivery device 20 can project an object 30 along a predetermined trajectory 40. A barrier 220 can be positioned between the delivery device 20 and the trainee 8 so the trainee 8 cannot see the delivery device 20 (at least maybe not directly) as it projects the object 30. The barrier 220 prevents the trainee 8 from seeing the object 30 traveling along a beginning portion of the trajectory 40 after it exits the delivery device 20. After some distance along the trajectory 40, the barrier 220 is no longer obstructing the vision of the trainee 8 and the trainee 8 can begin to locate and track the object 30 as it completes its travel along the remaining portion of the trajectory 40.

As the trainee 8 gets better at tracking the object 30 along the reduced distance of the trajectory 40, the barrier 220 can be moved closer to the trainee 8 to restrict the distance the trainee 8 can see the object 30 along the trajectory 40. This reduced distance causes the trainee 8 to have to hone his eye recognition skills even more to consistently recognize and track the object 30 along the reduced distance of the trajectory 40. When the trainee 8 is able to do this, the barrier can again be moved closer to the trainee 8 to restrict the portion of the trajectory 40 viewable by the trainee 8 even further. This process can be repeated until the trainee 8 can successfully recognize and track the object 30 along a minimum portion of the trajectory 40. FIGS. 14A-14E demonstrate various configurations of using the delivery device 20 to project an object toward the target zone, and a barrier positioned to restrict the distance along the trajectory 40 that the object is viewable to the trainee 8.

In a non-limiting embodiment, FIG. 14A shows a training system 10 for segmenting training 118 that uses a barrier 220 that can include one or more openings in the barrier through which the delivery device 20 can be configured to project the object along a predetermined trajectory (e.g., trajectory 40). The holes can be positioned in a way as to not allow the trainee 8 to view the object 30 as it exits the delivery device 20. As the object 30 travels along the trajectory 40, the object 30 can travel through one of the openings, with the object possibly being visible to the trainee 8 prior to it passing through the opening, but the barrier 220 still can restrict the vision of the trainee 8.

In a non-limiting embodiment, portions of the barrier 220 can include a plurality of longitudinal slits that run parallel with each other. The orientation of the slits can be vertical, horizontal, or inclined between vertical and horizontal. As the object 30 impacts the slits, the slits move out of the path of the object 30 as the object 30 passes through the slits and then the slits can return to the original position before being displaced by the object 30.

In another non-limiting embodiment, the openings in the barrier 220 can be provided with one or more apertures that can be selectively opened and closed in synchronization with the delivery device 20. When an object 30 is to be delivered along a predetermined trajectory 40 that includes passing through one of the apertures, then the respective aperture can be opened just prior to the object arriving at the aperture and then closed after the object has passed through the aperture.

In this example, the barrier 220 is positioned at a distance L8 from the target zone 50. The delivery device 20 can begin sequentially projecting objects 30 along one or more trajectories 40 (some of the trajectories can be different than the others). The target zone 50 can include sensors 51 that can detect the where and when the object arrives at the target zone 50. This information can be transmitted to the controller 28, 29 for determining a performance score of the trainee 8.

The segmenting training method 118 can include where the trainee 8 attempts to recognize and track the object along the viewable portion of the trajectory 40 and the imaging system (e.g., the imaging sensors 32 and the controller 28, 29) can track the eye movements of the trainee 8. The controller 28, 29 can then correlate the detected eye movements with the trajectory 40 and score the trainee's ability to recognize and track the object 30 along at least a portion of the trajectory 40.

The segmenting training method 118 can alternatively, or in addition, include an impact device as described above with reference to FIGS. 2A, and 3A-3E where the trainee 8 attempts to recognize and track the object along the viewable portion of the trajectory 40 strike the impact device 52 with a regulation sports tool 12. The controller 28, 29 can collect the data from the sensors 51, 58 and score the trainee 8 on their ability to correctly strike the impact zone 56 of the impact device 52 at the appropriate time and location compared to the arrival time and arrival location of the object 30 at the target zone 50. The trainee 8 can be successively challenged more and more as their score improves and as a result the barrier 220 is moved (arrows 97) closer (e.g., barrier position 220') or even closer (e.g., barrier position 220"). If the score is not at a level needed to progress moving the barrier closer, then the barrier 220 can remain at its current position or be moved further away from the target zone 50. Also, if the trainee 8 has an acceptable score with barrier 220 at position 220', but fails to progress further, the barrier 220 can be moved to the original position and the segmenting training can begin again.

FIG. 14B shows a training system 10 used for segmenting training 118 which is similar to the configuration shown in FIG. 14A, except that a light source 230 can be positioned on the trainee 8 side of the barrier 220 to illuminate object 30 for only the portion of the trajectory 40 desired for the segmenting training 118. If the light source 230 is a type (such as UV light, etc.) that may be harmful to the trainee's eyes, then the light source 230 can be shielded from the trainee's eyes so that no direct light is delivered to the trainee's eyes. However, the light source 230 can still illuminate the object 30 along at least a portion of the trajectory 40. The light source 230 can be moved (arrows 97) along with the barrier 220 to other positions 230' and 230".

However, the light source 230 can also remain in a position while the barrier 220 is moved. It is not a requirement for the light source 230 to move with the barrier 220.

FIG. 14B shows a trainee 8 with a human machine interface (HMI) device that can be used by the trainee 8 to provide user inputs for when the trainee 8 expects the object 30 to arrive at the target zone 50. The trainee 8 can also use the HMI device 170 to indicate recognition of the object 30 along the trajectory 40 as well as when it is received at the target zone 50. The HMI device 170 can be communicatively coupled to the controller 28, 29 via the network 34.

The accuracy of receiving the user input from the HMI device 170 at the appropriate time to indicate the arrival of the object 30 can be scored by the controller 28, 29 (or the coach 4, or another individual). The trainee 8 can use an HMI device instead of a sports tool for any of the training systems described in this disclosure. For example, a trainee 8 with an HMI device 170 can be used to perform strike zone training, where the trainee 8 indicates, via the HMI device 170 when the object 30 is received at the target zone either inside or outside the target zone 50. Additionally, a trainee 8 with an HMI device 170 can be used to perform impact device training, where the trainee 8 indicates, via the HMI device 170, when the object 30 is received at the target zone instead of striking the impact device 52 with a sports tool 12.

FIGS. 14C, 14D each shows a training system 10 for segmenting training 118 that uses a barrier 220 that can be smaller than the barrier 220 shown in FIGS. 14A, 14B. The barrier 220 can be small enough that the delivery device 20 can be configured to project the object 30 around the barrier 220 to the left, right, above, or below while traveling along a predetermined trajectory to the target zone 50. The barrier 220 still blocks the view of the object 30 from the trainee 8 for at least a portion of the trajectory (40, 42). As described above, the barrier 220 can be moved (arrows 97) closer to or away from the trainee 8 to facilitate the segmenting training 118. The barrier 220 can also be moved side-to-side (arrows 98) if desired. In FIG. 14C, the object 30 can follow a trajectory 40 that takes the object 30 above the barrier 220, such as at position 30', or a trajectory 42 that takes the object 30 below the barrier 220, such as at position 30" on its way to the target zone 50. In FIG. 14D, the object 30 can follow a trajectory 40 that takes the object 30 to the left of the barrier 220 (as viewed from the delivery device 20), such as at position 30', or a trajectory 42 that takes the object 30 to the right of the barrier 220 (as viewed from the delivery device 20), such as at position 30", on its way to the target zone 50.

Figure 14E:
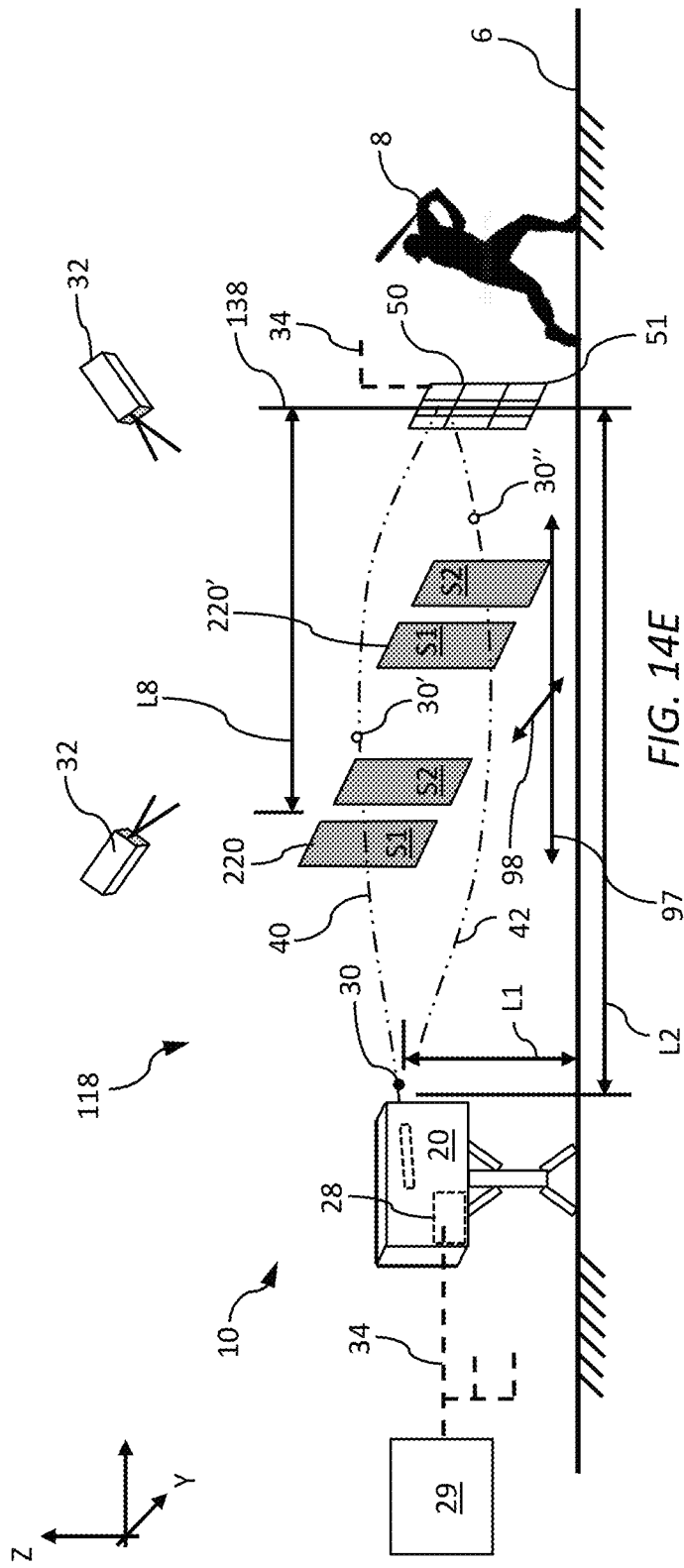

FIG. 14E shows a training system 10 for segmenting training 118 that uses a barrier 220 that can be multiple screens 51, S2 positioned proximate each other to allow a space therebetween through which an object 30 can be projected. This can differ from the barrier 220 shown in FIGS. 14A, 14B such that the screens 51, S2 are positioned to form spaces through which the object 30 can travel without forming openings in the screens. It should be understood that more than two screens can be used for the barrier 220. In FIG. 14D, the object 30 can follow a trajectory 40 that takes the object 30 between the screens 51, S2 when they are positioned to the left (as viewed from the delivery device 20), such as at position 30', or the object 30 can follow a trajectory 42 that takes the object 30 between the screens S1, S2 when they are positioned to the right (as viewed from the delivery device 20), such as at position 30". Similar trajectories can be created to direct the object 30 through spaces between the screens 51, S2 if the barrier 220 is moved to other positions other than 220 and 220'.

FIG. 14F shows a training system 10 for segmenting training 118 that uses a barrier 220 that can be one or more screen 51. This segmenting training 118 can be used to train a trainee 8 to improve their defensive abilities. In this example of segmenting training 118, the delivery device 20 can project the object 30 directly at the trainee 8 or at least toward the trainee 8. The trainee 8 can be equipped with a sports tool 12, such as a glove, a mitt, a padded garment, a bat, a racket, etc., to use to make contact with the object 30 and deflect its trajectory away from the target zone 50 or to capture the object 30. The trainee 8 can also not have a sports tool and merely use his body movements to deflect the object 30 or to avoid the object 30 altogether. Sensors in the sports tool 12 or the imaging sensors 32 can detect when the trainee 8 is able to deflect or catch the object 30 or avoid the object, whatever is desired for the training. The controller 28, 29 can determine a performance score for the trainee 8 to indicate the trainee's ability to perform the desired training activity. As the trainee 8 improves to a desired level (e.g., score above a desired level), the barrier 220 can be moved toward the trainee 8 to increase the difficulty of the exercise. If the trainee 8 fails to improve to a desired level (e.g., score remains below a desired level), the barrier 220 can be moved away the trainee 8 (or removed) to decrease the difficulty of the exercise.

The segmenting training 118 configuration of FIG. 14F can also be used to play a Segmenting Game that is similar to the one described above regarding FIG. 14F. The delivery device 20 can be used to project objects 30 as desired toward the trainee 8 in front of a target zone 50 for a predetermined number of objects 30 along a set of predetermined trajectories initially without a screen 51 positioned between the trainee 8 and the delivery device 20. The controller 28, 29 can determine the score of the trainee 8 for interacting with the objects 30. The next trainee 8 can then step up in front of the target zone 50 and interact with another set of objects 30 projected to the next trainee 8 along the set of predetermined trajectories. The controller 28, 29 can determine the score for the next trainee 8 for their interaction with the objects 30.

This process can be repeated for all trainees 8 that are participating in the game. With that score tallied for each trainee 8, a screen S1 can be moved to position 220'. Each trainee 8 can then take their turn in interacting with another set of objects projected along another set of predetermined trajectories that can travel above, below, beside, or through the screen S1. Scores for each trainee 8 can be determined by the controller 28, 29 with screen 51 at distance L8 from the trainee 8. For the next round, the screen S1 can be moved to position 220" which is closer to the trainee 8. Each trainee 8 can then take their turn in interacting with another set of objects projected along another set of predetermined trajectories that can travel above, below, beside, or through the screen 51. Scores for each trainee 8 can be determined by the controller 28, 29 with screen 51 at distance L8 from the trainee 8. It should be understood that many more positions of the screen 51 can be used to create additional rounds of the game.

The game can also include deducting points from a trainee's score if an object gets past the trainee 8 and impacts the target zone 50. Additionally, the target zone may include a wicket 212 that causes more damage to the trainee's score if one or more of the objects 30 impacts the wicket 212. Many versions of this game are envisioned, yet the main activity can remain, which is successively altering the distance the trainee 8 has to recognize the object 30 as it proceeds toward the trainee 8 or target zone 50, and the trainee 8 attempting to deflect the object 30 away from the target zone 50 or to capture the object 30, preventing impact with the target zone 50.

In any of the segmenting training 118 methods, the screens 220, 51, S2 can be various colors to provide varied complications in recognizing the object 30 against a backdrop of the screen 220, 51, S2. In a non-limiting embodiment, the screen 220, 51, S2 can be black, brown, various shades of brown, white, various shades of white, a mix of colors (e.g., camouflage colors), blue, various shades of blue, red, various shades of red, yellow, various shades of yellow, green, and various shades of green.

Figure 15:
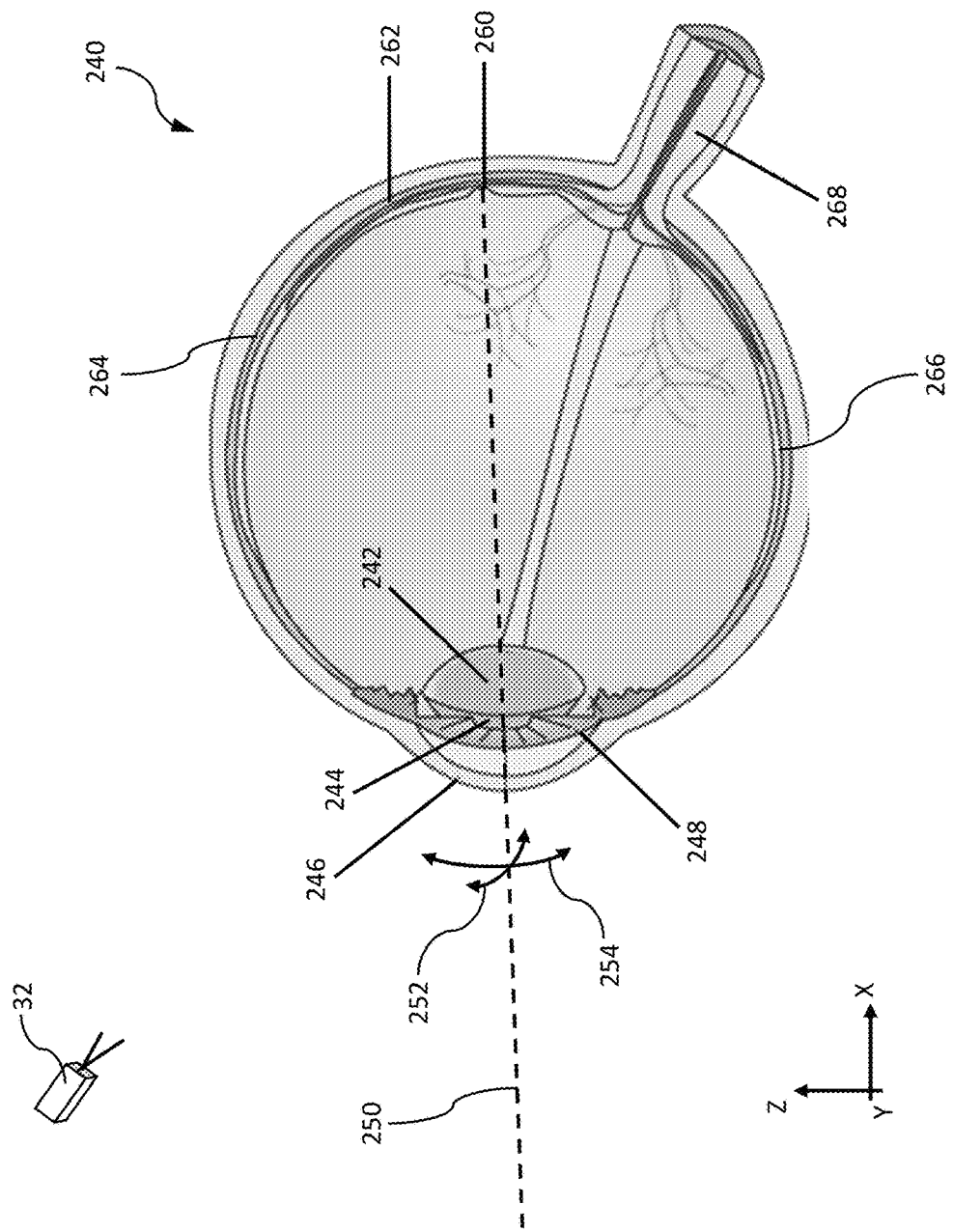
FIG. 15 is a representative partial cross-sectional view of a trainee's eye and a camera used to detect and track the trainee's center line of sight (or fovea vision), in accordance with certain embodiments.

FIG. 15 is a representative partial cross-sectional view of a trainee's eye 240 and an imaging sensor 32 that can capture the movement of the eye 240. The imaging sensor 32 can collect imagery of the eye and transmit the imagery to the controller 28, 29, which can analyze the imagery to determine the movements of the eye 240 and track the trainee's center line of sight 250 (or fovea vision) or detect other eye movement characteristics (e.g., movement of the lens, iris, or pupil during focusing of the eye. The center line of sight 250 is represented as a line drawn from the fovea 260 of the eye 240 through the center of the pupil 244 and extending outward. As the eye 240 moves within an eye socket (not shown here for clarity) the center line of sight 250 will move accordingly (arrows 252, 254).

The retina 262 detects light received through the lens 242, the pupil 244, the cornea 246, and the iris 248. The received light can be captured by the retina 262 and transmitted to the brain (not shown) via the optical nerve 268. The trainee's brain can then interpret imagery from the eye 240 of the surroundings viewed by the trainee 8. The fovea 260 can provide the clearest imagery collected by the eye 240. The remaining parts 264, 266 of the retina 262 can provide peripheral vision, which may not be as clear as the fovea vision (or center line of sight). Therefore, tracking the center line of sight 250 of the trainee 8 during training sessions and correlating it to the object 30 as the object 30 travels along a trajectory (e.g., trajectory 40) can provide the most accurate representation of the performance of the trainee 8 to correctly track the object 30 along the trajectory.

Figure 16:
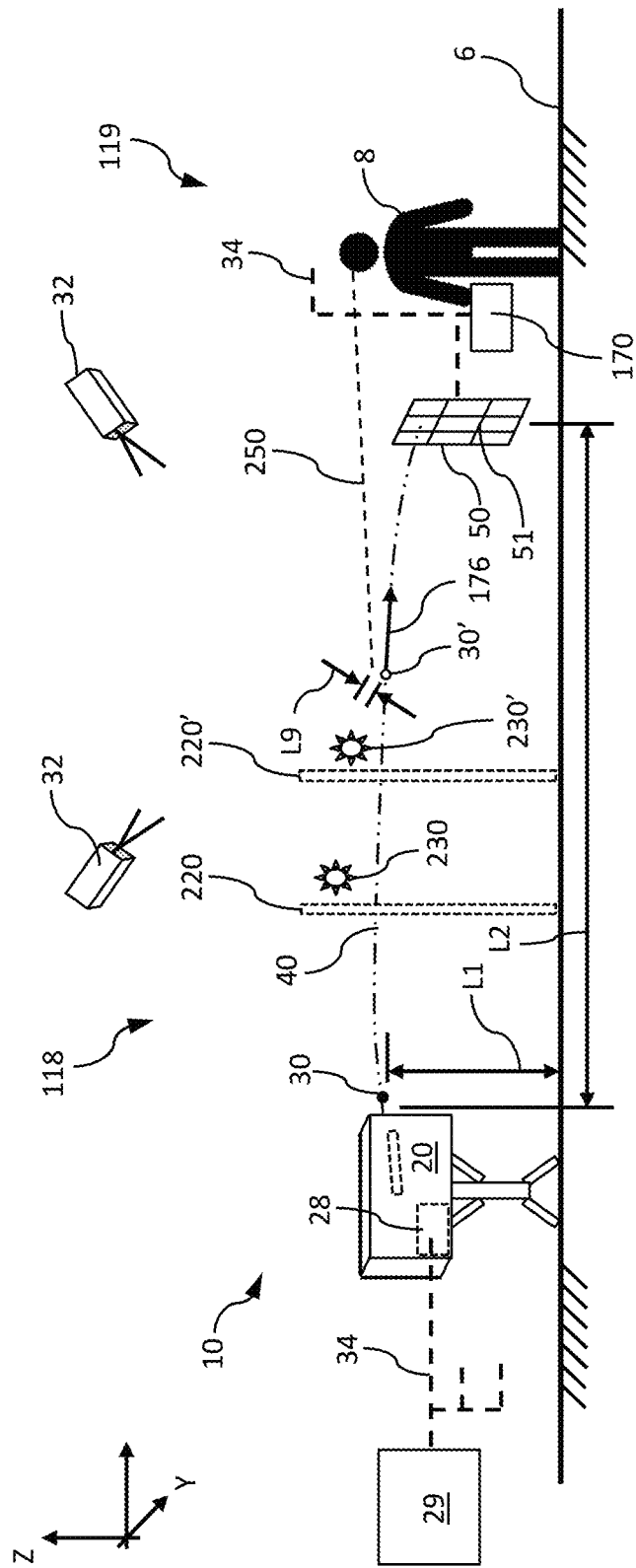
FIG. 16 is a representative functional diagram of a system and method for tracking eye movement of a trainee and comparing it to a trajectory of an object, in accordance with certain embodiments.

FIG. 16 is a representative functional diagram of a system and method for tracking the movement of a trainee's eye 240 (or eyes) and comparing it to a trajectory 40 of an object 30. Imaging sensors 32 can be used to collect imagery of the object 30 as it travels along the trajectory 40 as well as tracking eye characteristics of the trainee's eye 240 as well as the time these occur. The eye characteristics can include a direction of the center line of sight (or fovea vision or central vision) of an eye 240 of the trainee 8, movement of the eye 240 in an eye socket, movement of an iris 248 of the eye 240, size of a pupil 244 of the eye 240, and combinations thereof.

For example, as the object 30 is projected along the trajectory 40, the trainee 8 can attempt to track the object 30 with their eyes. As the object 30 continues along the trajectory 40 the trainee 8 can continue to move their eyes 240 to track the object 30. The imaging sensors 32 can be used to capture imagery that contains the trajectory 40 of the object and the movements of the eye (or eyes) 240 and a time stamp of the movements. The imagery can be transmitted to the controller 28, 29 which can be configured to analyze the trajectory 40 to determine the parameters of the trajectory 40, such as the 3D position of the object 30 in space along the trajectory 40 and the velocity vectors (e.g., 176) of the object 30 as it traveled along the trajectory 40.

The controller 28, 29 can also be configured to analyze the recorded eye movements of the trainee's eye 240 to determine the direction from the eye 240 of the center line of sight 250 of the eye 240. At any position along the trajectory 40 (such as position 30'), the controller 28, 29 can correlate the object position along the trajectory 40 with the eye movements based on syncing the time of the position of the object 30 along the trajectory 40 (e.g., position 30') with the time of the eye movements of the trainee 8. With the center line of sight 250 is correlated to the object position (e.g., 30'), then the controller 28, 29 can calculate a deviation L9 between the object 30 and the center line of sight 250. Calculating a deviation L9 for multiple positions along the trajectory 40 can be used to score the ability of the trainee 8 to track the object 30 along the trajectory 40. The larger the deviation L9, the lower the score. The deviations L9 can be plotted vs. time to display to the user (trainee 8, coach 4, another individual, etc.) for understanding areas of strength or weakness of the trainee 8 in tracking the object 30 along the trajectory 40.

The method for tracking movement of a trainee's eye 240 (or eyes) and correlating the eye movement to the positions of the object 30 along the trajectory (e.g., 40) can be used with any of the training systems 10 described in this disclosure. For example, during segmenting training 118, the correlation between the trajectory 40 and the eye movement can be used to score the trainee's ability to track the object 30 through the end portion of the trajectory 40 that can be reduced (e.g., barrier 220 and possibly the light source 230 moved to respective positions 220', 230') as the score is improved, or increased (e.g., barrier 220 and possibly the light source 230 moved to original positions) as the score is unchanged or worse.

It should also be understood that a coach 4 or another individual can score the ability of the trainee 8 to track the object 30 along the trajectory 40 by visually observing the trainee 8 as they attempt to track the object 30. This can be seen as being somewhat less precise than the method of correlating the eye movements to the object positions along the trajectory 40 using the controller 28, 29. However, this manual correlation can also be used to improve the trainee's ability to track the object 30 along the trajectory 40.

The training system 10 in FIG. 16, as well as various other training systems 10 described in this disclosure, can be used to perform strike zone training 119. Strike zone training 119 can be used to improve an ability of the trainee 8 to recognize objects 30 delivered to the target zone 50 (which can be referred to as a strike zone for baseball and softball sports). By using the smaller object 30 training as described herein, the trainee 8 can hone their skills for recognizing strikes and those that are not strikes.

The strike zone training 119 can occur when the delivery device 20 sequentially projects objects 30 along a predetermined trajectory (e.g., trajectory 40) and the trainee 8 indicates when they believe the object 30 arrives within the target zone 50 by providing a user input to the controller 28, 29 via an HMI device 170. The target zone 50 can include sensors 51 as previously described. These sensors 51 can detect a location in the target zone at which the object 30 arrives. The trainee 8 can actuate or interact with the HMI device 170 to indicate if they think the object 30 arrived in the target zone 50, and the HMI device can transmit the indication to the controller 28, 29, which can compare the indication with the actual arrival location of the object 30. The controller 28, 29 can also determine if the object did not arrive within the target zone 50, either due to a lack of indication from the sensors 51 that the object 30 arrived at the target zone 50 or possibly sensors (not shown) that are positioned outside the target zone 50.

A high score can be when the indication is received from the HMI device 170 and the object 30 arrives within the target zone 50, or when the object 30 does not arrive in the target zone 50 and no indication is received from the HMI device 170. A low score can be when the indication is not received from the HMI device 170 and the object 30 arrives within the target zone 50, or when the object 30 does not arrive in the target zone 50 and an indication is received from the HMI device 170.

The controller 28, 29 can average the individual scores over a period of time or over multiple objects 30 delivered toward the target zone 50. This average score can be used (as well as the individual scores) can be used to provide feedback to the trainee 8 (or the coach 4, another individual, or the controller 28, 29) for improving the trainee's performance of recognizing objects 30 arriving in the target zone 50 and those that do not arrive in the target zone 50. Training with the smaller object 30 can allow the trainee 8 to recognize regulation game objects 130 even easier during a real-life event and thereby more easily recognize balls and strikes in the real-life event. This training 119 can be well suited for baseball, softball, cricket, or any sport with a strike zone like target area for receiving a game object 130. However, the strike zone training 119 can also be used for other not as well-suited sports or tactical situations to improve the hand-eye coordination of a trainee 8.

The strike training 119 can also be used to improve the trainee's ability to recognize when the object 30 arrives at the target zone 50. So the trainee 8 can send an indication via the HMI device 170 to the controller 28, 29 when they believe the object 30 arrives at the target zone 50. The controller 28, 29, via comparison to the sensor data received from the sensors 51, can determine a score based on the comparison of the time of arrival of the object 30 at the target zone 50 and when the indication is initiated at the HMI device 170 by the trainee 8.

The indication from the HMI device 170 can be initiated by:
  body movement of the trainee 8;
  eye movement of the trainee 8;
  hand movement of the trainee 8;
  leg movement of the trainee 8;
  arm movement of the trainee 8;
  head movement of the trainee 8;
  audible sound signal from the trainee 8;
  movement of a sports tool 12;
  actuation of a key on a keyboard;
  actuation of a switch;
  trainee 8 interaction with the HMI device 170; or
  combinations thereof.

Additionally, a good performance of the trainee 8 regarding the object 30 can be when the actual arrival position is inside the target zone and the indication is received from the HMI device 170 within a pre-determined amount of time before the actual arrival time, or when the actual arrival position is outside the target zone and no indication is received from the HMI device within a pre-determined amount of time before the actual arrival time. A bad performance of the trainee 8 regarding the object 30 can be when the actual arrival position is outside the target zone and the indication is received from the HMI device 170, or when the actual arrival position is inside the target zone and no indication is received from the HMI device 170, or when the actual arrival position is inside the target zone and the indication is received from the HMI device 170 past a pre-determined amount of time prior to the actual arrival time.

During the various training methods described in this disclosure, the trainee 8 (or coach 4) can use gestures to initiate projection of the next object 30 along a predetermined trajectory (e.g., trajectory 40). For example, one particular type of gesture is a stride step in baseball. The stride step can be taken as the batter in baseball, softball, or possibly cricket steps toward a game object 130 as the game object travels toward the target zone 50.

Figure 17:
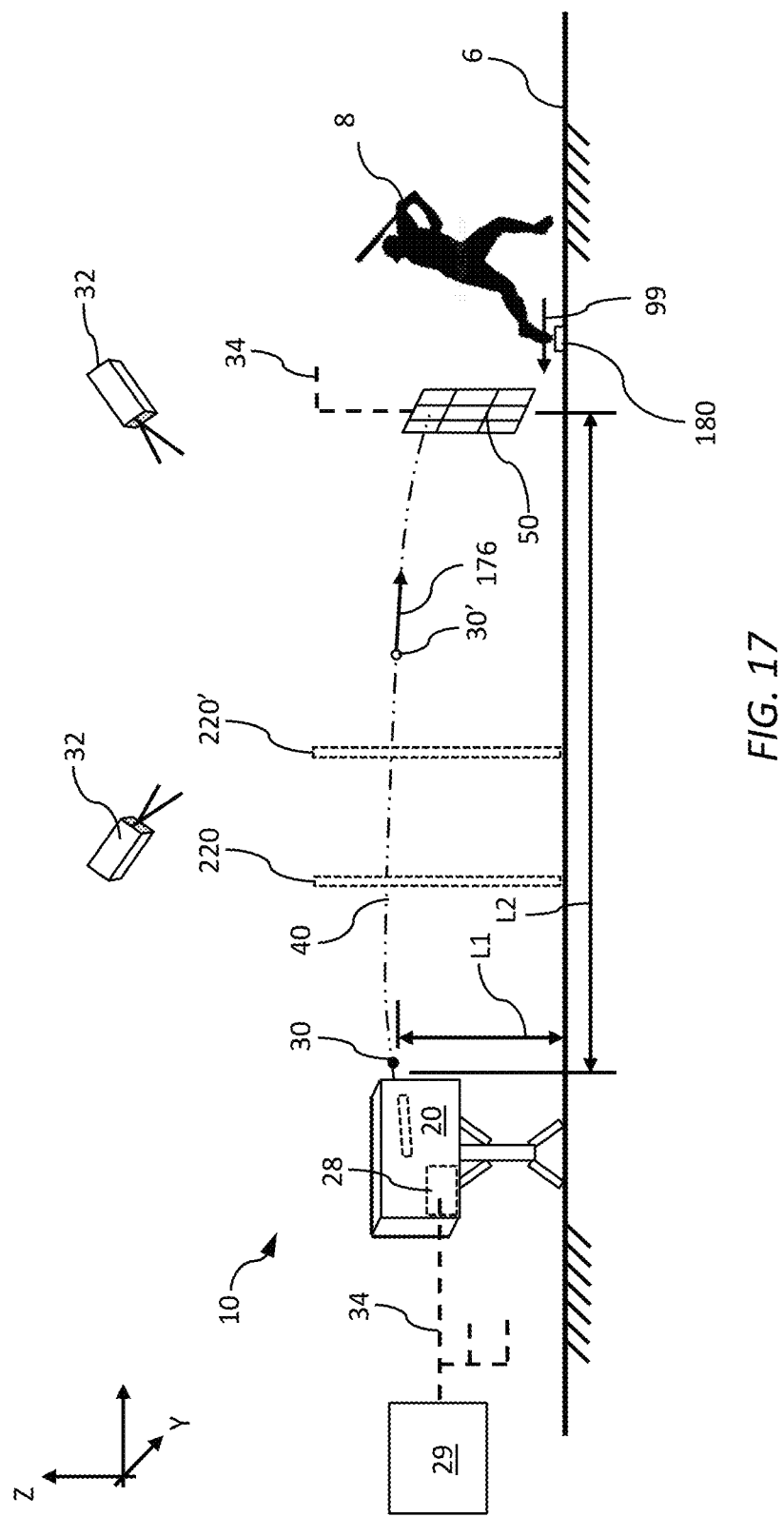
FIG. 17 is a representative functional diagram of a system and method for delivering an object along a trajectory to a target zone with the object delivery being initiated via a stride sensor, in accordance with certain embodiments.

As seen in FIG. 17, the trainee 8 can step toward the delivery device 20 to initiate the projection of the next object 30. As the trainee 8 moves their front foot toward the delivery device 20, they can activate a stride sensor 180, which can send an activation signal to the controller 28, 29, which can initiate projection of the next object 30 along a predetermined trajectory (e.g., trajectory 40). In this way, the trainee 8 can control the timing when the next object 30 is projected toward the target zone 50. It should be understood that other gestures can be used to send the activation signal to the controller 28, 29. Other possible gestures can be body movement of the trainee 8, eye movement of the trainee 8, hand movement of the trainee 8, leg movement of the trainee 8, arm movement of the trainee 8, head movement of the trainee 8, audible sound signal from the trainee 8, movement of a sports tool 12, actuation of a key on a keyboard, actuation of a switch, trainee interaction with the HMI device 170, or combinations thereof.

Figure 18:
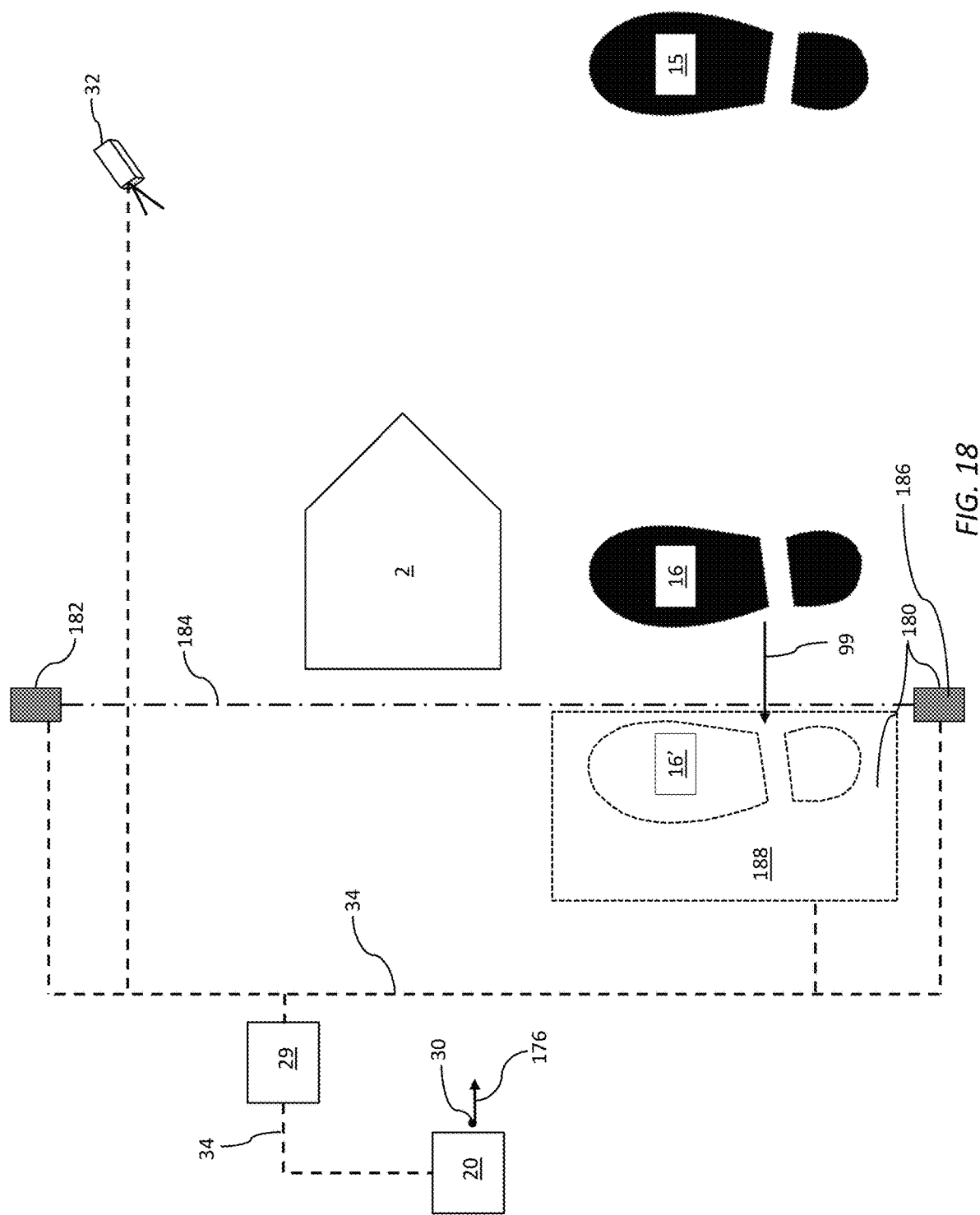
FIG. 18 is a representative functional diagram of a system and method for activating a stride sensor, in accordance with certain embodiments.

FIG. 18 is a representative functional diagram of a system and method for activating a stride sensor 180. Foot positions of a right-handed trainee 8 are shown, but it should be understood that the description applies equally to foot positions of a left-handed trainee 8. The trainee 8 can position their feet at positions 15, 16 at a home plate 2 prior to initiating projection of the next object 30. When the trainee 8 wishes to initiate projection of the next object 30, the trainee 8 can stride the front foot from position 16 to position 16'. This motion (arrows 99) can cause the foot or other portion of the trainee's leg to activate the stride sensor 180. For example, the stride sensor 180 can be a pressure plate 188 that the stride foot can contact or depress in position 16', which can cause the activation signal to be sent to the controller 28, 29. Alternatively, or in addition to, the stride sensor 180 can be a light source 182 that transmits a light signal 184 to a light receiver 186. The stride foot can break the light signal 184 when moving from position 16 to position 16', thereby causing the activation signal to be sent to the controller 28, 29. Alternatively, or in addition, an can detect movement of one or more body parts of the trainee 8 (including the stride foot) and transmit imagery to the controller 28, 29, which can determine a gesture of the trainee 8 and, based on the detection, can initiate projection of the next object 30.

FIG. 19 is a representative functional diagram of a system and method for activating a sensor 180. The trainee 8 can position their feet at positions 15, 16 behind a sensor 180 (relative to the delivery device 20) prior to initiating projection of the next object 30. When the trainee 8 wishes to initiate projection of the next object 30, the trainee 8 can move either foot or leg (or arm, or body, or sports tool, etc.) the left foot from position 16 to position 16'. This motion (arrows 99) can cause the left foot or other portion of the trainee's leg to activate the sensor 180. For example, sensor 180 can be a pressure plate 188 that the left foot can contact or depress in position 16', which can cause the activation signal to be sent to the controller 28, 29. Alternatively, or in addition to, the sensor 180 can be a light source 182 that transmits a light signal 184 to a light receiver 186. The left foot can break the light signal 184 when moving from position 16 to position 16', thereby causing the activation signal to be sent to the controller 28, 29. Alternatively, the right foot can break the light signal 184 when moving from position 15 to position 15', thereby causing the activation signal to be sent to the controller 28, 29. Alternatively, or in addition, the imaging sensor 32 can detect movement of one or more body parts of the trainee 8 (including either foot) and transmit imagery to the controller 28, 29, which can determine a gesture of the trainee 8 and, based on the detection, can initiate projection of the next object 30.

Various Embodiments

Embodiment 1. A method comprising:
providing an object having a size smaller than a size of a known regulation object;
projecting the object, via a delivery device, toward a trainee; and training the trainee to follow the object.

Embodiment 2. The method of embodiment 1, wherein the projecting further comprises projecting a plurality of objects in series, one after another in time, along predetermined trajectories and scoring a capability of the trainee to track each object of the plurality of objects along at least a portion of the predetermined trajectories.

Embodiment 3. The method of embodiment 2, further comprising:
scoring a correlation of eye movement of the trainee with the movement of each object of the plurality of objects along at least the portion of the predetermined trajectories.

Embodiment 4. The method of embodiment 2, further comprising:
capturing imagery with one or more imaging sensors;
analyzing the imagery; and
scoring a correlation of eye movement of the trainee with the movement of each object of the plurality of objects along at least the portion of the predetermined trajectories.

Embodiment 5. The method of embodiment 4, adjusting the projecting of the object to improve the accuracy of the projecting to project the object along the predetermined trajectories.

Embodiment 6. The method of embodiment 4, adjusting the performance of the trainee based on the scoring, thereby improving the capability of the trainee to track each object of the plurality of objects along at least a portion of the predetermined trajectories.

Embodiment 7. The method of embodiment 6, wherein the portion of the predetermined trajectories is at least 10 feet, or at least 15 feet, or at least 20 feet, or at least 25 feet, or at least 30 feet, or at least 35 feet, or at least 40 feet, or at least 45 feet, or at least 50 feet, or at least 55 feet.

Embodiment 8. The method of embodiment 6, wherein the predetermined trajectories are toward a location proximate to the trainee.

Embodiment 9. The method of embodiment 1, wherein the training further comprises tracking eye moment of the trainee as the trainee visually observes the object moving along a predetermined trajectory from a delivery device to a target zone, scoring the tracking, and communicating the scoring to the trainee or a coach or a computer storage device.

Embodiment 10. The method of any one of embodiments 3 to 9, wherein the scoring comprises at least one of:
measuring the movement of eyes of the trainee and comparing the measurement to expected movement of the eyes when tracking the object;
measuring the movement of a head of the trainee and comparing the measurement to expected movement of the head when tracking the object; and
measuring the movement of another portion of the trainee and comparing the measurement to the expected movement of the portion when tracking the object.

Embodiment 11. The method of embodiment 10, wherein projecting of a subsequent object is adapted based on the scoring.

Embodiment 12. The method of embodiment 11, wherein a characteristic of the subsequent object is determined based on the scoring, and wherein the characteristic comprises one of a trajectory, size, color, shape, surface features, weight, and combinations thereof.

Embodiment 13. The method of embodiment 10, further comprising rating a performance of the trainee based on the scoring.

Embodiment 14. The method of embodiment 10, further comprising adapting the training based on the scoring.

Embodiment 15. The method of embodiment 10, wherein performance of the trainee is improved by sharing the scoring with the trainee.

Embodiment 16. The method of embodiment 10, further comprising selecting a projection of a subsequent object based on the scoring.

Embodiment 17. The method of embodiment 10, further comprising recording the measurements and the scoring being based on the recording.

Embodiment 18. The method of embodiment 1, wherein projecting the object toward the trainee is conducted to train the trainee to follow the object along a predetermined trajectory.

Embodiment 19. The method of embodiment 18, wherein the training comprises scoring a capability of the trainee to follow the object along the predetermined trajectory.

Embodiment 20. The method of embodiment 1, wherein projecting the object further comprises projecting the object along an actual trajectory, the method further comprising:
comparing the actual trajectory to an expected trajectory;
scoring the actual trajectory based on the comparing; and
adjusting the delivery device, based on the scoring, to project a next object substantially along the expected trajectory.

Embodiment 21. The method of embodiment 1, wherein the projecting comprises projecting the object toward an impact device, and wherein the training comprises the trainee striking the impact device in response to the projecting of the object toward the impact device.

Embodiment 22. The method of embodiment 21, further comprising impacting a target zone on one side of the impact device with the object.

Embodiment 23. The method of embodiment 22, wherein the target zone is divided into target segments and the projecting delivers the object to a desired one of the target segments.

Embodiment 24. The method of embodiment 23, wherein the projecting projects the object along a predetermined trajectory from the delivery device to a predetermined one of the target segments.

Embodiment 25. The method of embodiment 22, further comprising the trainee impacting an impact zone on an opposite side of the impact device with a sport tool.

Embodiment 26. The method of embodiment 25, further comprising:
sensing, via sensors in the target zone, a first time when the object impacts the target zone;
sensing, via sensors in the impact zone, a second time when the sport tool impacts the impact zone;
comparing the first time to the second time; and
scoring a performance of the trainee based on the comparing.

Embodiment 27. The method of embodiment 25, further comprising:
sensing, via sensors in the target zone, a segment in the target zone that captures the object when the object impacts the segment;
sensing, via sensors in the impact zone, a position of the impact of the sport tool when the sport tool impacts the impact zone;
spatially comparing the segment with the position of the impact of the sport tool; and
scoring a performance of the trainee based on the spatial comparison.

Embodiment 28. The method of embodiment 25, further comprising:
sensing, via sensors in the target zone, a segment in the target zone that captures the object when the object impacts the segment; and
adapting the delivery device for projecting another object toward the target zone.

Embodiment 29. The method of embodiment 1, wherein the projecting further comprises projecting a plurality of objects in series, one after another in time, along predetermined trajectories, wherein the predetermined trajectories emulate:
a sequence of pitches in baseball, or
a sequence of pitches in softball, or
a sequence of shots on goal in hockey, or
a sequence of volleys in tennis, or
a sequence of throws in lacrosse, or
a sequence of pitches in cricket, or
a sequence of ball kicks in soccer, or
a sequence of serves in table tennis.

Embodiment 30. The method of embodiment 1, wherein the object is spherically shaped, and wherein a difference in a size of the object compared to a size of a regulation object is at least 0.001, or at least 0.002, or at least 0.004, or at least 0.006, or at least 0.008, or at least 0.01, or at least 0.02, or at least 0.03, or at least 0.05, or at least 0.07, or at least 0.1, or at least 0.15, or at least 0.2, or at least 0.25, or at least 0.3.

Embodiment 31. The method of embodiment 1, wherein a difference in size of the object compared to a regulation object is at least 0.001, and wherein the size of the object is measured by a longest dimension of the object as compared to a longest dimension of the regulation object.

Embodiment 32. The method of embodiment 31, wherein the regulation object comprises one of a regulation baseball, a regulation softball, a regulation hockey puck, a regulation tennis ball, a regulation lacrosse ball, a regulation cricket ball, a regulation football, and a regulation soccer ball.

Embodiment 33. A system comprising:
a device configured to project an object at a target or a trainee, the object having a size smaller than a corresponding regulation object; and
at least one of:
a computer storage device communicatively coupled to the device and configured to receive data and adapt a delivery of the object or a subsequent object;
an alert feature on or near the device or on or near the trainee configured to alert the trainee to a timing of projection of the object from the device;
an impact device configured to receive and capture the object;
a sensor configured to record and/or score an interaction of the trainee to the object;
a Spread Diameter of not greater than 12 inches for at least 10 consecutive objects according to a same predetermined trajectory over a distance of at least 20 feet;
a Spread Precision Ratio (SD/Dd) of not greater than 0.9 in/ft, wherein SD is the Spread Diameter (inches), which is the maximum distance between any two objects from 10 consecutive objects projected over a delivery distance (Dd) of 20 feet; and or any combination of two or more elements of a), b), c), d), e), and f).

Embodiment 34. The system of embodiment 33, wherein the device is configured to be used according to any method embodiment disclosed or described herein.

Embodiment 35. The system of embodiment 33, wherein the device further includes one or more controllers capable of controlling various aspects of a process of projection of the object, such that the projection is conducted along a predetermined trajectory.

Embodiment 36. The system of embodiment 35, wherein the controllers are configured to actuate one or more actuators configured to control a position of the device and adapt the delivery of the object according to a predetermined trajectory.

Embodiment 37. The system of embodiment 33, wherein the device includes any of the features embodied or described in embodiments herein.

Embodiment 38. The system of embodiment 33, wherein the device can include or be communicatively coupled (wired or wirelessly) to one or more computing devices that are communicatively coupled to one or more controllers configured to control one or more delivery variables associated with delivering the object along a predetermined trajectory.

Embodiment 39. The system of embodiment 38, wherein the delivery variables are selected from the group; a position of the device in 3D-space (position in space according to X, Y, and Z planes), angle of the device relative to an intended target or trainee, distance from a target or trainee, intended velocity of the object anywhere along the predetermined trajectory between the device and the target or trainee, spin of the object anywhere along the predetermined trajectory between the device and the target or trainee, weight of the object, surface features of the object, and others.

Embodiment 40. The system of embodiment 33, wherein the device includes a guide configured to interact with the object and impart a spin to the object for delivery of the object according to a predetermined trajectory.

Embodiment 41. The system of embodiment 40, wherein the system is configured to deliver at least 10 consecutive objects according to a same predetermined trajectory over a distance of at least 20 feet with a Spread Diameter of not greater than 11 inches or not greater than 10 inches or not greater than 9 inches or not greater than 8 inches or not greater than 7 inches or not greater than 6 inches or not greater than 5 inches or not greater than 4 inches or not greater than 3 inches or not greater than 2 inches or not greater than 1.5 inches or not greater than 1 inch.

Embodiment 42. The system of embodiment 40, wherein the system has a Spread Precision Ratio (SD/Dd) of not greater than 0.9 in/ft, wherein SD is the Spread Diameter (inches), which is a maximum distance between any two objects from 10 consecutive objects projected over the delivery distance (Dd) of 20 feet, wherein the Spread Precision Ratio (SD/Dd) is not greater than 0.8 in/ft or not greater than 0.75 in/ft or not greater than 0.70 in/ft or not greater than 0.65 in/ft or not greater than 0.60 in/ft or not greater than 0.55 in/ft or not greater than 0.5 in/ft or not greater than 0.45 in/ft or not greater than 0.40 in/ft or not greater than 0.35 in/ft or not greater than 0.3 in/ft or not greater than 0.25 in/ft or not greater than 0.2 in/ft or not greater than 0.15 in/ft or not greater than 0.1 in/ft or not greater than 0.05 in/ft or not greater than 0.03 in/ft or not greater than 0.02 in/ft or not greater than 0.01 in/ft.

Embodiment 43. The system of embodiment 42, wherein the Spread Precision Ratio (SD/Dd) is at least 0.0001 in/ft or at least 0.0005 in/ft or at least 0.001 in/ft or at least 0.005 in/ft or at least 0.01 in/ft.

Embodiment 44. A method for sports training comprising:
  determining game parameters of a game trajectory of a sports object that was projected along the game trajectory in a real-time sports event; and
  based on the game parameters, adapting a delivery device to deliver a training object along a training trajectory that mimics at least a portion of the game trajectory, wherein the training object is smaller than the sports object.

Embodiment 45. The method of embodiment 44, the training trajectory mimics a distal end portion of the game trajectory proximate to a target, wherein a length of the distal end portion is shorter than an overall distance along the game trajectory.

Embodiment 46. The method of embodiment 45, wherein the length of the distal end portion is less than 50% of the overall distance along the game trajectory.

Embodiment 47. The method of embodiment 45, wherein the length of the distal end portion is less than 40%, or less than 30%, or less than 25%, or less than 20%, or less than 15%, or less than 10% of the overall distance along the game trajectory.

Embodiment 48. The method of embodiment 45, further comprising:
  converting the game parameters of the game trajectory to delivery device parameters;
  receiving the delivery device parameters at a controller;
  adapting the delivery device, based on the delivery device parameters, to deliver the training object along a training trajectory; and
  projecting the training object along the training trajectory.

Embodiment 49. The method of embodiment 48, further comprising:
  repeatedly delivering, via the delivery device, the training object along the training trajectory; and
  repeatedly delivering the training object within a grouping with a diameter that is less than 2 inches, or less than 1 inch, or less than 0.5 inches, or less than 0.1 inches at a target.

Embodiment 50. The method of embodiment 48, wherein determining the game parameters comprises one of:
  determining the game parameters from a statistics database which includes statistics of the real-time sports event;
  determining the game parameters from historical video clips of the real-time sports event;
  tracking the game trajectory during the real-time sports event, determining the game parameters for the game trajectory, and sending the game parameters to the controller;
  tracking the game trajectory during the real-time sports event, determining the game parameters for the game trajectory, and sending the game parameters to the controller in real-time;
  tracking the game trajectory via a tracking device during the real-time sports event, determining the game parameters for the game trajectory, storing the game parameters in a non-transitory memory, and retrieving, via the controller, the game parameters from the tracking device;
  tracking the game trajectory via a tracking device during the real-time sports event, determining the game parameters for the game trajectory, and retrieving, via the controller, the game parameters from the tracking device;
  tracking the game trajectory via a tracking device during the real-time sports event, determining the game parameters for the game trajectory, and retrieving, via the controller, the game parameters from the tracking device in real-time;
  collecting the game parameters from one or more data sources and sending the game parameters to the controller;
  retrieving, via the controller, the game parameters from a database; and
  combinations thereof.

Embodiment 51. The method of embodiment 50, wherein the tracking device is an imaging system that captures imagery of the game trajectory, determines the game parameters from an analysis of the imagery, and sends the game parameters to the delivery device in response to a transfer request received by the imaging system.

Embodiment 52. The method of embodiment 48, wherein the delivery device parameters comprise one or more of:
  air pressure supplied to the training object to propel the training object through a barrel with a center axis;
  air volume supplied to the training object;
  inclination of the barrel;
  azimuthal orientation of the barrel;
  length of the barrel;
  barrel selection;
  inclination of a friction device that comprises a ramp and a surface material on the ramp;
  azimuthal orientation of the friction device around the center axis of the barrel;
  azimuthal orientation of the friction device around a longitudinal axis of the friction device;
  length of the friction device;
  the surface material of the friction device;
  object launch position from the delivery device, the training object launch position being a location in 3D space of an X-Y-Z coordinate system;
  object selection;
  height of the delivery device;
  inclination of the delivery device;
  azimuthal orientation of the delivery device;
  distance to a target zone; and
  height of the target zone.

Embodiment 53. The method of embodiment 44, wherein the game parameters comprise one or more of:
  a spin of the sports object,
  a speed of the sports object
  a weight of the sports object,
  a size of the sports object,
  a surface texture of the sports object,
  a trajectory of the sports object through a 3D space of an X-Y-Z coordinate system, and
  combinations thereof.

Embodiment 54. The method of embodiment 44, wherein the game trajectory comprises a plurality of game trajectories, wherein the determining comprises determining game parameters for each of the game trajectories to create a plurality of game parameters, wherein the adapting comprises adapting the delivery device, based on the plurality of game parameters, to deliver each one of a plurality of training objects along one of a plurality of training trajectories, and wherein each one of the plurality of training trajectories mimics at least a portion of one of the plurality of game trajectories.

Embodiment 55. The method of embodiment 54, wherein the real-time sports event is a baseball game, and the plurality of training trajectories mimics a sequential set of pitches thrown by a pitcher during the baseball game.

Embodiment 56. The method of embodiment 54, wherein the real-time sports event is a baseball practice, and the plurality of training trajectories mimics a sequential set of pitches thrown by a pitcher during the baseball practice.

Embodiment 57. The method of embodiment 54, wherein the real-time sports event is a hockey game, and the plurality of training trajectories mimics a sequential set of shots on the goal of a hockey player toward the goal during the hockey game.

Embodiment 58. The method of embodiment 54, wherein the real-time sports event is a tennis match, and the plurality of training trajectories mimics a sequential set of volleys hit from a first player to a second player during the tennis match.

Embodiment 59. The method of embodiment 54, wherein the real-time sports event is a softball game, and the plurality of training trajectories mimics a sequential set of pitches thrown by a pitcher during the softball game.

Embodiment 60. The method of embodiment 44, wherein the real-time sports event is any one of regulation sports described in the specification.

Embodiment 61. A system for training a trainee in performing a sport, the system comprising:
 a delivery device that projects an object toward a target along a trajectory;
 a sensor that is configured to detect eye characteristics of the trainee, wherein the trainee is configured to track the object; and
 a computing system configured to determine a score of the trainee based upon the detected eye characteristics.

Embodiment 62. The system of embodiment 61, wherein the sensor is an imaging system that captures imagery of the trainee and analyzes the imagery to determine the eye characteristics of the trainee.

Embodiment 63. The system of embodiment 62, wherein the imaging system comprises a human that is separate from the trainee.

Embodiment 64. The system of embodiment 62, wherein the imaging system comprises a controller and an imaging sensor.

Embodiment 65. The system of embodiment 64, wherein the imaging sensor comprises:
 a camera;
 a 2D camera;
 a 3D camera;
 a light detection and ranging (LiDAR) sensor; or combinations thereof.

Embodiment 66. The system of embodiment 61, wherein the eye characteristics comprise:
 direction of line of sight of an eye of the trainee;
 direction of fovea vision of the eye;
 direction of central vision of the eye;
 movement of the eye in an eye socket;
 movement of an iris of the eye;
 movement of a pupil of the eye;
 size of the pupil of the eye; and
 combinations thereof.

Embodiment 67. The system of embodiment 61, wherein the eye characteristics comprise a direction of a central vision of an eye of the trainee, and wherein the computing system is configured to compare the trajectory of the object to the direction of the central vision of the eye as the trainee tracks the object along at least a portion of the trajectory.

Embodiment 68. The system of embodiment 67, wherein the score is based on the comparison of the trajectory and the direction of the central vision of the eye.

Embodiment 69. The system of embodiment 68, wherein the computing system controls various aspects of the delivery device to project the object along the trajectory to improve a performance of the trainee in the sport, wherein the object has a size that is smaller than a corresponding regulation object for the sport.

Embodiment 70. The system of embodiment 61, wherein the computing system is configured to detect an X-Y-Z location of the object in a three-dimensional (3D) space in an X-Y-Z coordinate system as the object travels along the trajectory.

Embodiment 71. The system of embodiment 70, wherein the computing system captures the eye characteristics of an eye of the trainee as the trainee tracks the object along the trajectory, and wherein the computing system determines the score of an ability of the trainee, based on the eye characteristics, to track the object along at least a portion of the trajectory.

Embodiment 72. The system of embodiment 61, further comprising a light source that illuminates the object for at least a portion of the trajectory.

Embodiment 73. The system of embodiment 72, wherein the light source is an ultra-violet light source, and the object is constructed from a luminescent material.

Embodiment 74. A method for sports training comprising:
 projecting, via a delivery device, an object toward a target along an actual trajectory;
 tracking the object along at least a portion of the actual trajectory;
 comparing the portion of the actual trajectory to a corresponding portion of a desired trajectory; and
 adjusting one or more parameters of the delivery device based on the comparing.

Embodiment 75. The method of embodiment 74, wherein the projecting further comprises propelling the object through a barrel via applying a volume of air at a given air pressure to the object at one end of the barrel and propelling the object through the barrel past a second end of the barrel in response to the applying of the volume of air to the object, thereby projecting the object along the actual trajectory.

Embodiment 76. The method of embodiment 75, wherein the projecting further comprises the object impacting a friction device after exiting the second end of the barrel, the friction device comprising a ramp with a surface material, wherein the friction device is tiltable with respect to a center axis of the barrel and is rotatable about the center axis of the barrel.

Embodiment 77. The method of embodiment 76, further comprising tilting the friction device relative to the center axis to a tilt position and rotating the friction device around the center axis to an azimuthal orientation; and imparting a spin and a deflection to the object when the object impacts the friction device, thereby projecting the object along the actual trajectory.

Embodiment 78. The method of embodiment 74, further comprising scoring a performance of the delivery device to deliver the object along the desired trajectory.

Embodiment 79. The method of embodiment 78, further comprising adjusting the one or more parameters of the delivery device when the scoring is below a pre-determined value, thereby improving the scoring to be above the pre-determined value for a subsequent object projected toward the target.

Embodiment 80. The method of embodiment 74, wherein the one or more parameters comprise one or more of:
- an air pressure supplied to the object to propel the object through a barrel with a center axis;
- an air volume supplied to the object;
- an inclination of the barrel;
- an azimuthal orientation of the barrel;
- a length of the barrel;
- an inclination of a friction device which comprises a ramp and a surface material on the ramp;
- an azimuthal orientation of the friction device around the center axis of the barrel;
- an azimuthal orientation of the friction device about a longitudinal axis of the friction device;
- a length of the friction device;
- the surface material of the friction device;
- an object launch position from the delivery device, the object launch position being a location in 3D space of an X-Y-Z coordinate system;
- an object selection;
- a distance to the target; and
- a height of the target.

Embodiment 81. The method of embodiment 74, wherein in the adjusting is performed manually or automatically.

Embodiment 82. The method of embodiment 81, wherein automatically adjusting the parameters comprises determining deviations of the actual trajectory compared to the desired trajectory; and determining changes to one or more of the one or more parameters, via a controller, that at least reduce the deviations for subsequent objects projected toward the target.

Embodiment 83. The method of embodiment 82, wherein automatically adjusting the parameters increases a score of the delivery device to a value above a pre-determined value, and wherein the score of the delivery device indicates a performance of the delivery device to project the object along the desired trajectory.

Embodiment 84. A method for sports training comprising:
- projecting, via a delivery device, an object toward a target along a trajectory;
- tracking the object along at least a distal portion of the trajectory, wherein the distal portion of the trajectory includes the object arriving at the target;
- scoring a performance score of a trainee to track the object along the distal portion of the trajectory; and
- based on the scoring, increasing or decreasing a distance of the distal portion of the trajectory along which the trainee is configured to track the object prior to the object arriving at the target.

Embodiment 85. The method of embodiment 84, wherein increasing the distance allows the trainee to have more time to track the object.

Embodiment 86. The method of embodiment 84, wherein decreasing the distance allows the trainee to have less time to track the object.

Embodiment 87. The method of embodiment 84, further comprising positioning a screen along the trajectory between the delivery device and the target, wherein a distance between the screen and the target defines the distance of the distal portion of the trajectory.

Embodiment 88. The method of embodiment 87, wherein the screen comprises an opening through which the object is projected.

Embodiment 89. The method of embodiment 88, wherein the screen blocks a view of a proximal portion of the trajectory from the trainee.

Embodiment 90. The method of embodiment 84, further comprising positioning a light source along the trajectory between the delivery device and the target, wherein a distance between the light source and the target defines the distance of the distal portion of the trajectory.

Embodiment 91. The method of embodiment 90, further comprising:
- illuminating the object with a first illumination as the object travels along a proximal portion of the trajectory; and
- illuminating the object with a second illumination as the object travels along the distal portion of the trajectory, wherein the first illumination is reduced compared to the second illumination.

Embodiment 92. The method of embodiment 91, wherein the light source is an ultra-violet light source.

Embodiment 93. A method for sports training, the method comprising any one of segmenting training methods described in the specification.

Embodiment 94. A method for sports training comprising:
- projecting, via a delivery device, an object toward an impact device along a trajectory;
- receiving the object at a target zone of the impact device;
- a trainee striking the impact device at an impact zone with a sports tool; and
- scoring a performance score of the trainee to impact the impact zone at an appropriate time compared to an arrival time of the object at the target zone.

Embodiment 95. The method of embodiment 94, wherein the scoring further comprises scoring the performance score of the trainee to impact the impact zone at an appropriate location compared to an arrival location of the object in the target zone.

Embodiment 96. The method of embodiment 94, wherein the target zone is disposed on an opposite side of the impact device from the impact zone.

Embodiment 97. The method of embodiment 94, wherein the impact device is one of:
- a support structure with a target zone on one side and an impact zone on an opposite side;
- a padded panel;
- a padded bag;
- a suspended ball;
- a ball perched on a structure;
- a suspended bag;
- a bag perched on a structure;
- a suspended puck;
- a puck perched on a structure;
- a resistance band in tension;
- a rope in tension; or
- a netting in tension.

Embodiment 98. The method of embodiment 94, further comprising detecting, via sensors, when the object arrives at the target zone.

Embodiment 99. The method of embodiment 98, further comprising detecting, via sensors, an arrival position of the object in the target zone.

Embodiment 100. The method of embodiment 99, further comprising transmitting sensor data from the sensors to a computer system, and wherein the computer system is configured to determine the performance score of the trainee based on the sensor data.

Embodiment 101. The method of embodiment 100, further comprising:
communicating the performance score, via the computing system, to a trainee;
adjusting the delivery device in response to the performance score;
projecting a subsequent object along another trajectory toward the impact device; and
determining, via the computer system, the performance score of the trainee to impact the impact zone at an appropriate time compared to an arrival time of the subsequent object at the target zone.

Embodiment 102. The method of embodiment 98, wherein the sensors comprise one or more imaging sensors.

Embodiment 103. The method of embodiment 102, further comprising:
capturing imagery, via the imaging sensors; and
transmitting the imagery to a computer system.

Embodiment 104. The method of embodiment 103, further comprising:
analyzing the imagery, via the computer system; and
determining the arrival time of the object at the target zone.

Embodiment 105. The method of embodiment 104, further comprising:
analyzing the imagery, via the computer system;
determining an impact time when the trainee impacts the impact zone with the sports tool;
comparing the impact time to the arrival time; and
determining, via the computer system, the performance score based on comparing the impact time to the arrival time.

Embodiment 106. The method of embodiment 103, further comprising:
analyzing the imagery, via the computer system;
determining an arrival location of the object at the target zone;
determining an impact location of the sports tool at the impact zone;
comparing the impact location to the arrival location; and
determining, via the computer system, the performance score based on the comparing of the impact location to the arrival location.

Embodiment 107. A method for sports training comprising:
projecting, via a delivery device, an object toward a target along a trajectory, wherein the target comprises a target zone;
receiving the object at an actual arrival position at the target, wherein the actual arrival position is either inside the target zone or outside the target zone, and wherein a trainee is configured to send an indication, via a human-machine interface (HMI) device, when the trainee expects the object to arrive inside the target zone;
comparing the indication to the actual arrival position; and
determining a performance score based on the comparing.

Embodiment 108. The method of embodiment 107, wherein a good performance of the trainee regarding the projected object is when the actual arrival position is inside the target zone and the indication is received from the HMI device, or when the actual arrival position is outside the target zone and no indication is received from the HMI device.

Embodiment 109. The method of embodiment 108, wherein a bad performance of the trainee regarding the projected object is when the actual arrival position is outside the target zone and the indication is received from the HMI device, or when the actual arrival position is inside the target zone and no indication is received from the HMI device.

Embodiment 110. The method of embodiment 109, further comprising:
projecting, via the delivery device, a plurality of objects toward the target along a plurality of trajectories;
determining, via a computing system, whether a performance of the trainee for each one of the plurality of objects is the good performance or the bad performance;
compiling, via the computing system, each of the good performances and the bad performances; and
determining the performance score based on the compiling.

Embodiment 111. The method of embodiment 107, wherein the HMI device comprises:
a button;
sensor reading;
imaging sensors;
hand-held computer system interface;
hand-held motion sensors;
motion sensors;
light pointer;
switch;
touch screen input;
audible signal;
trigger;
key stroke entry;
mouse click; or
combinations thereof.

Embodiment 112. The method of embodiment 107, wherein the indication is created via:
body movement of the trainee;
eye movement of the trainee;
hand movement of the trainee;
leg movement of the trainee;
arm movement of the trainee;
head movement of the trainee;
audible sound signal from the trainee;
movement of a sports tool;
actuation of a key on a keyboard;
actuation of a switch;
trainee interaction with the HMI device; or
combinations thereof.

Embodiment 113. The method of embodiment 107, further comprising:
receiving the object at an actual arrival time at the target;
comparing the indication to the actual arrival time; and
adjusting the performance score based on the comparing of the indication to the actual arrival time.

Embodiment 114. The method of embodiment 113, wherein a good performance of the trainee regarding the object is when the actual arrival position is inside the target zone and the indication is received from the HMI device within a pre-determined amount of time before the actual arrival time, or when the actual arrival position is outside the target zone and no indication is received from the HMI device within a pre-determined amount of time before the actual arrival time.

Embodiment 115. The method of embodiment 114, wherein a bad performance of the trainee regarding the object is when the actual arrival position is outside the target zone and the indication is received from the HMI device, or when the actual arrival position is inside the target zone and no indication is received from the HMI device, or when the actual arrival position is inside the target zone and the indication is received from the HMI device past a pre-determined amount of time prior to the actual arrival time.

Embodiment 116. The method of embodiment 115, further comprising:
  projecting, via the delivery device, a plurality of objects toward the target along the trajectory;
  determining, via a computing system, whether a performance of the trainee for each one of the plurality of objects is the good performance or the bad performance;
  compiling, via the computing system, each of the good performances and the bad performances; and
  determining the performance score based on the compiling.

Embodiment 117. A method for sports training comprising:
  projecting, via a delivery device, a first object toward a target;
  impacting a friction device of the delivery device with the first object;
  imparting a first spin and a first deflection to the first object in response to impacting the friction device, thereby projecting the first object along a first trajectory to the target;
  automatically adjusting, via a controller, one or more parameters of the delivery device;
  projecting, via the delivery device, a second object toward the target;
  impacting the friction device with the second object; and
  imparting a second spin and a second deflection to the second object, thereby projecting the second object along a second trajectory to the target.

Embodiment 118. The method of embodiment 117, wherein the first spin is different than the second spin, and the first deflection is different than the second deflection.

Embodiment 119. The method of embodiment 117, wherein the one or more parameters comprise one or more of:
  an air pressure supplied to the first object to propel the first object through a barrel with a center axis;
  an air volume supplied to the first object;
  an inclination of the barrel;
  an azimuthal orientation of the barrel;
  a length of the barrel;
  an inclination of the friction device which comprises a ramp and a surface material on the ramp;
  an azimuthal orientation of the friction device around the center axis of the barrel;
  an azimuthal orientation of the friction device about a longitudinal axis of the friction device;
  a distance of the friction device from the barrel;
  the surface material of the friction device;
  an object launch position from the delivery device, the object launch position being a location in 3D space of an X-Y-Z coordinate system;
  an object selection;
  a distance to the target; and
  a height of the target.

Embodiment 120. The method of embodiment 117, wherein a propulsion device of the delivery device comprises a barrel that directs the first object or the second object toward the target, the barrel having a center axis, wherein the friction device comprises a ramp positioned proximate an exit end of the barrel, wherein the adjusting the one or more parameters comprises:
  automatically adjusting a distance from the exit end of the barrel and the friction device,
  automatically adjusting an azimuthal position of the ramp around the center axis,
  automatically adjusting an inclination of the ramp relative to the center axis,
  automatically adjusting an azimuthal orientation of the ramp about a longitudinal axis of the ramp,
  automatically adjusting a speed at which an object impacts the friction device, or combinations thereof.

Embodiment 121. A system for sports training comprising:
  a delivery device that projects a first object toward a target along a first trajectory and a second object toward a target along a second trajectory, the delivery device comprising:
    a propulsion device that propels the first object or the second object from the delivery device, and
    a friction device that imparts a spin and a deflection to the first object or the second object as the respective first object or second object is propelled toward the target, wherein the friction device is automatically controlled to vary the second trajectory of the second object compared to the first trajectory of the first object.

Embodiment 122. The system of embodiment 121, wherein the propulsion device comprises a barrel that directs the first object or the second object toward the target, the barrel having a center axis, wherein the friction device comprises a ramp positioned proximate an exit end of the barrel.

Embodiment 123. The system of embodiment 122, wherein the ramp is configured to extend or contract along the center axis.

Embodiment 124. The system of embodiment 123, wherein the ramp is configured to incline toward or away from the center axis.

Embodiment 125. The system of embodiment 124, wherein the ramp is configured to rotate around a longitudinal axis of the ramp.

Embodiment 126. The system of embodiment 121, wherein characteristics of either one of the first trajectory or the second trajectory are controlled by settings of one or more parameters of the delivery device.

Embodiment 127. The system of embodiment 126, wherein the one or more parameters comprise one or more of:
  air pressure supplied to the first object or the second object to propel the respective first or second object through a barrel with a center axis;
  air volume supplied to the first object or the second object;
  inclination of the barrel;
  azimuthal orientation of the barrel;
  length of the barrel;
  inclination of the friction device which comprises a ramp and a surface material on the ramp;
  azimuthal orientation of the friction device around the center axis of the barrel;

azimuthal orientation of the friction device around a longitudinal axis of the friction device;

distance of the friction device from the barrel;

the surface material of the friction device;

object launch position from the delivery device, the object launch position being a location in 3D space of an X-Y-Z coordinate system;

object selection;

distance to the target; and height of the target.

Embodiment 128. The system of embodiment 126, wherein settings of the one or more parameters for the first trajectory are different than settings of the one or more parameters for the second trajectory.

Embodiment 129. The system of embodiment 126, wherein a controller is configured to adjust the settings of the one or more parameters to project the second object along the second trajectory.

While the present disclosure may be susceptible to various modifications and alternative forms, specific embodiments have been shown by way of example in the drawings and tables and have been described in detail herein. However, it should be understood that the embodiments are not intended to be limited to the particular forms disclosed. Rather, the disclosure is to cover all modifications, equivalents, and alternatives falling within the spirit and scope of the disclosure as defined by the following appended claims. Further, although trainee embodiments are discussed herein, the disclosure is intended to cover all combinations of these embodiments.

The invention claimed is:

1. A system for training a trainee in performing a sport, the system comprising:
a delivery device that projects an object toward a target or a trainee along a trajectory, wherein the delivery device comprises a projection device that projects the object toward the target or the trainee and is configured to impact a friction device as the object travels along the trajectory toward the target or the trainee;
a sensor that is configured to detect eye characteristics of the trainee while the trainee tracks the object after the object impacts the friction device; and
a computing system configured to determine a score of the trainee based upon the detected eye characteristics.

2. The system of claim 1, wherein the sensor is an imaging system that captures imagery of the trainee and analyzes the imagery to determine the eye characteristics of the trainee.

3. The system of claim 2, wherein the computing system comprises non-transitory memory storage which stores program instructions and informational databases.

4. The system of claim 2, wherein the imaging system comprises a controller and an imaging sensor.

5. The system of claim 4, wherein the imaging sensor comprises:
a camera;
a 2D camera;
a 3D camera;
a light detection and ranging (LiDAR) sensor; or
combinations thereof.

6. The system of claim 1, wherein the eye characteristics comprise:
direction of line of sight of an eye of the trainee;
direction of fovea vision of the eye;
direction of center vision of the eye;
movement of the eye in an eye socket;
movement of an iris of the eye;
size of a pupil of the eye; and
combinations thereof.

7. The system of claim 1, wherein the eye characteristics comprise a direction of a center vision of an eye of the trainee, and wherein the computing system is configured to perform a comparison of the trajectory of the object to the direction of the center vision of the eye as the trainee tracks the object along at least a portion of the trajectory.

8. The system of claim 7, wherein the score is based on the comparison of the trajectory and the direction of the center vision of the eye.

9. A system for training a trainee in performing a sport, the system comprising:
a delivery device that projects an object toward a target or a trainee along a trajectory;
a sensor that is configured to detect eye characteristics of the trainee while the trainee tracks the object; and
a computing system configured to determine a score of the trainee based upon the detected eye characteristics,
wherein the eye characteristics comprise a direction of a center vision of an eye of the trainee,
wherein the computing system is configured to perform a comparison of the trajectory of the object to the direction of the center vision of the eye as the trainee tracks the object along at least a portion of the trajectory,
wherein the score is based on the comparison of the trajectory and the direction of the center vision of the eye,
wherein the computing system controls various aspects of the delivery device to project the object along the trajectory to improve a performance of the trainee in the sport, and
wherein the object has a size that is smaller than a corresponding regulation object for the sport.

10. The system of claim 1, wherein the computing system is configured to detect an X-Y-Z location of the object in an X-Y-Z coordinate three-dimensional (3D) space as the object travels along the trajectory.

11. The system of claim 10, wherein the computing system captures the eye characteristics of an eye of the trainee as the trainee tracks the object along the trajectory, and wherein the computing system determines the score of an ability of the trainee, based on the eye characteristics, to track the object along at least a portion of the trajectory.

12. A method for sports training comprising:
projecting, via a delivery device, an object toward a target or a trainee along a trajectory;
tracking the object along at least a distal portion of the trajectory, wherein the distal portion of the trajectory is proximate the target or the trainee;
scoring a performance score of the trainee to track the object along the distal portion of the trajectory; and
based on the scoring, increasing or decreasing a distance of the distal portion of the trajectory along which the trainee is configured to track the object prior to the object arriving at the target or the trainee.

13. The method of claim 12, wherein increasing the distance allows the trainee an increased amount of time to track the object, and wherein decreasing the distance allows the trainee a decreased amount of time to track the object.

14. The method of claim 12, further comprising positioning a screen along the trajectory between the delivery device, and the target or the trainee, wherein a distance between the screen and the target or the trainee defines the distance of the distal portion of the trajectory.

15. The method of claim 14, wherein the screen comprises an opening through which the object is projected.

16. The method of claim 14, wherein the screen blocks a view of a proximal portion of the trajectory from the trainee.

17. The method of claim 14, further comprising:
moving the screen horizontally, vertically, or a combination thereof relative to the target or the trainee with the distance being increased, decreased, or unchanged.

18. The method of claim 14, wherein the screen comprises a pair of screens which are moved in unison when the pair of screens is moved horizontally, vertically, axially, or a combination thereof relative to the target or the trainee.

19. The method of claim 12, further comprising positioning a light source along the trajectory between the delivery device and the target, wherein a distance between the light source and the target defines the distance of the distal portion of the trajectory.

20. The method of claim 19, further comprising:
illuminating the object with a first illumination as the object travels along a proximal portion of the trajectory; and
illuminating the object with a second illumination as the object travels along the distal portion of the trajectory, wherein the first illumination is reduced compared to the second illumination.

\* \* \* \* \*